(12) United States Patent
Singh et al.

(10) Patent No.: US 6,627,406 B1
(45) Date of Patent: Sep. 30, 2003

(54) SAMPLE EVAPORATIVE CONTROL

(75) Inventors: Sharat Singh, San Jose, CA (US);
Vivian Xiao, San Jose, CA (US); Ian Gibbons, Portola Valley, CA (US);
Travis Boone, Oakland, CA (US);
Torleif Ove Bjornson, Gilroy, CA (US); Herbert H. Hooper, Belmont, CA (US); Edwin F. Ullman, Atherton, CA (US)

(73) Assignee: Aclara BioSciences, Inc., Mountain View, CA (US)

( * ) Notice: Subject to any disclaimer, the term of this patent is extended or adjusted under 35 U.S.C. 154(b) by 0 days.

(21) Appl. No.: 09/568,786

(22) Filed: May 10, 2000

Related U.S. Application Data

(63) Continuation-in-part of application No. 09/470,677, filed on Dec. 23, 1999, now Pat. No. 6,555,389.
(60) Provisional application No. 60/140,180, filed on Jun. 18, 1999, and provisional application No. 60/133,448, filed on May 11, 1999.

(51) Int. Cl.[7] .......................... G01N 33/53; G01N 21/00
(52) U.S. Cl. .............................. 435/7.1; 435/8; 422/50; 422/58; 422/99
(58) Field of Search .......................... 422/55, 58, 68.1, 422/82.01, 101; 435/287.1, 288.4, 288.5, 7.1, 7.94; 436/514, 518, 535, 149, 150, 151

(56) References Cited

U.S. PATENT DOCUMENTS 5,783,148 A * 7/1998 Cottingham et al. ........ 422/102
5,958,203 A * 9/1999 Parce et al. ................. 204/451
6,033,544 A * 3/2000 Demers et al. ............. 204/450

FOREIGN PATENT DOCUMENTS

WO    WO 00/25921    7/1999

* cited by examiner

Primary Examiner—Padmashri Ponnaluri
Assistant Examiner—My-Chau T. Tran
(74) Attorney, Agent, or Firm—Perkins Coie LLP; Peter J. Dehlinger; Jacqueline F. Mahoney

(57) ABSTRACT

Devices and methods are provided using microfluidic devices for manipulating small volumes and determining a variety of chemical and physical events. The devices rely upon an opening to the atmosphere of a small volume in a zone, where a sample is placed in the zone where evaporation can occur. The zone is maintained in contact with a liquid medium that serves to replenish the liquid in the zone and maintain the composition of the mixture in the zone substantially constant. The diffusion of components in the zone is restricted during the course of the determination by the liquid flux into the zone.

13 Claims, 22 Drawing Sheets

162  164 160 158 110   154 152 156

SAMPLE EVAPORATIVE CONTROL

CROSS-REFERENCE TO RELATED APPLICATIONS

This application is a continuation-in-part of application Ser. No. 09/470,677, filed Dec. 23, 1999, now U.S. Pat. No. 6,555,389, which claims the benefit of priority to provisional applications No. 60/133,448, filed on May 11, 1999 and No. 60/140,180, filed Jun. 18, 1999, which disclosures are all incorporated herein by reference.

TECHNICAL FIELD

The field of this invention is manipulation of small volumes comprising a volatile liquid.

BACKGROUND

Microfluidic devices comprise small capillary channels in a solid substrate, where the channels are usually present as a network. Various orifices are provided for communicating with the channels. Because of the small volumes of the networks and the individual channels many benefits adhere. The small volumes require less reagent and sample, frequently being limited by the level of detection available. In addition, because of the small volumes, reactions are very rapid. The networks allow for efficient movement of the components from one site to the next and with little loss of the components. Also, various components may be brought together, separated by different operations and the individual fractions used for various purposes.

The microfluidic devices lend themselves for various assays involving candidate compounds, where binding events are measured, enzyme activity measured, or metabolic processes measured. In this way, the effect of the candidate compounds on the indicated events may be determined. Where one is interested in comparing the effect of different candidate compounds, it is necessary that the amount of the candidate compound and other solutions that will be used are aqueous. Unless one uses relatively drastic measures, the water will rapidly evaporate. Transfers of aqueous or other solutions involving manipulative steps where the solution is exposed to the atmosphere for any length of time will invariably result in some evaporation, particularly where there are sequential additions, and the solvent from the earlier additions is evaporating while adding the next addition and during the interim between additions. In addition, incubations can result in evaporation, even where the container is covered. The problem is exacerbated where one is interested in high throughput screening, which may involve many very small aliquots of different solutions to multiple sites on a microfluidic device. Using foreign substances to diminish the evaporation can lead to contamination, require repetitive cleaning and create other detrimental issues.

Various methods have been tried, such as cooling the liquids, so as to substantially reduce evaporation, adding a lower volatility liquid over the surface of the sample, ambient humidity, adding droplets of solvent to the sample after its deposition to maintain the volume, and the like. All of these approaches are not generally useful and have severe disadvantages for use with small volumes, which must be transferred to a reaction vessel. There is a need for improved methods for manipulating nanoliter volumes when dealing with microfluidic devices, particularly associated with high throughput screening of compounds, diagnostic assays or other investigative procedures.

BRIEF DESCRIPTION OF THE PRIOR ART

U.S. Pat. Nos. 5,576,197 and 5,282,543 disclose the use of wax and other flexible materials, respectively, to inhibit evaporation. Microfluidic devices are described in U.S. Pat. Nos. 5,885,470; 5,858,195; 5,750,015; 5,599,432; and 5,126,022. Methods of evaporative control are disclosed in WO98/33052 and WO99/34920.

SUMMARY OF THE INVENTION

Methods and devices are provided for the manipulation of small volumes in association with determinations employing microfluidic devices, where a substantial portion of the liquid is subject to evaporation during the operation. The microfluidic devices comprise a partial enclosure for a zone for receiving a small amount of a component of the operation, usually as a solution comprising a component of a reaction. The zone is bounded by a meniscus, whose position is affected by the nature of the zone, which zone may have a non-wettable border, which may be made wettable by addition of a detergent or may be wettable. During the operation, the liquid in the zone is subject to evaporative loss of liquid, and the zone is in fluid exchange relationship with a channel housing a replenishing liquid. The channel liquid replenishes the liquid in the zone and may serve as a source of a second or more components of the operation. During the operation, the position of the meniscus will be relatively fixed in a number of embodiments, while in other embodiments be subject to the movement of liquid into and out of a capillary channel. Either substantially immediately upon entering the zone, the component is in contact with the channel liquid, so that any solvent lost by evaporation in the zone can be replenished, or the component is placed at a site where evaporation of any liquid may occur and the residue is dissolved in a liquid discharged from a capillary channel, where contact is maintained with the solution which forms the zone and the solution in the capillary channel. The reaction volume is substantially maintained in the zone defined by a major portion of the components of interest being present in the zone, comprising the region between a meniscus and the region of liquid exchange between the zone and the channel.

BRIEF DESCRIPTION OF THE FIGURES

FIGS. 2A-1, 2B-1, and 2C-1 are diagrammatic side-views of the microfluidic devices depicted in FIGS. 2A, 2B, and 2C, respectively;

DESCRIPTION OF THE SPECIFIC EMBODIMENTS

Figure 1:
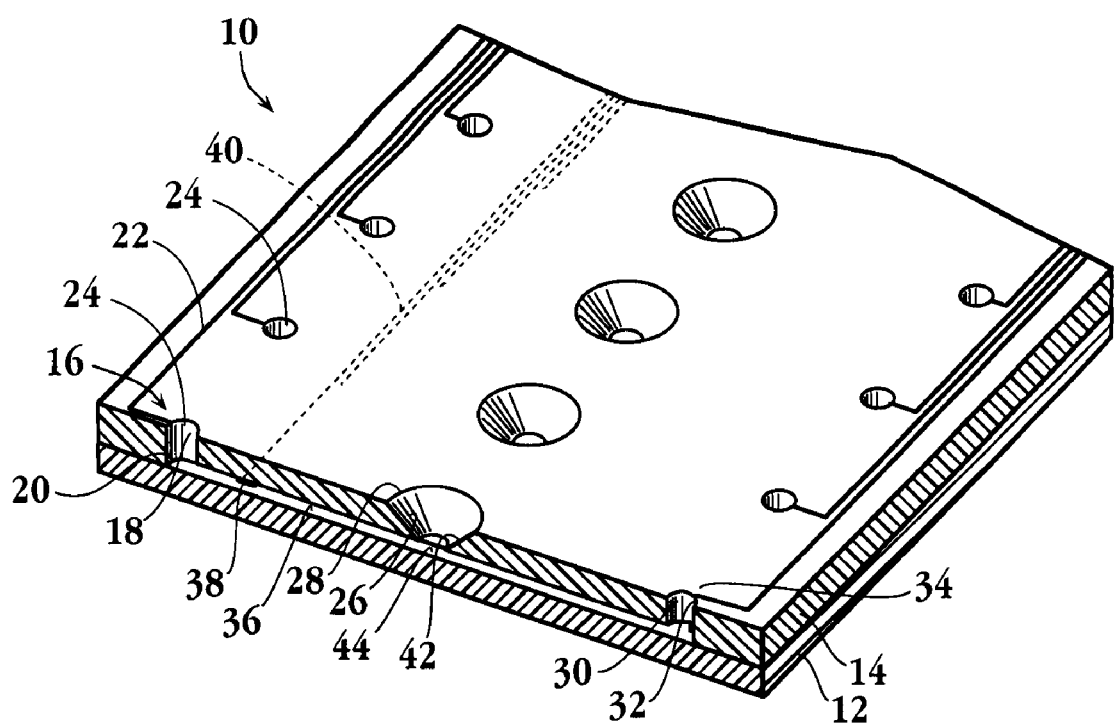
FIG. 1 is a fragmentary perspective view of a microfluidic device according to this invention.

Improvements are provided for performing reactions in microfluidic devices, using methods and devices allowing for efficient manipulation of small volumes of solutions comprising evaporative solvents. The reaction components will normally be in one or more additions to the zone and optionally a liquid in a channel in liquid exchange relationship with the zone. The channel liquid may have one or more components, or all of the components of the reaction may be added to the zone. Microfluidic devices are provided comprising at least one unit having a partial enclosure defining at least a portion of the zone and connected to a capillary channel, so that the zone is open to the atmosphere during additions to the zone, which enclosure may be sealed after each manipulation or after all manipulations are complete. The devices have microstructures, which are for the most part channels, reservoirs and wells, but may include other microstructures, such as barriers, salt bridges, projections in the channels, etc. The liquid containing capillary channel is in liquid transfer relationship with the zone, replenishing liquid lost by evaporation and creating a liquid flux in the channel toward the zone. The opening permits convenient addition of solutes and solutions to the zone, where evaporation of liquid into the atmosphere may occur during the transfer of the solution into the zone and thereafter. The conditions of the addition will usually be at below or at ambient or elevated temperature and pressure, although higher temperatures may be employed during the addition.

The zone has a border, a meniscus, as a result of a wettable/non-wettable border on the surface of the enclosure, a sharp change in direction of the wall of the enclosure, the termination of the zone or the hydraulic head of the system. The height of the meniscus will be controlled so that, after addition of liquid to the zone, particularly the assay well, the position of the meniscus will be restored to its equilibrium level, due to evaporation and fluid to movement into the capillary channel. Where the zone is connected to a reservoir, and is parallel to the reservoir, the hydrostatic head is selected to avoid pushing the meniscus significantly past the border. For a non-wettable/wettable boundary on the surface of the enclosure, which may be at either end of the enclosure, the meniscus will normally form at the boundary. The meniscus at the boundary will normally be convex. For a wettable border, where the border is wettable due to the wall being hydrophilic (for a polar medium) or the addition of a detergent, where the wall is hydrophobic (for a polar medium), the border will usually be at the termination of the zone. With a wettable border, the meniscus will usually be concave. The method permits the formation of the product of the reaction to be retained within a small volume for ease of detection.

Assays may be carried out for extended times with nanovolume reaction mixtures comprising a volatile solvent, while the reaction mixture is exposed to the atmosphere. Reaction volumes of greater than 10 nl, usually in the range of about 50 nl to 2 $\mu$l, more usually up to 500 nl, are employed, where one or more components are added to the reaction zone containing the reaction volume, where the components or their products are substantially retained in the zone. The components are added as solutions of from about 10 pl to 300 nl, more usually of from about 10 to 200 nl, and preferably not more than about 100 nl. The reaction mixture is bounded by a meniscus and the solution directly under the meniscus. The additions are made directly onto or through the meniscus, which may be surrounded by a wall forming a well or passageway. Of particular interest are binding assays involving proteins, where a candidate compound is tested and the binding level of the candidate compound to the protein is determined. The assay protocol involves a reaction mixture having a meniscus exposed to the air, where the candidate compound may be in the liquid of the reaction mixture with the meniscus border or added to the reaction mixture. At least one other component of the reaction is then added to the reaction mixture, in accordance with the requirements of the determination, e.g. substrate for an enzyme, competitive labeled compound for a binding protein, etc. Depending on the nature of the label and the protocol, the label may be detected in the reaction mixture.

The zone is defined functionally as comprising at least about 50% of a component of interest, usually at least about 50% of the components added to the zone, preferably at least 60%, more preferably, at least about 80% and up to 95 or 100%. The zone will always be a very small volume and where the operation of interest provides a detectable signal, will usually be the region from which the signal is detected. Desirably, the zone will be easily addressable to maximize the signal for the determination, so that the zone may approximate a cylinder. As will be described, the zone need not be significantly enclosed and may be confined by solid and liquid barriers, in addition to being open to the atmosphere, at least initially during the operation.

The zone may have a portion of the zone at a non-wettable/wettable interface or border, at a site of an abrupt change of direction of the wall of the enclosure, which may include the end of the enclosure or at the abrupt change, e.g. expansiori having a shelf, or extend to the end or beyond the end of the enclosure. (By wettable is intended that the surface will be coated with the liquid and in a capillary the liquid will be drawn into the capillary by surface tension. For a non-wettable border, in the case of a polar solvent, particularly an aqueous solvent, the surface will be hydrophilic, while the non-wettable surface will be hydrophobic. Where the solvent is non-polar, e.g. hydrocarbon, the reverse will be true for wettable and non-wettable.) This interface may be at a region in an enclosure, at the edge of a capillary, where the outer portion of the capillary is non-wettable, or other structure where migration of the liquid in the zone is inhibited from moving into another area as a result of the surface tension or contact angle between the liquid and the non-wettable area.

In referring to microfluidic devices it is intended that the devices comprise capillary channels having cross-sections of less than about 5 $mm^2$, usually less than about 1 $mm^2$, frequently less than about 0.5 $mm^2$, more frequently less than about 0.1 $mm^2$, and frequently as small as about 0.005 $mm^2$ or less, generally being at least about 0.025 $mm^2$, more usually at least about 0.01 $mm^2$. In addition, the devices have a zone in which the reaction of interest occurs, which when partially enclosed, so that a volume can be defined, the volume of the zone that comprises the liquid of interest will be less than about 5 $\mu l$, usually less than about 1 $\mu l$, and frequently less than about 0.5 $\mu l$, and may be as small as about 50 nl or less, usually at least about 10 nl. At a non-wettable border, the reaction volume will include the volume under the meniscus and above the non-wettable border, where the meniscus may extend beyond the non-wettable border. The reaction volume may also include a volume in the capillary channel under the meniscus and extending a short distance from the area under the meniscus. The partial enclosure, when present, may have a substantially larger volume than the volume of the zone, usually not more than about 10× larger, more usually not more than about 5× larger, than the volume of the zone. The zone, when partially enclosed, such as a well, may have a cross-sectional area smaller than the channel cross-sectional area, but will usually have a cross-sectional area larger than the cross-sectional area of the channel, being at least twice the area, conveniently at least about 5 times, and more conveniently may exceed 20 times. Where the zone is not bordered by a non-wettable boundary, a partially enclosed zone will usually be the volume of the enclosure and may include a portion of the region of the channel beneath the partial enclosure.

The capillary channel may be round, rectangular, frusto-conical, truncated pyramid, normally inverted, or other shape, preferably a regular shape. Of particular interest is when the capillary channel is formed in a substrate, e.g. a plastic card, and the channel is enclosed with a film which is adhered to the body of the substrate. In this case, the channel will not be circular and will have a depth and width. In addition, the width and/or depth may not be constant the length of the channel. In referring to width and/or depth, it is intended the average width, although differences from the average will usually not exceed more than by 100%, usually by not more than about 50%.

For the non-circular channel, the depth of the capillary channel will generally be in the range of about 10 $\mu m$ to 2 mm, usually in the range of about 25 $\mu m$ to 1 mm, more usually in the range of about 25 $\mu m$ to 500 $\mu m$, preferably less than about 250 $\mu m$, and at least about 10 $\mu m$, usually at least about 20 $\mu m$, particularly where the capillary channel serves as the floor of the zone. For the circular capillary, the diameter will generally be in the range of about 10 $\mu m$ to about 2 mm, more usually at least about 20 $\mu m$ to 2 mm. The device may have one or more capillary channels in liquid exchange relationship with the zone, where the channels may be in the same or different planes, so that there may be liquid contact at two or more different interfaces. Conveniently, the signal may be determined without having to view the signal through the material with which the device is composed.

By having a network of channels, where some or all of the channels may interconnect, substantial flexibility is achieved. It is understood that for the purposes of this invention, channels and capillaries may be used interchangeably, where capillary (includes channel, unless it is clear from the context that channel intends a cross-section greater than a capillary or is open along its length) intends that there is liquid movement upon introduction of liquid into one end of a capillary due to surface tension. The channels may serve to deliver and remove agents from one or more zones, simultaneously or successively, depending on the to plumbing employed. One may provide for miniaturized pumps, separation walls, gates, etc., so as to be able to direct liquids to specific zones. One may provide for successive replacement of liquids in the channels, whereby different reagents may be directed to the zones, which allows for modification of reactions, stepwise performance of reactions, removal of agents from the zones, etc. By modulating the temperature of the liquid in the channels one can modulate the temperature of the liquid in the zones. Thus, one could provide for heating and cooling of the mixture in the zone.

The zones provide opportunities for the introduction of one or a few particles, such as beads, colloidal particles, cells, organelles, microsomes, and the like. The small volumes allow for enhanced signals from the particles, allowing for investigations or determinations, where only a few particles need be present. For cells, one may provide 1 cell or more, usually more than about 50 cells for statistically significant results, and generally fewer than 1,000 cells, usually fewer than about 500 cells. Cells may be dispersed in the zone, adhered to the surface of the zone, as a wall of a well or channel, or the like. The small volume of the wells allows for growing cells in the wells, where the reservoirs may serve as a source of nutrients. Where one is interested in unique events, such as mutagenesis of a genome, a single cell can be maintained in a well and the occurrence of the unique event assayed. For example, if one were interested in mutagenizing an enzyme to be resistant to inhibition by a known inhibitor for the wild type enzyme, each well containing a single cell could be assayed with substrate and inhibitor and production of a product would indicate that the enzyme had been successfully mutagenized. Alternatively, cells may be genetically modified to have a reporter gene, e.g. an enzyme that produces a detectable product from its substrate, a fluorescent protein, etc., so that the operation either turns the reporter gene on or off. This type of assay has found extensive use in studying transcription factors, as well as other cellular pathways.

In one embodiment, one has an orifice forming a well through the wall of a capillary channel, where the partial enclosure is at least the height of the thickness of the wall of the capillary. The well may be at any angle in relation to a reference point to which the position of the capillary may be related. For example, where the capillary is in a solid substrate, particularly having a groove or trench in a plate and a cover enclosing the plate, the orifice may be in the cover or in the side of the plate or in the substrate opposite from the plate, or any angle in between. However, for the most part the orifice will be vertical and above the capillary during operation. In this embodiment, where the wall is non-circular, the well is normally in the cover enclosing the channel in the substrate. The well can be varied in accordance with the thickness of the cover, which up to a degree may be arbitrarily chosen. Thus, covers may be from about 0.05 to 2 mm in thickness, where the height of the well would be the same. Alternatively, one may fuse or form a tube or collar to the substrate to obtain any length for the partial enclosure. The partial enclosure serves as a container, generally having a cross-sectional area at least about one-half, frequently at least about equal and desirably greater than about the cross-sectional dimension of the channel. The volume of liquid in the zone, comprising at least a portion of the well and optionally a portion of the channel under the well, will be controlled in part by the nature of the wall of the partial enclosure of the zone, where none or a portion of the wall will be non-wettable by the liquid in the zone. (By "non-wettable" is intended that the liquid in the zone will not migrate past the region that is non-wettable when no force is applied to the liquid to drive the liquid past such region. In effect, the contact angle between the liquid and the wall is such as to inhibit the rise of the liquid in the partial enclosure. Conversely, "wettable" intends that the liquid will wet the surface and rise in a capillary in the absence of a negative force.) Where the partial enclosure is wettable, the zone may encompass the enclosure, depending on the hydrostatic forces between the zone and the reservoir(s).

In this embodiment it appears that the evaporation from the zones results in the movement of liquid from the channel into the zone to retain the height of the meniscus. The liquid in the channel is, of course, maintained by the reservoir(s), whose volume will generally be large compared to the volume of the channel and the liquid in the zone. Evaporation from the zone may be further enhanced by having: a temperature differential between the liquid in the zone and the liquid in the reservoir; a differential air flow; a differential humidity; or the like, where the condition at the zone is to enhance the evaporation at the zone, as compared to the reservoir. The temperature during the time of addition may be ambient, reduced or elevated, generally in the range of about 10° C. to about 65° C., more usually in the range of about 20° C. to 50° C., so long as the rate of evaporation is not unduly great to interfere with the replenishment.

In other embodiments, one may have a discontinuity between the liquid in the zone and the liquid in the channel, where liquid from the channel may be brought into contact with liquid in the zone. In this instance, the zone may be substantially open and only have a floor or be substantially enclosed, where the channel could be connected to the zone through an orifice at the bottom or at the side of the zone. One has a channel in proximity to the zone, where the liquid in the channel may be expressed into the zone and optionally withdrawn to reduce, but not completely terminate, evaporation during subsequent operation.

Depending upon the nature of the operation, different protocols may be employed.

In one protocol, a liquid, normally a solution, is added to the zone and upon introduction into the zone comes into substantially immediate contact with liquid from a capillary channel. The liquid may be added to the zone, where the channel liquid may be the floor of the zone, a droplet between two channels or may be in a side channel, where the channel may be vertical or horizontal in relation to the zone. The solution may be retained in the zone or withdrawn into the capillary channel during the course of the reaction. After sufficient time for reaction to occur, the resulting product may be processed in accordance with the operation, and, as appropriate, a signal determined. As an illustration, with a volume of the zone of about 200 nl, with a capillary channel having a cross-sectional area of 450×100 μm, the zone would be withdrawn into the capillary about 4–5 mm, assuming all of the reaction mixture in the zone was withdrawn into the channel.

In a second protocol, a solute or solution may be added to a surface in the zone and any evaporation of the solvent ignored. (In referring to a solution, it should be understood that any liquid mixture of two components is intended, such as a mixture of liquids or a solute and a solvent. In some instances, dispersions are also included, such as colloidal dispersions, as may be understood from the context.) Liquid for the reaction mixture is then discharged from the channel to dissolve the residue, liquid or solid, to form the reaction mixture. The reaction mixture solution is maintained in contact with the liquid in the channel to replenish any solvent, which evaporates, or the reaction solution is withdrawn into the channel to substantially inhibit any evaporation. After sufficient time for reaction to occur, the resulting product may be processed in accordance with the operation, and, as appropriate, a signal determined.

Evaporation helps keep the zone of the reaction mixture defined. Despite the diffusion of small molecules, the liquid flux into the zone during the operation inhibits the loss of the small molecules into the channel away from the zone. Based on this consideration, preferably the zone will be designed to have a relatively short vertical path from the meniscus to the end of the zone. Furthermore, depending on the height of the partial enclosure, one can add various solutions, where the solutions will mix in the partial enclosure and as the height of the meniscus is restored through evaporation and the liquid moving into the channel, the liquid at the bottom of the zone is moved back into the channel.

In performing the reaction there will be at least one component of the reaction added through the opening into the zone and, as described, conveniently, at least one component of the reaction in the solution in the channel. Frequently, components added to the zone will be higher molecular weight components of the reaction, generally exceeding 2 kD, frequently exceeding 5 kD, and may exceed 10 kD. Where small organic molecules are being screened for activity, they may conveniently be added to the zone and will have a molecular weight in the range of about 150–2500 Dal or may be added to the reservoir(s). One or more additions may be made into the zone, adding one or more components to the zone. To minimize the additions, mixtures of components may be added. By virtue of the contact between the solution in the zone (zone solution) and the solution in the channel (channel solution), components in the channel solution will diffuse into the zone solution to equilibrate the concentration of the component(s) in the channel solution between the two solutions, while the small cross-section of the channel, the capillary forces in the well and/or evaporation keep the zone defined. Upon completion of the addition(s), one can then determine whether the desired reaction occurred.

A plurality of additions may be made concurrently or consecutively, where the time between additions may be very short, bordering on simultaneous addition, or require relatively long intervals, e.g. 30 sec or more, where the intermediate reaction mixtures may be incubated, processed, e.g. heated, or withdrawn into the channel to inhibit evaporation. Generally, the volume of the solution added to the zone will be less than 0.005 ml, frequently less than about 1 $\mu$l and more frequently less than about 0.5 $\mu$l usually being at least about 10 pl, more usually being at least about 1 nl, frequently at least about 10 nl, depending on the ability to accurately transfer liquids to the zone.

Additions may be achieved using piezoelectric devices, e.g. ink-jet devices, pins, slotted pins, pipettes, capillary electrokinesis injection, etc. Preferably, the delivery devices will not require contact with the solution in the microstructure or the subject device. The particular manner of transfer will depend on the volume to be transferred, the nature of the composition to be transferred, the speed with which the composition can be transferred, the accuracy required for dispensing the composition, and the like.

Usually, the solution in the channel will be a buffered solution, where the formality of the buffer, which may include other ions, will be not more than about 200 mM, more usually not more than about 100 mM, and frequently less than about 75 mM, usually greater than about 5 mM, more usually being greater than about 10 mM. Buffers which may find use include phosphate, carbonate, borate, MOPS, HEPES, Tris, tricine, etc., the buffer generally being selected in accordance with the nature of the reaction. Where capillary electrokinesis is used, the buffer in the channel may be selected to be suitable for the capillary electrokinesis, may be modified after performing the operation or may be transferred to the electrokinesis system and modified there. The concentration of the components, which are added, may vary widely depending on the volume of the solution. Concentrations may vary from about 1 fM to 0.1M, usually being in the range of about 1 pM to 0.01M, the concentration and volume depending on the level of detection of the detectable signal and the manner in which the signal is generated. Since the volumes added to the zone are small compared to the volume of solution in the system comprising the channel and reservoirs, the area of interface between the zone and channel is small, and the evaporative flux inhibits diffusion of components of the zone from leaving the zone, there will be limited equilibration between the added solution and the liquid in the channel.

Desirably, the buffer solution in the channel will be the same as the buffer solution in the added solutions, where the difference will then be as to the components and any non-aqueous solvents. One can enhance fluid flow toward the zone by having the added solution at a higher formality than the solution in the channel, although an increased formality of the added solution will occur as a result of evaporation, except for the compensation provided by the solution in the channel. Where a component, particularly the test compound, is added as a non-aqueous solution, it may be desirable to include the test compound in the reservoir and channel, rather than adding the solution to the opening in the zone. This avoids problems of dissolving the test compound in the buffer solution, where the test compound is only moderately soluble in water. In this way, the non-aqueous solvent becomes equilibrated in the reservoir(s) and the test compound is instantaneously diluted into the buffer, preventing separation of the test compound.

The subject device can allow for sample dilution, for example, where the sample comprises a solvent that may interfere with an intended operation. One can add the sample solution to a reservoir prior or subsequent to introduction of the reservoir solution into the reservoir. In the former case, one may have to wait for equilibration of the test sample compound through the unit. In the latter case, one can inhibit the movement of the sample solution until diluted with the reservoir solution and then distribute the sample containing solution throughout the unit. Pneumatics, removable barriers, valves, etc. may govern movement of the sample and the sample solution. This operation may be achieved by using a central dilution vessel into which the sample and diluent are added. The dilution vessel may have an interface with liquid in a channel for replenishment of liquid, which has evaporated.

Capillary channels would lead from the dilution vessel to one or more, usually a plurality of zones, where the diluted sample would migrate by capillary action to the individual zones. As appropriate, pneumatics, including a hydrostatic head, may be used to direct the flow of the liquids. The liquid from the dilution vessel would mix with other liquid(s) in the zone. In this way, small volumes of a reagent or candidate compound would be distributed among a number of zones for a subsequent operation, without initially having to manipulate small volumes. The same mechanism may be used to distribute an expensive reagent to a plurality of zones. In this situation, it may not be necessary to dilute the reagent, where the reagent may be directly added to the central vessel. The reagent would then be distributed from the vessel to the various zones. Desirably, the capillary channels will be relatively short, usually less than 1 cm, more usually less than about 0.5 cm and more than about 0.1 mm. The volume of the vessel will usually be at least 100 nl, more usually at least about 300 nl and less than about 1 ml, usually less than about 0.5 ml, depending on the amount of the solution to be transferred to each of the zones and the number of zones. By having a central vessel for distribution to a plurality of zones, one can reduce errors in transferring small volumes and provide for substantially equivalent transfer to a plurality of zones, allowing for direct comparison of results in each of the zones.

One may also have one or a multiplicity of vertical capillary channels comprising a terminal region having a larger cross-sectional area than the capillary channel which may comprise a non-wettable region at or above the interface between the terminal region and the channel. The capillary would be placed in a reservoir to replenish liquid lost from the zone formed in the terminal region. As one added new liquid to the terminal region, initially the meniscus would be raised. Both evaporation and movement of the meniscus downward would occur, so that displacement of solution containing an active component would be minimized, keeping the volume of the zone minimal. The terminal region could be cylindrical, conical, or the like. Generally, the capillary channel would be circular, so that the terminal region would have at least about 1.2 times the diameter of the capillary channel, frequently at least about 1.5 times the diameter of the capillary channel and up to about 20 times.

In a first application, components are mixed and reduction of the volume of the mixture due to evaporation substantially precluded at the time of the addition by providing for contact with a solution in a channel, where the interface between the solution in the zone and the solution in the channel is relatively small, usually having a cross-sectional area of less than about 5 mm$^2$, usually less than about 2 mm$^2$, while being at least about 10 $\mu$m$^2$, more usually at least about 50 $\mu$m$^2$.

The solution added to the zone will normally involve a volatile solvent and may also include a non-volatile solvent, particularly where one or more of the components are not readily redistributed into the volatile solvent, e.g. water. Various non-volatile solvents include dimethyl sulfoxide, dimethyl fomamide, hexamethylphosphoramide, liquid organic salts, such as higher alkyl (>6) ammonium salts, polyethers, particularly polyalkylene glycols (alkylene of from 2–3 carbon atoms), such as dimethyl cellosolve, etc., where the volatility is in relation to the vapor pressure of water, where the vapor pressure of the non-aqueous solvent is generally less than half of that of water at ambient conditions. The solution may be introduced into the zone as described previously, where the method desirably assures a consistent amount of the solution being transferred. Alternatively, as described above, the solution may be distributed from a central vessel through capillary channels to a plurality of zones.

Depending on the protocol, the zone, which defines the reaction volume, may be contained in a region, e.g. space or gap, between two capillaries, on a platform, in a cylinder, a portion of a capillary channel, a vessel, such as a well, port, passageway or chamber, etc. The zone may be contained in a vessel of sufficient depth to serve as a receiving vessel and/or a portion of the channel, underneath and/or adjacent to the vessel. The significance of the zone is that it provides the area-of liquid exchange between the components of the added solution and the channel solution during the reaction. The zone has an opening that allows for access for addition of solutions, provides for liquid exchange between liquid in the zone and liquid in the channel, and permits evaporation. The channel will have a source of liquid for filling the channel, usually a reservoir, and normally be filled with the liquid prior to addition to the zone, which liquid will usually be buffer, including electrokinesis buffer, containing a component of interest, and/or reagent(s) or additive(s), or the like, necessary for the reaction to occur. The liquid will usually be an aqueous liquid, having at least 20 vol. % of water, usually at least 50 vol. % of water and may be solely water as the solvent. While one could add all of the components to the zone, so that there need not be components, e.g. reagents or compound of interest, present in the liquid in the channel, it will usually be more efficient to provide at least one component in the channel solution, particularly where such component is relatively inexpensive, is provided in a non-aqueous solvent or as a matter of convenience.

In an embodiment where the channel serves as the floor of the zone or there is a floor to the zone, where a capillary channel outlet is in close proximity to the floor, a spatially restricted region will frequently be present extending upwardly beyond the periphery of the channel outlet. The region may have walls that extend beyond the top of the wall of the capillary channel. The zone may be all or partially contained in a receptacle that has a lower surface, usually a floor, and an adjacent portion of the wall that can be wetted, and desirably, but not necessarily, at least a portion of the walls, mainly a portion distal to the channel interface will be non-wettable, so that aqueous media will be primarily restricted to the lower portion of the receptacle.

Depending on the nature of the walls of the receptacle or partial enclosure, the walls may have to be modified to provide the different properties. Non-wettable walls may be made wettable by coating with an appropriate hydrophilic composition, e.g. polymers, such as polyacrylates, having hydroxy- or aminoalkyl substituents, hydrolysis of hydrophobic polymers having functionalities which can be hydrolyzed to polar functionalities upon hydrolysis, proteins, polysaccharides, polyalkyleneoxides, etc., oxidizing the surface with ozone or other oxidizing agent, functionalizing the surface by the introduction of hydroxyl, carboxyl or amino groups, etc. For creating a non-wettable surface from a wettable surface, one may coat with a higher hydrocarbon or hydrocarbon derivative, such as grease, wax, lipid, oil, etc., a hydrophobic polymer, such as polyethylene, polyamide, polyimide, polyester, etc.

In operation, a component of interest is provided in the zone, usually being added as a solution, where during the operation, none, all or part of the solvent may have evaporated. Alternatively, one may add a powder, gel or other form of the component of interest. The component may be obtained in a variety of ways being accessed from a robotic source of a large number of different components, a dispenser of a common component, or the like. In some instances, two or more components may be combined and incubated prior to addition of the mixture to the zone. In some instances, solutions may be obtained from microtiter plate wells, where the inlets and zones are positioned for receiving the contents of the wells into the zones. Microtiter plate wells usually have $96 \times n^2$ wells, where n=1–4. In this situation, one may use pins, with surface contact transfer, electrical fields, inertial forces, piezoelectric, electroosmotic force or a pressure differential to transfer the liquid in the wells to the subject zones. Generally, the volumes being transferred from the microtiter wells will be very small, being in the range described previously.

In view of the small volumes being transferred, evaporation will frequently be rapid, and may leave a dry residue of the components of the solution in the zone. The volume selected for delivery may be small enough, and the zone size and zone bottom large enough, that the solution will adhere to the bottom of zone without significantly entering or even contacting the channel inlet, where evaporation of the added solution is acceptable. Preferably, the parameters will be selected so as to inhibit evaporation to dryness.

In one embodiment, the microfluidic device will comprise a layer or substrate of plastic, glass, silicon, or other convenient materials, which may be hydrophilic, hydrophobic or combination thereof. The device will usually have a network of various channels and receptacles formed in the substrate and conveniently enclosed with a cover of the same or different material. Orifices can be provided in the cover or substrate, which orifices may serve as receptacles. There are many different methods of fabrication of a microfluidic network, which have been described in the literature. One may have a common source of liquid, which includes a manifold having a plurality of branches which provides liquid to a plurality of common channels, much in the way risers are used in plumbing in apartment buildings.

The channels may have a surface which is entirely hydrophilic, entirely hydrophobic or portions may be one or the other. For example, where there is a cover and a trench forming the channel, the trench may be hydrophobic and the cover surface enclosing the trench may be hydrophilic. It appears that having a portion of the surface hydrophilic along the length of the channel is sufficient to obtain capillary action and liquid replenishment in the zone:

A zone which may be included in a partialenclosure and a capillary channel, optionally in conjunction with other microstructures may be considered a unit. Where the subject device is to be used with microtiter well plates, each unit associated with a microtiter well would have a zone comprising at least one channel inlet, usually two opposed channel inlets. Depending on the protocol and the means of transport of fluids, one may use electroosmotic force, where there would be an independent pair of electrodes for moving liquid, or have a common electrode associated with a plurality of electrodes to provide the opposite polarity to the common electrode, with the electrodes in contact with the units. In an embodiment with individual pairs of electrodes at each unit, the operations usually would be confined to individual units having a single zone, rather than moving the composition to different sites and carrying out additional operations, although the individual pairs of electrodes could be used to provide a moving wave electrical field as described in U.S. Pat. No. 5,750,015. Thus, the substrate would provide for electrokinetic channels and the ability to receive electrodes or have the electrodes painted, adhered or otherwise present on the substrate.

However, one could provide for layered channels, where one would have additional channels connected to the unit channels that are normal to the plane of the unit channels. One would then have an additional microfluidic network for addressing the units individually and performing additional operations on the compositions. When used with microtiter well plates, one can provide for a microfluidic network having the zones positioned to be in alignment with the wells of the microtiter well plates.

The component of interest may be all or partially dissolved or dispersed and will reside in the zone. The liquid in the capillary channel may be present in the zone or may be discharged from the capillary to define the zone, where the liquid will retain continuity between the liquid in the zone and the liquid in the capillary channel. Various means can be employed for pumping the liquid from the channel into the zone, including electrokinetic, pneumatic, mechanical, sonic, capillary, thermal, or the like. While the particular mode for moving the liquid into and out of the capillary is not critical, many advantages accrue by using electroosmotic or pneumatic pumping, where small volumes can be moved in different directions by changes in direction of an electrical field or by application of differential pressures. Where electroosmotic pumping is used, one requires a channel with a region where the walls are charged or the solution includes a soluble charged polymer, such as an aminodextran, so that ions in the liquid of opposite charge to the wall charge accumulate at the wall. In the presence of an electrical field, the ions adjacent to the wall will move toward the electrode of opposite charge and carry liquid with them, providing a liquid pump. In this way, one can push liquid with significant precision from the channel into the area outside the capillary to define a zone and then withdraw the liquid in the zone back into the channel. The pump can be used to move liquid, which is not under the influence of an electrical field, diminishing electrokinetic separation in the solution. By this means, one may move liquid in defined volumes containing components, which may be adversely affected, by an electrical field. Alternatively, one may use pneumatic devices to move the liquid.

In order to automatically determine when the desired liquid volume has been introduced into the zone, rather than relying on the parameters which were used to pump the liquid into the zone, such as voltage, time, temperature, etc., one can provide for a detection system. One system uses an ionic medium, conveniently introduced into a channel connected to the zone, with a detection electrode in the ionic medium connected to a voltage source or ground. When electrokinetic pumping is employed, there will be an electrical field in the fluid. When the fluid in the zone contacts the ionic medium, a circuit will be formed with the detection electrode, which can be detected and further pumping terminated or the electrical field will be grounded and further pumping stopped. One may simply have an electrode in the zone, which when contacted with the liquid from the channel will act as described above. Instead of an electrical detection system, one may use an optical system, which detects the extent to which the liquid has penetrated the zone. The particular mode of detection will depend to some degree on the choice of the mode of transferring the fluid into and out of the zone.

If desired, evaporation during the course of the reaction may be impeded by closing the zone to the atmosphere, where feasible, adding a solvated polymer to the solution, and the like. A polymer may have the further advantage of reducing diffusion of the components from the zone into the channel solution. Polymers, which may be used, include polyethylene oxides, polypropylene oxides, ethers and esters of such polymers, polyacrylamides, dextran, modified dextrans, or other polymers which are water soluble. Generally, such polymers would be present in less than about 5 wt. % of the solution, preferably less than about 1 wt. % of the solution.

In the situation where the solvent substantially evaporates prior to dissolution in the channel liquid, the volume of liquid discharged from the channel may serve to concentrate the components from the well in the zone.

Where the zone is formed by expression of fluid from a channel, the fluid in the zone, during the brief period after introduction of the fluid from the channel into the zone, is prevented from significant reduction in volume by the reservoir of fluid in the channel. The fluid in the zone can be rapidly drawn back into the enclosed channel with substantially the same volume that was introduced from the channel into the zone and whatever fluid was present from addition of fluid to the zone, which has not previously evaporated. The zone solution may be withdrawn into the channel as a defined volume. One now has a defined volume of fluid as the zone in the channel, which will substantially retain its composition, since diffusion can be relatively slow. Furthermore, since some evaporation will occur at the channel outlet, the liquid will flow in the channel toward the zone, reducing movement of components away from the zone. In addition, by using microfluidics and electrokinesis, the zone may be moved to any site in the microfluidic network and be subject to various operations, such as the addition of reagents, separation of components, heating, cooling, etc., without significant change in its composition, except for the added components.

In another mode, one may employ opposed capillary channels to provide a continuous liquid fluid column as part of the manipulations of the various components. In this embodiment, the stream extends from one channel to the opposed channel through the zone liquid during the operation of the unit. At one or more different times, there may be a break in the column, particularly, where the column may be interrupted in the zone area. One may initially have liquid in one or both capillary channels and/or in the zone area. There may be a plurality of zones, which are not separated by walls from each other, being gaps between a plurality of channel outlets. In this situation, the opposed capillary channel outlets would be relatively close to each other, generally spaced apart by not more than about 5 mm, usually not more than about 2 mm, and preferably not more than about 1 mm. In this manner, one may have a plurality of opposed:capillary channels in a block, which are separated by a gap, where liquid may be discharged from one or both capillary channels to cross the gap and form a continuous liquid column.

The openings of the channels at the gap are conveniently in the range of about $10^2$ to $5 \times 10^5 \mu^2$. The volume of liquid in the gap will usually be in the range of about 1 to about $10^3$ nl. The liquid droplet between the opposed channels serves as the zone for addition of solutions. Various methods may be used for addition to the liquid in the gap, as described previously. Generally, each individual addition to the gap liquid or zone will not exceed about 500 nl, more usually not exceed about 250 nl. As appropriate, after each addition to the gap liquid or zone, the solution in the gap may be withdrawn into a channel and incubated and the signal then determined or discharged from the channel and the signal determined without interference from the device composition. The opposed channels may be provided in blocks comprising a plurality of channels, where one could have a planar array of opposed channels, as described in FIGS. 3 and 5, where the chamber is substituted with a gap. Additions could then be made at each gap from an array of devices for transferring liquids in small volumes and the manifold could be as depicted, or one could have different main channels providing different solutions for the different rows of units. In this way, devices can be provided which have 20 or more units, up to 2,000 or more units.

The size of the zone will be affected by the sizes of the ports, outlets and channels, volumes of the solutions added to the zones, the amount of liquid in the channel into which the components of the added solutions diffuse, by the nature (regions of wettability and non-wettability) of the walls enclosing the zone, the rate of evaporation, which may be related to the humidity, depth of the zone and air flow above the zone, the time of the reaction, the temperature, the composition of the solution in the channel, particularly as to the solution viscosity, and the like. Generally, these parameters will be selected to provide a dilution in the zone of the sample component added to the zone in the range of about 0.1 to 10:1, during the course of the reaction. Incubations may involve from about 1 min. to 24 h, usually not exceeding about 12 h. The reaction time will usually require at least 1 min., usually at least about 5 mins, and not more than about 6h, usually not more than abut 2 h. Ambient conditions will usually suffice, with temperatures below about 60° C., more usually not more than about 40° C. In some situations where thermal cycling is involved, temperatures may be as high as 95° C., usually not exceeding about 85° C., and cycling between 45° C. and 95° C. Heating can be achieved with lasers, light flashes, resistance heaters, infrared, heat transfer, conduction, magnetic heaters, and the like.

Components of interest for use in many of the determinations include small organic molecules about 100 Dal to 5 kDal in molecular weight, more usually not more than about 2.5 kDal, oligopeptides, oligonucleotides, and oligosaccharides, proteins, sugars, nucleic acids, microsomes, membranes, cells, organelles, tissue, etc., where the components may serve as ligands, receptors, enzymes, substrates, cofactors, functional nucleic acid sequences, e.g., promoters and enhancers, transcription factors, etc. Reactions of interest will include binding reactions, which may involve enzymes, receptors, transcription factors, nucleic acids, lectins, and the like, where inhibition, activation, signal transduction, antagonists, and chemical reactions may be involved. Various protocols and different device structures may exemplify the subject devices.

In one exemplification of the use of the subject devices employing microtiter well plates, the microtiter well plate will have solutions which are to be analyzed, but lack one or more components necessary for the analysis. These solutions will usually be constituted to determine a binding event, interactions between two moieties, the presence of a particular moiety, and the like. The solutions in the wells may involve a single compound to be tested, a mixture of compounds including a test or control compound, or the like. Normally, there will be different compositions in different wells. The wells may involve heterogeneous binding, where a component of the determination method is bound to the surface of the wells and will be retained in the well. For example, in a specific binding assay, one may have receptors bound to the surface of the well and allow for a competition between a test compound and a labeled analog for binding to the receptor. After incubating the mixture in the well, the mixture is transferred to the microfluidic device zone and the label determined. Where the label is an enzyme, the liquid in the zone could include substrate for the enzyme, where the product of the substrate would provide a detectable signal. Alternatively, the label could be a fluorescer, where one would read the fluorescence in the zone. In both instances, the determination could be made in the absence of bound label.

There is also the opportunity to perform a heterogeneous assay in the zone. By having a non-diffusively bound entity, e.g., compound, cell, tissue, etc., for which the candidate and control compounds compete, where the bound entity is in limited amount, one can determine the activity of the candidate compound. By limited is intended that it is insufficient to bind more than about 75%, usually about 50%, of the total number of molecules of candidate and control. In carrying out the determination, the candidate or test compound and coritrol are added to the zone. The bound compound is in the zone, bound to any surface associated with the zone, including walls, which includes the walls of the zone enclosure and channel walls, particles and the like.

For example, one may coat the region surrounding the zone with an entity, e.g., cell, compound, etc., where the entity becomes bound in that region. The channel is then filled with a solution and the candidate compound and control compound added into the zone. The candidate and control compounds will compete for available binding sites of the bound entity. After sufficient time for reaction to occur, one may move the liquid in the zone. The system allows for the addition of very small volumes to a reaction mixture, where the dilution of the volume(s) may be controlled by the size of the zone. During the competitive binding reaction, the competitive compounds will be substantially retained in the region. Removal of the control compound and washing of the region is readily achieved by moving the liquid column in the channel, and one can readily detect the signal in the channel.

By coupling of the assay system with an electrokinesis system, where components can be separated, mixtures of candidates may be put into a well to bind to a bound receptor in the presence of a detectable binding compound. One could then transfer the various candidate compounds and control to the electrokinesis separation and determine whether any of the candidate compounds displaced the control compound. If it appears that at least one candidate compound has sufficient affinity for the receptor, the candidate compounds may be separated into bands and the bands analyzed, for example, by mass spectrometry. By knowing the mobility of the individual compounds, one can time when the band should be isolated and identified.

To enhance the surface area associated with the zone, one may have a wettable porous membrane between the channel and zone interface. The membrane may serve a number of functions, retaining particles in the zone, providing surface for binding entities, acting as a filter, and the like. Particles may be introduced into the zone and held in position by a variety of ways, through covalent or non-covalent bonding to the walls, barriers to movements, such as protrusions, cross-bars, magnetic particles, etc.

Instead of a heterogeneous system, namely a system requiring binding to a surface and a separation, one may use homogeneous assay protocols. Homogeneous assays may be exemplified by EMIT, FRET, LOCI, SLFIA, channeling assays, fluorescence protection assays, fluorescence polarization, reporter gene assays using whole cells, particle labels, etc., where enzyme, particle, fluorescer and chemiluminescer labels are employed. In these assays, one does not require a separation, since the binding event changes the level of observed signal. One would carry out the protocol in the same manner, but for the binding of the bound compound and the separation step, as the assay requiring the separation, where the liquid in the channel could provide one or more reagents required for the determination of the signal and/or provide a convenient site for detection of a signal.

In some instances one may wish to monitor the effect of a test compound on enzyme activity. In this situation one may add the test compound and enzyme to the zone comprising the channel solution, which provides the substrate. After sufficient time for reaction to occur, one may then determine the extent of the enzyme activity in the presence of the test compound.

Other assays of interest involve the effect of a test compound on the association of two other compounds, usually proteins, as members of a complex. These associations include transcription factors, cell surface receptors with other proteins, e.g. G-proteins, proteins binding to nucleic acids, e.g., DNA, lectins with sugars, subunit associations, etc. These assays may be carried out in substantially the same way as the heterogeneous assay, where one member of the complex is bound to the zone surface. However, in this case, instead of using a labeled member of the complex, the liquid in the channel could provide for an assay of the complex member. First, one would combine the candidate compound and the two members of the complex, either in a well or in a zone. The amount of complex formation and, therefore, amount of free uncomplexed members would be related to the effect of the candidate compound on complex formation. Once there has been sufficient time for complex formation, the determinations in each zone could be performed. By performing assays where a common liquid is used for all of the zones, one can perform a number of discrete steps. For example, since the complex member to be measured would be common to all of the assay determinations, one could provide for capture of the complex member in the channel portion of the zone, e.g. by having specific antibodies for the complex member. One could then wash out all of the channels using buffer, and then add a second solution comprising labeled specific antibody, which would bind to any of the complex member captured in the channel. With a fluorescent label, one could detect fluorescence. If one does not wish to capture the complex member, one may use several of the homogeneous assays and determine the level of the complex present in the zone.

One may use cells or compounds that are bound to the surface in the zone. These cells or compounds may serve a variety of functions, such as local buffering, production of agents to interact with agents in the zone, interacting with agents from the zone, production of detectable signals, etc. For example, by using polymers comprising buffering agents, the acidity or alkalinity of the solution in the zone may be controlled. Where a product is produced in the zone, which can bind to a surface membrane receptor of the cell and transduce a signal resulting in expression of a detectable product, the production of such product, may be monitored by the signal produced by the cell. Various compounds are known to bind to surface membrane receptors and transduce signals, such as steroids, hormones, interleukins, growth factors, etc., and biomimetric analogs thereof. By having a reaction in the zone that results in an active ligand, diffusion of the ligand to the cell, will result in the transduction of a signal. By having a regulatory region, e.g. promoter and/or enhancer, responsive to the transduced signal, where expression results in a detectable product, e.g. green fluorescent protein, an enzyme that catalyzes a detectable product, etc., one can monitor the rate at which the ligand is produced. Where one is screening for compounds, which activate or inhibit formation of the ligand, the production of the detectable signal would indicate the activity of a candidate compound.

With appropriate controls, one may take aliquots from the microtiter plate wells or other source of reaction components, so that one may obtain a plurality of determinations from a single mixture. In some situations, it may be feasible to control the volume transferred to the zone by using the detection systems described for determining the volume of liquid discharged from the channel. Alternatively, one may have detection systems in the zones. Other monitoring methods may also find use. One would then carry out an individual operation with a first microfluidic device, remove the device and replace it with a second fresh microfluidic device, and so on. When dealing with rare agents, such as test compounds, there would be minimal loss of the test compound during the operations and one could obtain a plurality of determinations concerning the test compound. One could directly move a test compound in a microtiter plate well from the well through an opening in the zone into the zone containing a reaction medium. After sufficient time for reaction to occur, one may then read a signal through the opening.

Of interest when measuring a signal is the presence of an orifice above the liquid in the channel, which allows for evaporation at the site of the determination, where the area in and optionally below the orifice serves as the zone. This zone may serve as an assay well, a reagent accepting well, a reaction vessel, etc. The solution of interest in the zone is bordered by liquid, so that the adjacent fluid acts as a reservoir for replenishing the liquid, which is lost by evaporation. This results in fluid flow toward the zone, which maintains the solutes in the zone, so that there is less diffusion away from the zone of the signal producing components during the time of measurement. By having a region associated with the zone of diminished area at which there is liquid exchange, diffusion is diminished, while liquid replenishment occurs. For example, in the case of a passageway through the wall of a capillary channel, which serves as at least a portion of the zone, the cross-section of the capillary channel is chosen to discourage significant diffusion from the region underneath the passageway, namely be less than the passageway cross-section. The reduction in the rate of diffusion of components from the zone allows for accurate rate determinations, since the change in signal will be substantially larger than the reduction in signal resulting from diffusion away of the signal-producing moiety.

Generally, one will have two entities interacting, where all or a portion of the two entities may be added to the well and any additional portion of the entities provided by the medium from the capillary. By referring to portion is intended only one entity or a portion of both entities, where the remaining amount of the two entities comes from the capillary. Since one will usually not wish to have any reaction between two entities involved in the operation prior to initiation of the reaction in the zone, normally at least one entity will be added to the zone immediately prior to initiating the reaction. However, in some instances where the operation cannot proceed except at an elevated temperature or in the absence of light, then the entities may be combined prior to addition or added at the same time.

The subject devices allow for a wide variety of applications. In one application, where the zone is at the terminus of the capillary channel, one may introduce a drop of a solution containing one or more components or reagents from a channel into the zone, prior, subsequent or concomitant with introducing a test component into the zone, where one is interested in the binding of the test component to a reagent in the liquid mixture. One would then withdraw the liquid in the zone into the channel, diminishing evaporation. The mixture could be incubated for a predetermined period of time. By providing that binding of the test component to the reagent results in a detectable signal, one can determine the binding of the test component to its target. For example, a reagent which is a complex of a protein target and a known ligand, where the protein is conjugated with quencher and the ligand with a fluorescer, release of the ligand will result in a fluorescent signal. By measuring the increase in fluorescence as a result of the test component binding to target protein and displacing the fluorescent ligand conjugate, one can determine the binding affinity of the test component to the target protein.

An alternative assay could use the opposed channels separated by a gap having a floor. In the gap one would bind different enzyme alleles at different spaces on the floor between each of the pairs of opposed channels. A solution of a compound would then be passed through the opening created by the gap and the mixture allowed to incubate, while in contact with the liquid in the channel. After sufficient time, a solution of the substrate would then be directed from the other channel into the gap to join with the liquid from the opposing channel. In this way substrate would be continuously supplied from the other channel. The turnover rate of the enzyme would be determined by detecting product in the gap, where the turnover rate would be constant, or increase with time. The rate would be related to the inhibitory effect of the compound and its binding affinity. For different alleles, one could have a single source or manifold of substrate solutions for supplying the individual channels where electroosmotic force could be used for pumping the substrate solution through the channels. This device allows one to rapidly determine the effect of a compound on different alleles. Rather than different alleles, one could have different enzymes and have different substrates in the different channels and any combination of related or unrelated entities.

In another method, one would have a continuous liquid column with opposed channels and gaps between the channels to define zones. Mixtures of enzymes and candidate and control compounds would be prepared and added to the zones, simultaneously or consecutively. After sufficient time of incubation, the liquids in the wells would be introduced to the zone. In the channels would be an appropriate substrate buffer solution. The solutions would mix with the buffer solution and evaporation would occur. The effect of the evaporation is to maintain the product narrowly confined to the zone as a result of liquid flow from the channels into the zone to replace the liquid lost by evaporation. By providing for production of a detectable product, one could determine the effect of the compounds on the enzymes.

In a further method, one would transfer a solution into an orifice, well or passageway in an otherwise enclosed channel into the zone and allow the solvent to evaporate. The solution would form a droplet on the surface of the channel and leave its components on the surface as a small spot. The components could be cells and a candidate compound for a cell surface receptor. The cells would adhere to the surface. Liquid would then be expressed from the channel into the zone, or a reservoir(s) filled to direct liquid into the zone, where the channel liquid introduced into the zone would have a ligand conjugate, for example, a fluorescent conjugate. After allowing sufficient time for the fluorescent conjugate to bind to any available receptor binding sites, the liquid would be withdrawn into the channel away from the zone and the fluorescence read. If liquid were necessary for the reading, a different liquid could be introduced into the zone through the orifice or from the reservoir. The binding of the candidate compound would be determined by the reduction in fluorescence in the zone. Where the well is an opening in a channel wall, substantially the same process could be performed without withdrawal of the liquid into the channel.

Obviously, there are too many operations which may be carried out, employing different diagnostic assay reagents, different targets and different protocols, to exemplify all of them, so that only a few have been illustrated as exemplary of the subject methodology.

The device may provide for heating and cooling of the zone. By varying the temperature of the channel, a large heat sink or source is provided for the zone. By having means for heating or cooling the fluid in the channel, one can modify the temperature of the zone, cycling the zone temperature in relation to the channel. To provide for more rapid variation in temperature, one may provide for heating and/or cooling solely in the zone, where once the source of thermal variation in the zone is terminated, the zone would rapidly equilibrate with the temperature of the channel. For example, in thermal cycling, one could use microwave heating, RF heating, laser heating, or the like, where the electromagnetic heating source is focused on the zone, so as primarily to change the temperature of the zone. In processes involving thermal cycling, such as the polymerase chain reaction, one would rapidly raise the temperature of the zone to 85–95° C., while maintaining the channel temperature at about 35–50° C. Once the DNA has been denatured, which would be a matter of not more than about 2 or 3 minutes, usually less, by removing the source of heat, the liquid in the zone would rapidly equilibrate with the temperature of the liquid in the channel. By appropriate selection of the temperature of the liquid in the channel, the temperature profile during the cycling may be controlled to provide the desired times for the different temperature stages of the cycle. .

The amplification may occur in solution or on beads, as in bridged amplification. See, for example, U.S. Pat. No. 5,641,658. By having the source of the DNA in the channels, all of the zones may include the same DNA or by providing different DNA indifferent channels, different zones may have different DNA. Conveniently, the channels may also provide the dNTPs and primers, or the dNTPs and primers may be added to the zones, as well as other components, e.g. ddNTPs. By adding the DNA polymerase to the zone through the orifice to the zone, the reaction may be initiated and cycled to amplify the DNA. After completion of the thermal cycling, the amplified DNA may be used for sequence determination, identification of particular sequences, using probes, snps may be identified or other characteristic of the amplified DNA may be identified.

Various protocols exist for identification of complex formation between a probe and target DNA, which may occur in the zone or as a result of analysis outside of the zone.

The subject systems may be used with many other ancillary systems to further enhance the flexibility and variety of operations for the system. One combination is with electrokinesis, where the zone would be part of a channel in which an electrical field is employed. By having reservoirs at opposite ends of the channel or using the zone as one reservoir, by applying an electrical field across the zone, charged species could be moved from the zone into the channel. Alternatively, one may use electroosmotic pumping to move the liquid in the zone to another site. By having crossed channels in the electrokinetic unit, components of the zone may be moved to an intersection and a defined volume injected into a second channel, where the defined volume may be subjected to different operations. The defined volume may be analyzed by electrophoretic separation, where the result of the operation in the zone is to have two or more detectable species having different mobilities in electrophoresis. One can provide for a detector along the second channel to identify the detectable species and quantitate the detectable species. Since one would be able to quantitate the initial and final agents, one would have a material balance.

In one embodiment, one has an assay system comprising the hydrophobic zone or well connected to one or more hydrophilic reservoirs through a hydrophilic channel, where the zone or channel, usually the channel, is connected to a side capillary channel for connection to an electrokinesis system, that is, providing for electrophoresis and/or electroosmosis. The two systems may be connected in the same substrate and be substantially in, the same plane of the substrate, where the size of the channels may differ in relation to their function. Thus, the capillaries of the electrokinesis system may be the same as or smaller than the capillaries of the assay system, and the reservoirs of the electrokinesis system may be the same, larger or smaller than the reservoirs of the assay system. The components of interest of the zone for analysis by the electrokinesis system will usually be charged, so that they can be transported by an electrical field from the assay zone to the electrokinesis system, where the components may be further processed, e.g. separated into bands, purified for further analysis, e.g. a mass spectrometer, etc. Conveniently, the side channel may be connected to an analytical channel, whose length will depend on the nature of the analysis and may be as short as 1 mm and as long as 50 cm, usually being between 2 mm and 10 cm. The channels of the electrokinesis system will terminate in reservoirs, usually serving as waste reservoirs or buffer reservoirs. It should be understood that the electrokinesis systems may take any configuration of any electrokinesis system as may be required for the particular procedure. The components of the zone may be moved to the intersection of the side channel with the analytical channel, where a waste channel terminating in a waste reservoir may be directly across from the side channel or offset from the side channel to form a double-tee. In either event, the components will be moved into and across the analytical channel by means of electrodes providing an electrical field between the zone and the waste reservoir. Once the desired composition of components is in the analytical channel, which may be a constant composition having the composition of the liquid in the zone, the electrical field may be changed so as to have the strongest field along the analytical channel, whereby the assay medium in the channel is injected away from the intersection toward the analytical waste reservoir. By providing for a medium in the analytical channel, such as a sieving medium, the assay mixture may be separated into components. Where the components provide a detectable signal, e.g. fluorescence, electrochemical, etc., a detector may be provided at an appropriate site along the analytical channel to detect the components as they move past the detector.

In many situations one may wish to separate constituents of an assay mixture. Where the substrate and product of an enzyme assay or chemical assay both provide the same signal, e.g. fluorescence, but have different mobilities, the substrate and product may be readily determined by using electrophoresis. Where multiplexed reactions are performed in the zone, one will have an interest in detecting the plurality of events that may have occurred. For example, one may have a plurality of reagents carrying electrophoretic tags (labels which have different mobilities in electrophoresis), where the result of the process in the zone is to release an electrophoretic tag in the presence of a target moiety. Where there may be a plurality of target moieties in the sample, the ability to detect the presence of the target moieties by the separation of released electrophoretic tags greatly enhances the simplicity with which the process may be carried out. Since the entire process may be automated, the addition of the assay components, the processing of the assay, the movement of the assay components into the electrokinesis system and the separation, confusion between samples is substantially eliminated, direct comparisons are achieved between samples and controls, component handling is minimized and more accurate results can be obtained.

The units may or may not have electrodes associated with each unit. Electrodes may be provided by painting electrically conductive wires on the surface of the card to be in contact with the solutions in the reservoirs or a "bed of nails" may be used, where a plurality of electrodes extend from the surface of a plate, each electrode associated with a unit having individually controlled voltage, and the electrodes may be introduced into the reservoirs or zones simultaneously. The entire system may be computer controlled, so that all or some of the steps may be automated. These steps include rinsing the system, additions of components, control of conditions, such as temperature, incubation time, movement of assay components and electrokinetic analysis, detection and analysis of results. The combination of systems finds use with homogeneous and heterogeneous immunoassays, chemical assays, high throughput screening of compounds, e.g. drugs, pesticides, etc., nucleic acids analyses, e.g. identification of sequences, sequencing, identification of snps, mutations, etc., and the like.

The zone may be combined with other devices for separation, analysis, etc. These devices may be HPLC columns, which may be miniaturized, connectors to gas chromatographic devices, mass spectrometric devices, spectrophotometers, fluorimeters, etc. By providing for pneumatic movement of the liquid in the zone to a channel, which directs the liquid to the other device, the liquid in the channel may be moved from the zone to the site where it may be analyzed. One can withdraw samples from individual zones, by employing reduced pressure above the zone, which will withdraw liquid from the zone into the device for analysis. One need only have a small pressure differential between the channel and above the liquid in the zone to have the liquid in the channel chase the liquid in the zone to a different site.

For the devices, large networks of channels may be produced in small integrated devices using a solid substrate, plate, block or film, commonly referred to as a card or chip, having one dimension ranging from about 5 mm to 10 cm and a second dimension ranging from about 5 mm to 50 cm, usually not more than about 20 cm, and preferably not more than about 10 cm, where the thickness may or may not be critical. In many cases, microstructures, such as channels and reservoirs may be formed in one substrate and the microstructures, enclosed as appropriate, with a cover or other substrate. The thickness of the device will depend on a number of factors, generally ranging from about 0.2 mm to about 5 mm, more usually from about 0.5 mm to about 2 mm. The thickness of the layers will determine, in part, the height of the ports and the dimensions of the channels, particularly channel height. Depending on the structures and protocols, there may be no orifice, the zone open to its environment being present in a gap or being in a part, channel or combination thereof. The part in the cover or base layer may have a depth as small as 1 $\mu$m and will usually be less than about 3 mm, generally being in the range of about 100 $\mu$m to 2.5 mm. Where there is a combination of a port or well and channel, desirably the port or well will have a height of at least about 0.1 mm, and may be 2.5 mm or more, usually less than about 1 mm. One may have as many individual units as space allows, desirably having at least about 12, more usually at least about 36 and up to 2,000 or more.

When having ports in channels, where the port comprises at least a portion of the zone, the chip will usually be comprised of at least two layers, a base layer comprising depressions or cavities, which may serve as channels, chambers, electrode contacts or connectors, and optionally ports to the depressions and cavities, and a cover layer, which encloses the depressions and cavities and may alternatively provide ports to the depressions and cavities. Additional layers may be present, laminated to the substrate, such as heat transfer layers, supports, casings, where films are used as the substrate and cover, and the like. The substrates may be flexible or rigid, usually not elastomeric, and may be composed of various materials, such as silicon, fused silica, glass, plastics, e.g. acrylates, polybornenes, polystyrenes, polydialkylsiloxanes, polycarbonates, polyesters, etc.

In FIG. 1, a fragment of a device is shown in perspective. The device 10 comprises a first layer substrate 12 of sufficient thickness to accommodate the features for the operation of the device 10. Sealed to the substrate 12 is base 14. Embodied in the substrate are units 16. Each of the units comprises a reservoir 18 in which contact electrode 20 extends from surface wire 22. The contact electrodes 20 and surface wires 22 may be wires, electrically conducting paint, or other means of electrical conduction. The surface wires 22 are connected to a controlled voltage source for providing an electric potential in accordance with a predetermined regimen. The reservoir 18 has port 24, for allowing communication with the atmosphere, and may be employed for introduction and removal of materials into and from the reservoir 18. Chamber 26 has port 28, where chamber 26 differs from reservoir 18 in its function, and will usually have different dimensions from reservoir 18. For the most part, the cross-section of the chamber 26 will be smaller than the cross-section of the reservoir, generally being smaller by at least about 10%, usually at least about 25%, and not more than about 90%, and larger than the cross-section of the capillary 36. Normally, there will not be an electrical connection in chamber 26, although an electrode may be employed for monitoring the presence and or amount of fluid in the chamber. Adding an additional wire to the device can be readily accomplished in the same manner as the electrical connections for the reservoirs 18. Not shown is an optical detector, which could be used for detection of the presence or amount of liquid in the reservoir 18. Reservoir 30 is substantially the same as reservoir 18 in having contact electrode 32 in electrical connection with surface wire 34. Reservoir 30 is optional, but may be present where greater versatility is desired in the device, rather than only a single chamber and a single reservoir per unit. Horizontal channel 36 provides fluid connection between the reservoirs 18 and 30 and the chamber 26. Finally, electrode 38 extends through substrate 12 into horizontal channel 36 and is connected to surface wire 40 for connection to a control device.

Depending on the manner of the use of the device, the surfaces of the various parts may vary, as to wettability and charge. For example, the upper portion of the inner wall 42 of the chamber 26 may be coated with a hydrophobic material to prevent aqueous media from rising up the wall. The region 44 in the channel 36 under the chamber 26 will be desirably wettable, so that aqueous solutions introduced into the chamber will wet the surface. Depending on what form of electrokinesis is used, electrophoresis or electroosmotic force (EOF), the surfaces of the channels will differ. For electrophoresis, it is desirable that the surface be neutral, while for EOF the surface should be charged, although by using an electrically charged water soluble polymer in the aqueous medium, where the charges are randomly distributed, neutral surfaces can be used. Charged surfaces may be achieved by using silicates, e.g. glass, charged coatings, covalently bonded or adhering, to the surfaces, or modifying neutral surfaces chemically to introduce charged species. Neutral species may be a variety of polymers, both addition and condensation polymers, particularly acrylates, although polystyrenes, polyolefins, etc. find use. Different regions may have different charge and functional characteristics. For example, a portion of a structural feature may be charged to permit EOF and another portion be neutral, where the charged portion is a conduit for movement of fluid under the urging of the EOF flow. During operation, there will be a fluid in at least one of reservoirs 18 and 30 and at least a portion of channel 36, and there may be fluid as well in chamber 26, where there would be a continuous or discontinuous stream in the unit.

Figures 1, 2A:
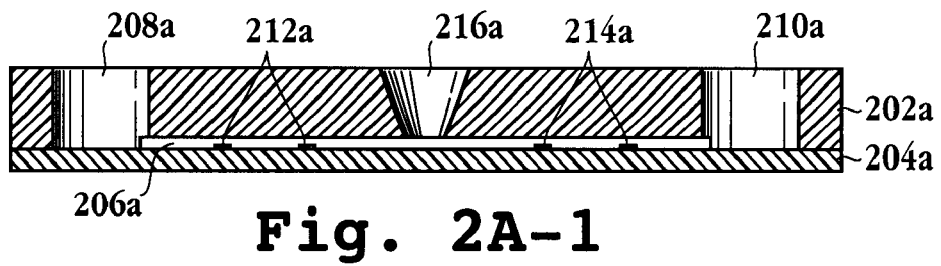
FIGS. 2A, 2B and 2C are diagrammatic cross-sectional views of units of a subject microfluidic device, having two channels and a central chamber, at various stages in the process of using the device.
Figure 2A:
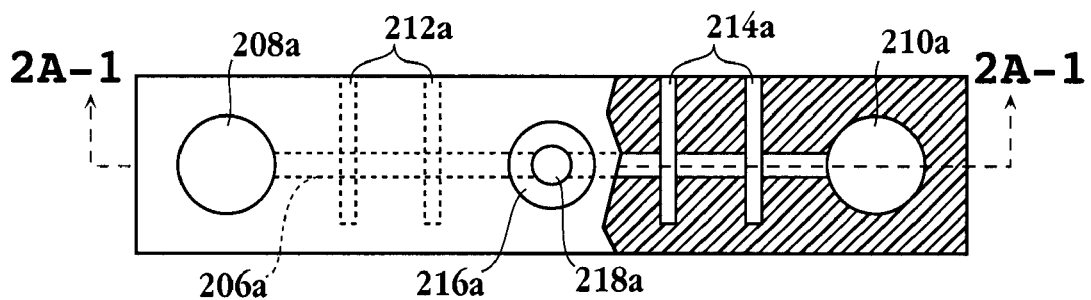
Figures 1, 2B:
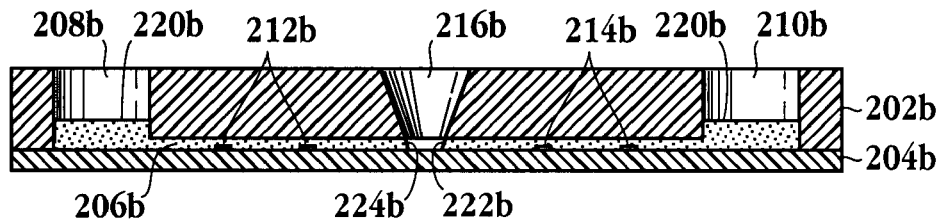
Figure 2B:
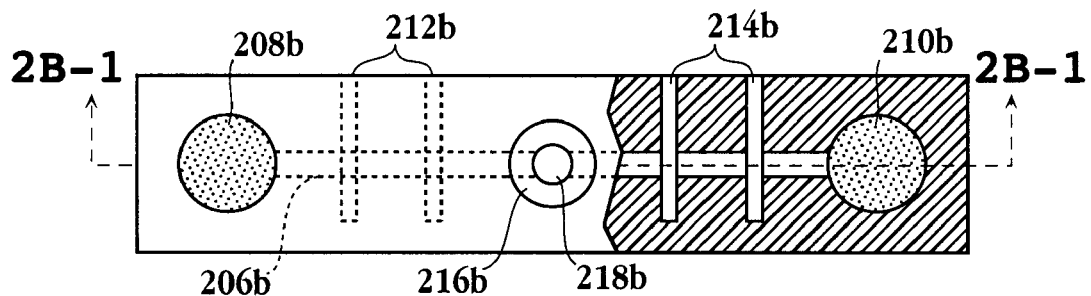
Figures 1, 2C:
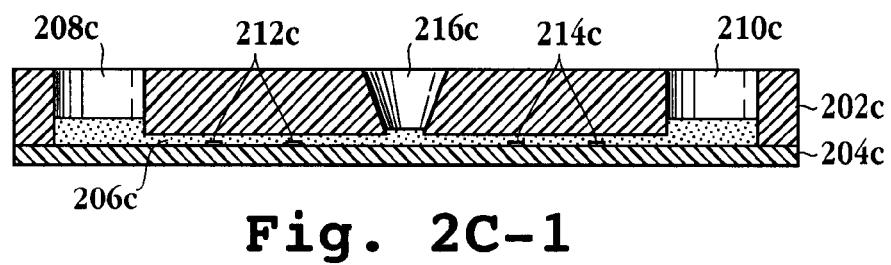
Figure 2C:
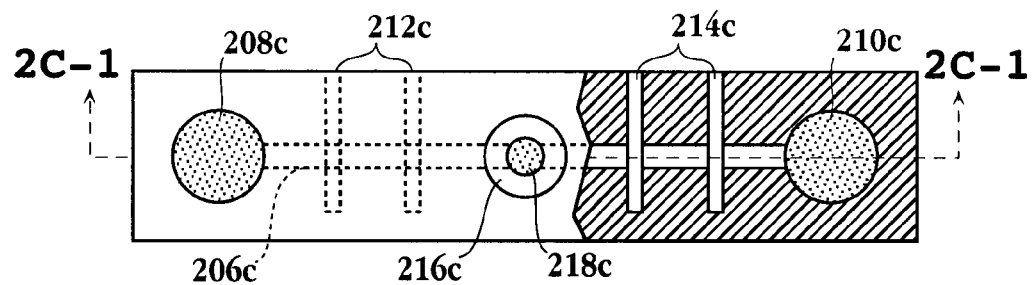

In FIGS. 2A, 2B and 2C, are depicted diagrammatic cross-sectional views of a unit in a device. The unit device 200a has substrate 202a, in which the various features of the unit device are present, and cover 204a. The unit comprises a channel 206a, which may be connected to a common manifold for receiving a medium common to all of the units. Each unit has two wells 208a and 210a, where either or both may serve as wells for introduction of fluids. Situated in the channel 206a are two sets of electrodes, 212a and 214a, where the electrodes may be painted onto or over 204a and chamber 216a all communicate with channel 206a. The surface 218a under chamber 216a, which is the surface of the cover 204a, is hydrophilic for acceptance of hydrophilic liquids. The unit is shown prior to introduction of any liquid.

In FIG. 2B, liquid 220b is introduced into the wells 208b and 210b. In the present configuration, the liquid is indicated as being the same, but with different protocols the liquid could be different. The liquid 220b from the wells 208b and 210b moves by capillary action into channel 206b and halts at chamber 216b, due to the absence of capillarity at the chamber 216b. A sample may then be added to chamber 216b, which will wet the surface 218b. Where the sample is small enough, it will not contact the inlet ports 222b and 224b of channel 206b. Depending upon the nature of the solvent added to the chamber 216b and the time interval in which the solvent is allowed to stand, all or a portion of the solvent may evaporate, so that upon total evaporation, only a solvent free liquid or solid will be present.

In FIG. 2C, contact is made between the material in the chamber 216c and the liquid 220c. Liquid 220c may be expressed into chamber 216c using one or both pairs of electrodes 212c and 214c, using EOF for moving the liquid 220c. As shown in FIG. 2C, the channel 206c is filled with the liquid 220c, so as to form a continuous stream of liquid. However, it is not necessary to have a continuous stream, and if desired, the stream may be discontinuous, where fluid is driven by only one set of electrodes and is stopped before making contact with the fluid in the channel 206c on the other side of the chamber 216c. In the latter situation, one may wish to withdraw the liquid from the chamber into the enclosed portion of channel 206c to inhibit evaporation of the solution.

Figure 3:
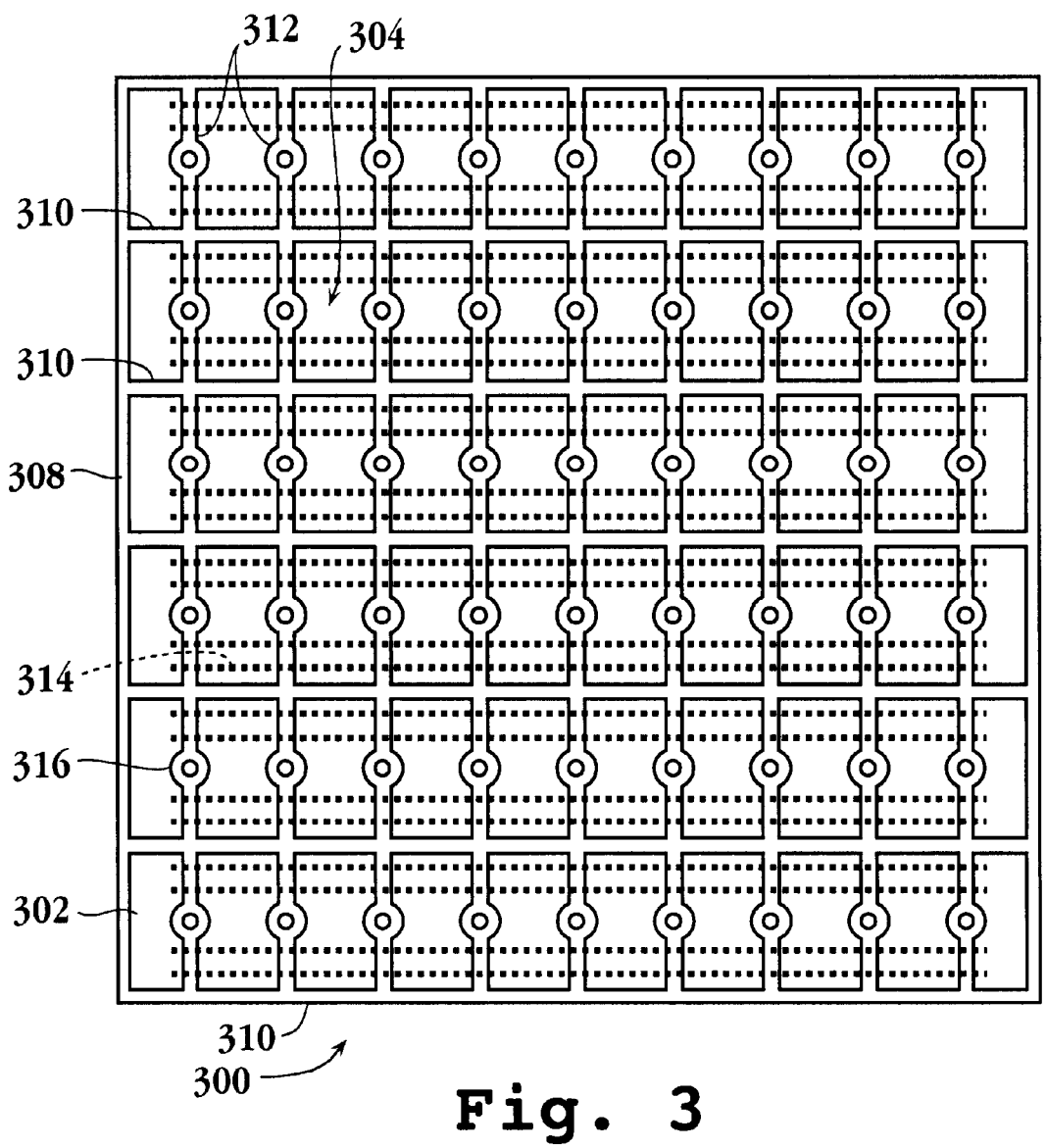
FIG. 3 is a diagrammatic plan view of a device with a plurality of units with fluid supplied by a manifold.

In FIG. 3, a diagrammatic plan view of a device is shown comprising a plurality of units and employing a common manifold for delivering liquid to the wells. This device is distinguished from the device depicted in FIG. 2 in having a common source of liquid, rather than allowing for different liquids to be available for different units. The device 300 comprises a substrate 302 and a cover 304, on which the substrate 302 is supported. The device has a common inlet port 306 and tributary channels 310. Each of the tributary channels 310 is connected to a plurality of side channels 312, which serve to provide liquid to chambers 316. Each side channel 312 is equipped with a pair of electrodes 314 for EOF pumping of liquid into and out of chambers 316. Liquid introduced into the inlet port 306 will move by capillary action through the channels 308, 310 and 312 to fill the manifold, but not enter the chambers 316. Different samples may be added by any convenient means to each of the chambers 316 and the sample may be further processed. Usually, with an aqueous sample there will be rapid evaporation. By using the pairs of electrodes 314 associated with one of the two side channels 312 associated with each of the chambers 316, a small volume of the liquid in the manifolds may be pumped into the chamber 316 to dilute the sample and then be rapidly withdrawn back into the side channel as a defined volume to allow for any incubation and inhibit further evaporation. The presence of the fluid in the channel in contact with the defined volume will replenish any of the solvent, which evaporates due to the presence of the inlet from the channel 312 into the chamber 316. In this way the composition of the defined volume will remain substantially constant in that the flow of solvent is into the defined volume and diffusion away of the larger components from the defined volume is discouraged. After sufficient time for any reaction to occur between the sample components and the components of the liquid, a reading may be taken of the defined volume in the channel or the defined volume may be pumped into the chamber 316 for taking the reading, to avoid having to read through the cover 304 composition. If one wishes to make a plurality of readings in the chamber 316, or even in the case where a single reading is made, the defined volume may be introduced into the chamber 316 and contact made with the liquid in the opposing side channel 312 Contact may be made by pumping the liquid from the opposing channel 312 into the chamber 316 or by adding enough volume from the channel containing the defined volume to bridge the floor of the chamber and join the fluid in the opposing channel 312.

The presence of the sample in the chamber in contact with the two side channels permits replenishment of liquid, which evaporates from the solution in the chamber. Diffusion of the components of interest is not significant, so that the loss of the components of interest in the zone is minimal and the signal from the solution in the chamber remains substantially constant over extended periods of time, particularly within the time frame of the usual measurements, generally under about 6 h, usually under 3 h. Since one is dealing with very small volumes, generally less than about 500 nl, substantial changes in composition could have an effect on the observed signal. For example, where one is interested in a binding affinity of a ligand to a receptor, a change in concentration of the ligand and/or receptor would affect the observed signal. Where one is interested in determining a rate, the problem is exacerbated, if during the assay, the concentration of all components of the solution are changing. Therefore, by permitting evaporation to occur in a zone of an assay mixture, while the zone is in contact with a solution which has substantially the same composition, except for one or few, usually not more than about 4, more usually not more than about 3, components, generally being the components of interest, many advantages ensue. Handling is easier, diffusion of the components having concentration gradients between the assay mixture and the liquid in the channel appears to be slower, and the solution can be read without the interference of the composition of the device. Generally, the liquid in the channel will be substantially the same liquid of the defined volume, except for the differing components of the sample introduced into the defined volume. Usually, the dilution factor of the sample in the zone will be in the range of about 0.1–10:1 during the course of the reaction.

Figure 4:
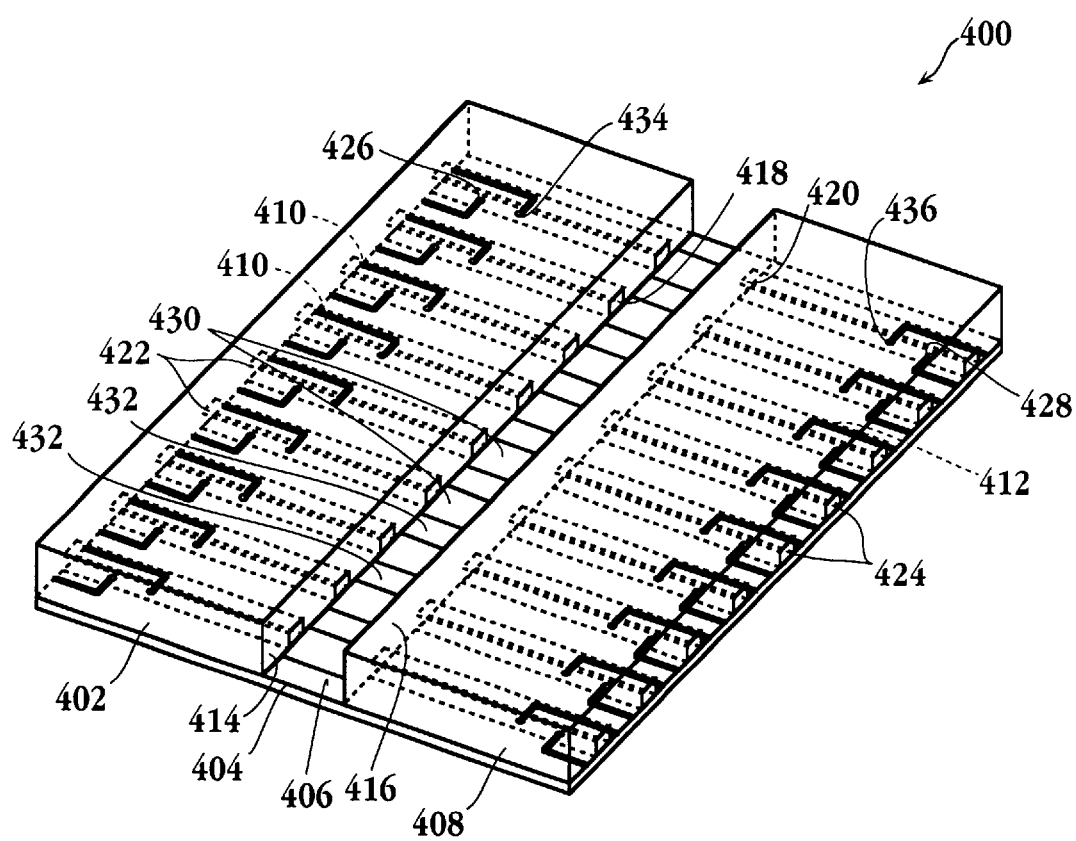
FIG. 4 is a fragmentary perspective view of an alternative embodiment of a microfluidic device with two channel blocks joined by a platform.

In a further embodiment, as depicted in FIG. 4, instead of having chambers isolated by walls, one has a platform between a plurality of capillary channels, where desirably each area between the channels on the platform is wettable and separated by a non-wettable zone. The device 400 has a first channel containing block 402, a platform 404, which may be open at its ends 406 and optionally, a second channel containing block 408, where the first and second channel blocks 402 and 408 are joined by the platform 404. The second channel-containing block is not necessary since all of the operations may be performed with a single channel containing block, although there are advantages in having a source of liquid on both sides of a droplet on the platform. Each of the channel containing blocks 402 and 408 have a plurality of channels 410 and 412, respectively. Each channel 410 and 412 terminates at a block face 414 and 416, respectively, which is non-wettable, with outlets 418 and 420, respectively, allowing for liquid communication with the platform. Each of the channels 410 and 412 has an orifice 422 and 424. Fitted near the respective orifices in the channels are electrodes 426 and 428. Conveniently, the area 430 of the platform between the channel outlets 418 and 420 is wettable, separated from the next wettable zone by a non-wettable band 432. Into each channel is extended a second electrode 434 and 436, which can be used for controlling flow of liquid in the channels in conjunction with electrodes 426 and 428, respectively.

The spacing between the blocks 402 and 408 will vary, depending on the protocol, the size of the sample volume, the size of the defined volume to be used for the reaction, the surface tension of the liquid, the contact angle of the liquid, and the like. The higher the surface tension, the smaller the gap. Usually, the spacing will be at least about 0.05 mm and not more than about 2 mm, usually not more than about 1 mm. The spacing will affect the volume of the reaction mixture and the volume of sample, which may be set down without contacting the channel outlets. Generally, volumes of sample will be not more than about 300 nl, usually not more than about 100 nl, with the minimum amount being controlled by the ability to transfer the volume. The spaces on the platforms may be coordinated with a microtiter well plate, so that the sample may be received from individual microtiter well plates at each hydrophilic site. The sample may be pre-prepared, combining some, but not all, of the reagents required for a determination. The remaining reagents necessary for the determination would be contained in the liquid in a channel or could be divided between the two opposing channels.

In carrying out a determination, one exemplary protocol is as follows: A sample is pre-prepared comprising a compound of interest and some but not all of the reagents required for a determination. While one could have all of the reagents necessary for the determination in the sample mixture, using the subject device solely for maintenance of a liquid medium, generally one will prevent a premature reaction by withholding a necessary reagent from the sample mixture; which is provided by the liquid in one or both channels. The samples are placed on the wettable sites 430 and, as appropriate, evaporation occurs. The walls of the capillaries 410 and 412 are appropriately charged or the medium contains an appropriate additive to support EOF pumping. Liquid is added to the capillary channels 410 through orifices 422 in sufficient amount to allow pumping of the liquid to extend a droplet from channel outlet 418 of sufficient volume to capture and dissolve the sample mixture in the droplet to form a defined volume. This is achieved by providing the appropriate polarity between electrodes 426 and 434, depending on the charge of the wall of the channel 410. While not necessary, it may be desirable to withdraw the defined volume through outlet 418 into channel 410 to substantially inhibit evaporation. As discussed previously, little, if any, significant diffusion occurs, so that the defined volume retains substantially the same composition. Withdrawal of the defined volume into the channel 410 can be achieved by reversing the polarity of the electrodes 426 and 434 that was employed when expressing the droplet. The defined volume may be retained in the channel for a sufficient time for a reaction to occur. Where the reaction is completed in the channel, the defined volume may be interrogated in accordance with the signal generated by the reaction. Alternatively, to avoid interference from the block 402 composition, the defined volume may be expressed onto the surface 430 and interrogated directly. If desired, fluid may be introduced into channels 412, in sufficient amount to extend to the outlet 420. The fluid in channel 412 may be expressed and withdrawn much in the manner of the fluid in channel 410.

In some situations, one may wish to incubate the defined volume in the channel 410 and then express the defined volume onto the platform 404 at site 430. The defined volume may then be separated from the liquid in channel 410 by mechanical action, introduction of a physical barrier, or the like, and the solvent allowed to evaporate. The liquid in channel 412 containing an additional reagent necessary for the determination may then be expressed and contacted with the assay mixture at site 430, the assay mixture dissolved in the liquid to form a second defined volume, which may then be read or withdrawn into channel 412 for incubation. As described previously, the defined volume may be interrogated in the channel 412 or expressed onto the site 430 and interrogated at that site.

Quite clearly, depending upon the protocol, less or more sophisticated devices may be used. By having two channel blocks, which can be independently operated, highly complex and sophisticated protocols may be performed.

Figure 5A:
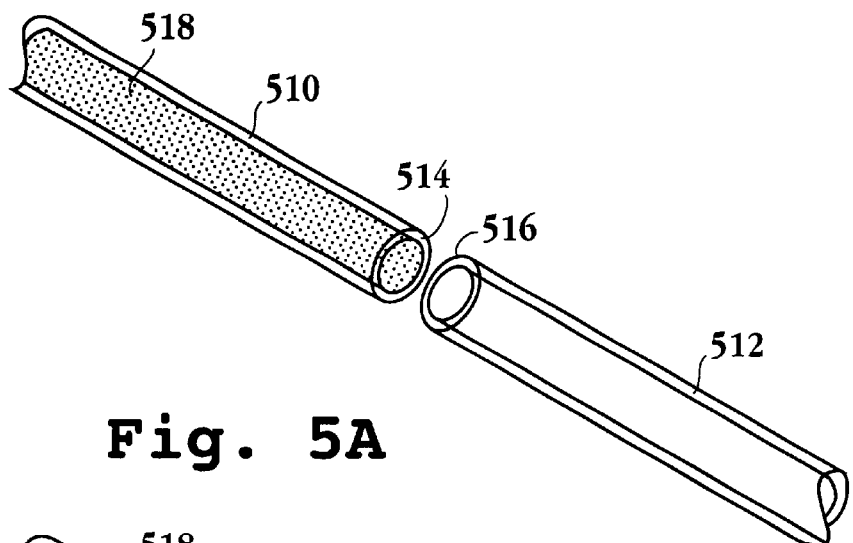
FIGS. 5A, 5B and 5C are perspective diagrammatic views of a device according to this invention employing two channels at different stages in their use.
Figure 5B:
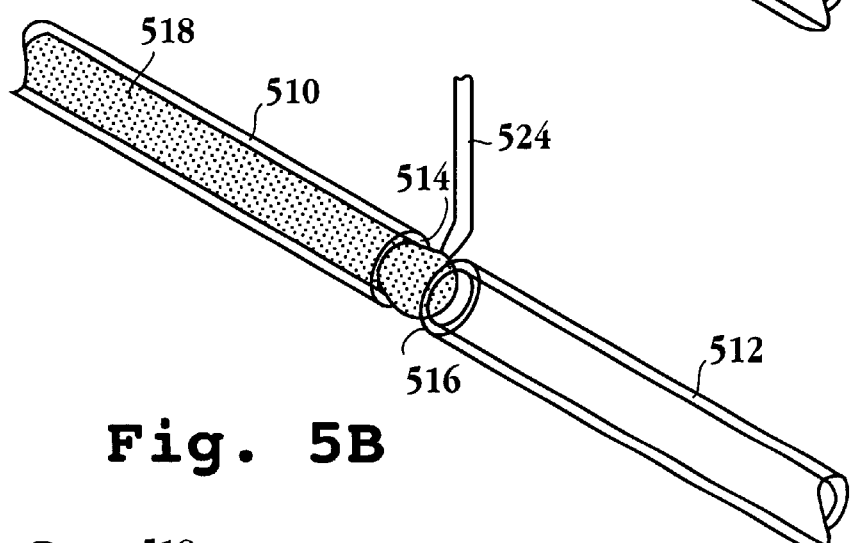
Figure 5C:
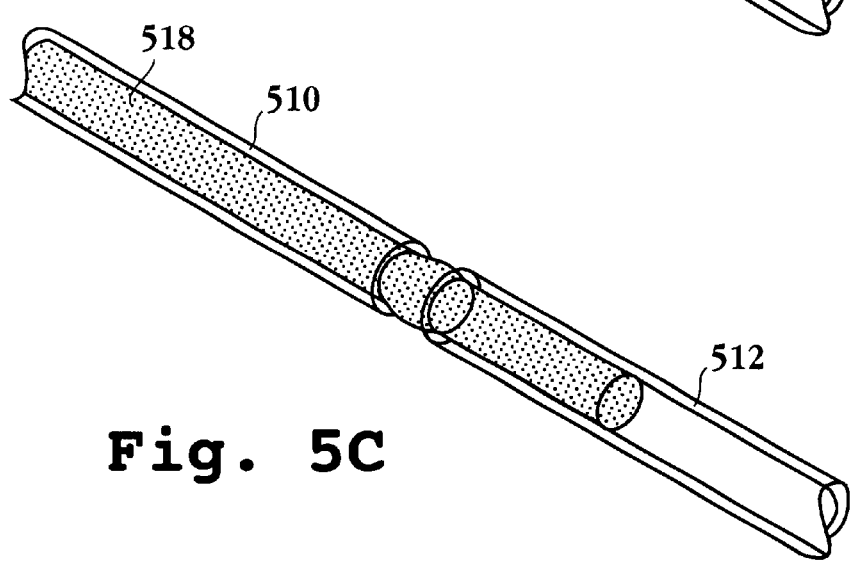

In FIG. 5, a simple structure is depicted of how two channels could be used in accordance with the subject invention. While only two channels are shown, it is understood that the two channels are only exemplary of a device having a plurality of channels, where blocks or plates are provided in which the channels are formed and main channels provided for carrying and removing liquid from the channels. Each channel in one block has a corresponding channel in the other block, which may be directly opposite or offset. The distance between the centers of the channel outlets will not exceed about 5 mm, where the distance between related channels will always be shorter than the distance to any other channel in the opposing block. As shown in FIG. 5A, a first channel 510 is positioned opposite a second channel 512. Channels 510 and 512 have channel outlets 514 and 516, respectively. In channel 510 is housed liquid 518. In FIG. 5B, a small droplet 520 of liquid 518 is discharged into the gap 522 between channel outlets 514 and 516. Movement of the liquid can be achieved with EOF, pneumatically or mechanical pumping. Micropipette 524 is used to transfer a small volume of liquid to the droplet 520 to form a reaction mixture. After the addition of the liquid to the droplet 520, the liquid 518 in channel 510 is pumped to cross the gap 522 and enter channel 512, where the droplet 520 comprising the reaction mixture is contained within channel 512. If one wishes, one could have prefilled channel 512, so that there would be a continuous column of liquid extending through the channels and the droplet 520 would be protected from any evaporation. As shown in the figure, only a small amount of evaporation can occur, due to the very limited interface between the liquid and the atmosphere in the channel. After incubating the reaction mixture, the occurrence of a reaction can be determined, where the reaction provides for a detectable signal. The determination may be made while the reaction mixture is in the channel, or the reaction mixture may be expressed and the signal read without interference from the material forming the channel. Alternatively, by moving the droplet 520 into the gap 522, all or a portion of the liquid in the gap 522 could be isolated with the pipette 524 and the reaction mixture analyzed.

Figure 6A:
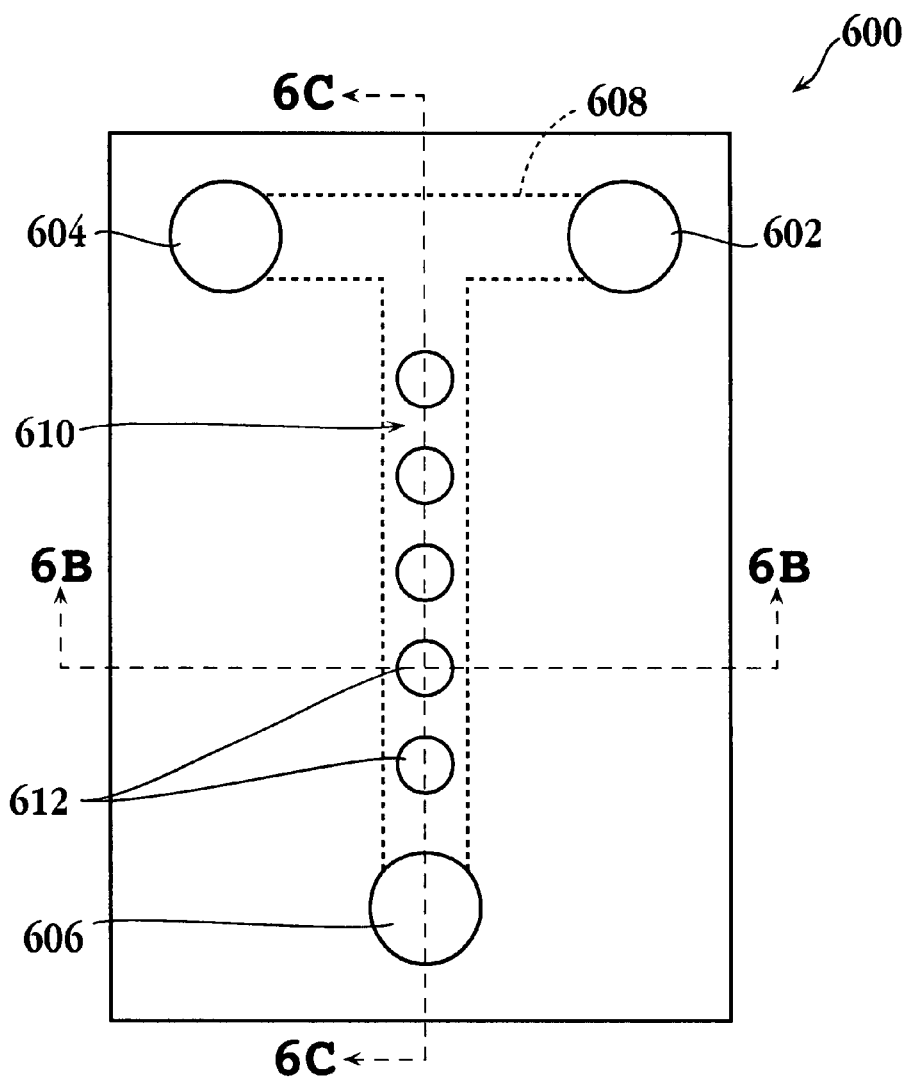
FIG. 6A is a plan diagrammatic view of a device according to this invention, with FIG. 6B a cross-sectional view along line B—B and FIG. 6C a cross-sectional view along line C—C.
Figure 6B:
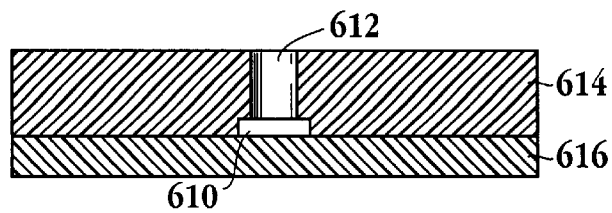
Figure 6C:
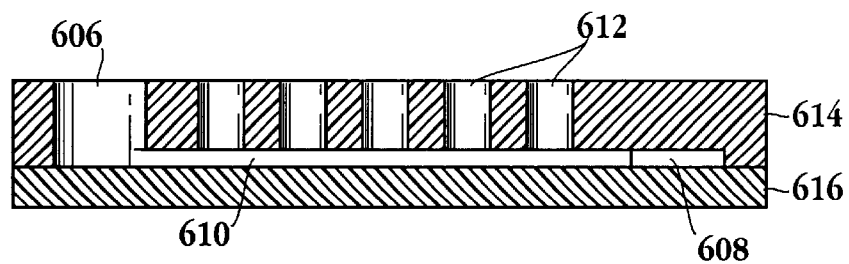

In FIGS. 6A, 6B and 6C, a device 600 is depicted with three reservoirs 602, 604 and 606, where reservoirs 602 and 604 are connected through auxiliary channel 608 and through auxiliary channel 608 to main channel 610. Reservoir 606 is at the terminus of main channel 610 opposite to the terminus of main channel 610 joined to auxiliary channel 608. Above main channel 610 are a plurality of ports 612 aligned and evenly spaced along the main channel 610, extending through the upper layer 614. Channel 610 is enclosed at its bottom by lower layer 616. While in the figure, the channel 610 is shown as having a greater width than the diameter of the port 612, this can be reversed, where the channel would have a smaller dimension than the port, and the width of the channel would control the size of the interface between the port and the channel. The effect of having a smaller channel width than the width of the port is to have a portion of the droplet in the port supported by the lower layer and out of contact with the, liquid in the channel. Furthermore, smaller channels will enhance the linear velocity in the liquid for comparable levels of evaporation in the port. In using the device, an aqueous medium is introduced into the reservoirs so as to fill the channels. By having the port walls non-wettable, the aqueous medium does not rise up the walls, but forms a small convex meniscus. Solutions may be added to each of the ports and reactions performed at each port site. Preferably, there would be only one port along a channel, where there could be many main channels, each with a single port.

It should be understood that the level of the liquid in the reservoir may be the same, higher or lower than the level of the meniscus. While preferably the level will be higher, the salient consideration is that the surface tension in the well is sufficient to support the meniscus. Therefore, as long as the liquid in the zone is maintained at a substantially fixed level during the operation despite evaporation from the zone, the level of the liquid in the reservoir is not critical.

Figure 7A:
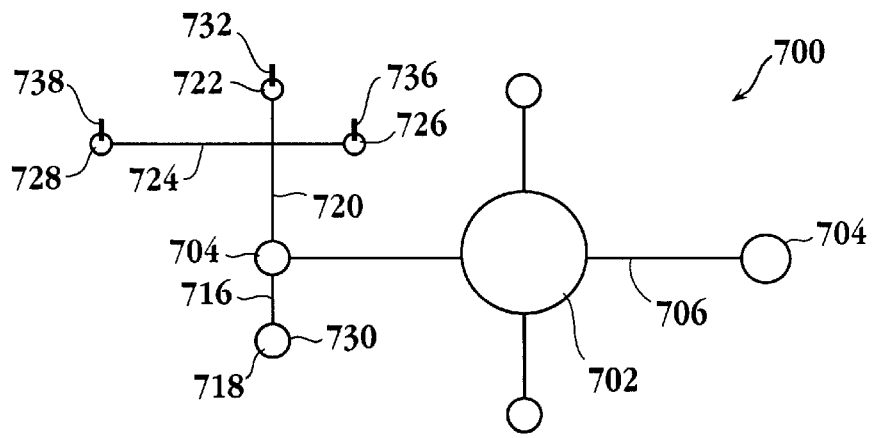
FIG. 7A is a diagrammatic plan view of a network according to this invention.
Figure 7B:
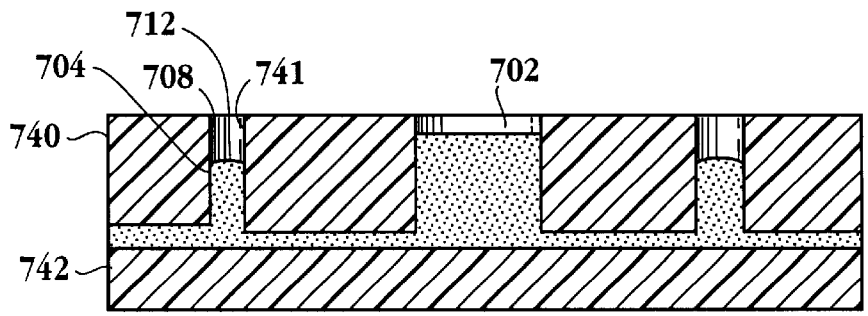
FIG. 7B is a cross-sectional view of a device corresponding to a portion of the network of FIG. 7A.

In FIGS. 7A and 7B, diagrammatic plan and cross-sectional views are depicted of a unit with electrokinesis capability for analyzing the components in the zone, while having a central distribution of reagent components from a reservoir to a plurality of zones. The unit 700 comprises a central reservoir 702, which serves to receive a solution of one or more reagents and act as a distribution center for distributing the solution to a plurality of zone enclosures 704 by means of channels 706. The solution in the central reservoir 702 is conveniently maintained at a level above the liquid level in the zone enclosure. In this situation a solution of the reagent is added to a dry central reservoir under conditions that retain the solution in the central reservoir. After adding buffer or other diluent, the solution from the central reservoir is released into the channels and to the zones. The solution migrates from the reservoir 702 through the channels 706 and enters the zone enclosure 704. Where liquid is present in the zone enclosure 704, the solution will mix with the liquid in the zone enclosure 704 to provide a reaction mixture. The zone enclosure 704 comprises an upper region 708 of the zone enclosure 704, into which the reaction mixture extends, having meniscus 712, from which liquid evaporates. The zone enclosure 704 is connected by channel 716 to a buffer reservoir 718 and by channel 720 to waste reservoir 722. Thus, buffer reservoir 718, channel 716, zone enclosure 704, channel 720 to waste reservoir 722 define an electrokinetic channel, whereby charged components may be moved by electrophoresis and both charged and uncharged components by electroosmotic force. The channel 720 crosses channel 724, which can serve as an analytical channel. For example, it may contain a sieving polymer to separate components of different mobilities, such as proteins and protein complexes, DNA of different lengths, etc. The analytical channel 724 connects buffer reservoir 726 and waste reservoir 728. Each of the reservoirs has electrodes, where the buffer reservoir 718 has electrode 730, the complementary waste reservoir 722, electrode 732, the buffer reservoir 726, electrode 736 and the complementary waste reservoir 728, electrode 738.

The device has an upper plate 740 and a lower plate 742. The lower plate 742 has channels 716 and 720, which connect buffer reservoir 718 and waste reservoir 722 with zone enclosure 704, where the channel provides solution under the upper portion of the zone enclosure 712 with liquid from the channels 716 and 720. While the diameters and the reservoirs are shown as approximately equal in FIG. 7B, this is for illustration. In practice, the zone enclosure diameter would normally not be greater, usually smaller than the reservoir diameters. In this case, by having a non-wettable wall 716 in the zone enclosure 708, a convex meniscus 712 is observed and the height to which the liquid in the zone can rise is restricted.

While not necessary to fabricate the device of two plates, the use of two plates will be of great convenience. The appropriate channels may be formed in each of the plates, independently of the other. The openings for the zones and reservoirs in the upper plate 740 may be formed to be in register with the corresponding portions of the microstructures present in the lower plate 742, while the channels in the upper plate 740 may be made independent of the microstructures in the lower plate 742. In this way a network of channels and reservoirs may be formed in the lower plate and access to these channels and reservoirs provided in the upper plate.

In carrying out an operation, the channels in the lower plate may be filled with buffer, where different buffers may be present in different channels. The buffer may contain one or more reagents and or the sample, depending upon the nature of the operation. If one wished to carry out enzyme assays, where the enzyme is an expensive reagent, one could, have the enzyme provided from the central reservoir 702. One could fill the channels with buffer and enzyme substrate. The liquid from the channels will rise into the zone enclosures 704 to form a meniscus 712 and define the reaction mixture. If one is interested in the effect of a test compound on the activity of the enzyme, one could add a different test compound to each zone. One would then add the enzyme solution to the central reservoir 702, whereby the enzyme solution would move by capillary action through channels 706 to zone enclosures 704. Liquid moving from zone enclosures 704 into channels 706 may be prevented in a variety of ways, including maintaining reservoir 702 sealed until the enzyme solution is added, providing a barrier at the interface between channel 706 and central reservoir 702, which is dissolved by the solution added to central reservoir 702, and the like. Once the enzyme enters the zone enclosure 704 the enzymatic reaction will occur and product will begin to be formed. After sufficient time for product to form, the electrokinetic analysis may begin. The electrodes 730 in buffer reservoir 718 and 732 and in waste reservoir 722 are activated to begin the migration of charged species from the liquid in the zone enclosure 704 toward the waste reservoir 722. When the enzyme product reaches the intersection 746 between channel 720 and channel 724, the defined volume of product is injected into the analysis channel 724, by using electrodes 736 and 738. The product may then be separated from other components in the reaction mixture and read. Where the product is fluorescent, the product may be read with a PMT or CCD or other detection device.

In analogous manner, one could perform DNA sequencing, where the DNA sample would be put in the central reservoir, dNTPs and labeled ddNTPs in the buffer and different primers in the different zones. One would then add the polymerase to the different zones and initiate the extensions, with thermal cycling in the zones. Once the sequencing was completed, the electrophoretic analysis could begin, where the DNA fragments could be directed to the intersection 746 and the channel 724 would contain sieving buffer, to provide separation of the different length fragments.

Figure 8A:
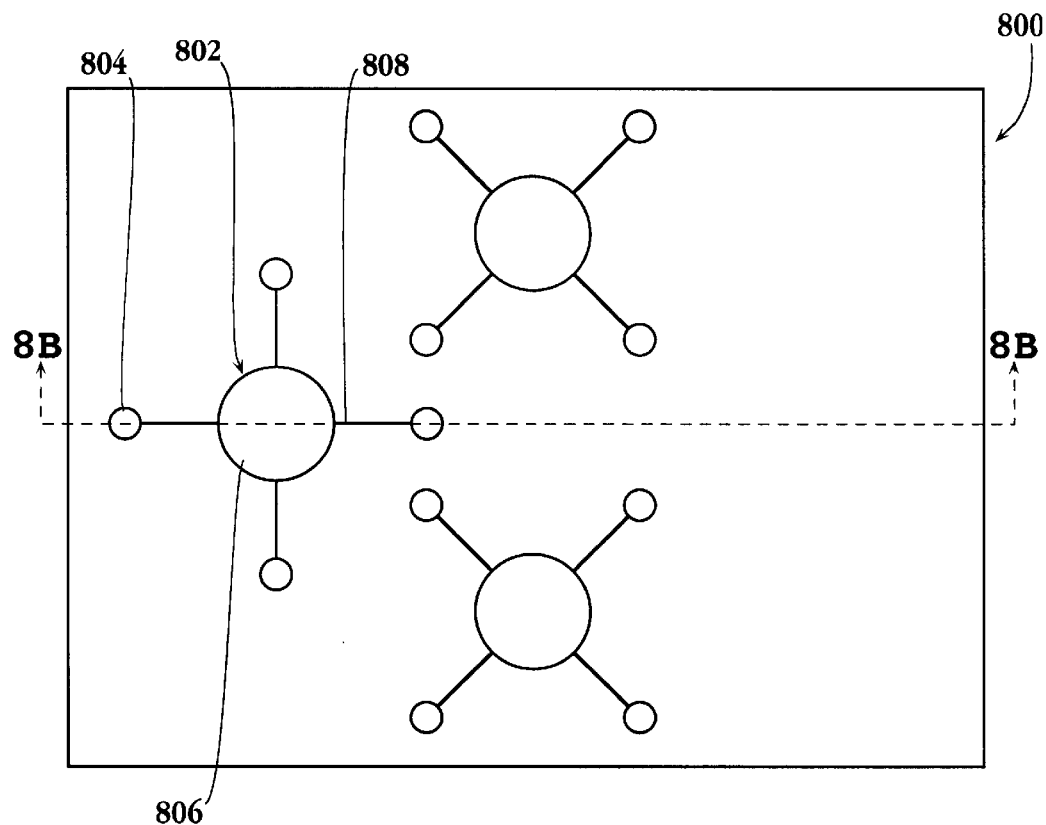
FIG. 8A is a diagrammatic plan view of a network according to this invention.
Figure 8B:
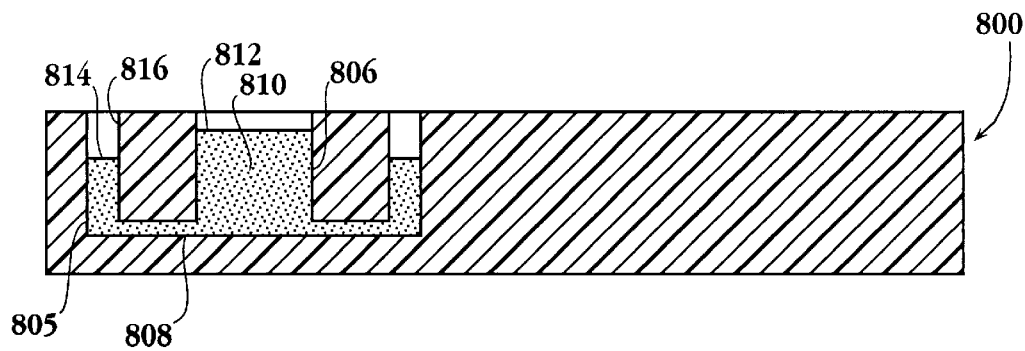
FIG. 8B is a cross-sectional view of a device corresponding to a portion of the network of FIG. 8A.

In FIG. 8 a different arrangement is provided, where the partially enclosed zone has only a single channel connection and a central reservoir for replenishing the volatile liquid in a plurality of zones. The plan view of the device 800 shows three units 802, although there would normally be many more, where the units would be distributed to provide for high density of the units 802. For clarity, each unit is shown to have only four vessels 804, although in a commercial device there would be a much greater number of vessels connected to each reservoir 806. The reservoir 806 is connected through channels 808 to the vessels, 804. The reservoir 806 would normally be filled with an appropriate liquid 810 to provide liquid for replenishment of liquid evaporating from the liquid 805 in the vessels 804. The height 812 of the liquid in the reservoir, 810 would provide a hydrostatic head, which would be insufficient to drive the meniscus 814 of the liquid 805 past the non-wettable region 816 in the vessel 804. For example, if one were dealing with an aqueous medium there would be a a region 816 in the vessel 804, which would be non-wettable. This would result in the aqueous medium rising in the vessel 804 to the non-wettable region 816, where a convex meniscus 814 is formed. The surface tension of the meniscus 814 prevents the liquid in the vessel 804 from rising beyond the wettable portion of the wall of the vessel 804. The result is that as the liquid 805 in the vessel 804 evaporates, liquid from the reservoir 806 will replenish the liquid 805, so as to substantially maintain the volume of the liquid in the vessel 804. Furthermore, the movement of the liquid in the channel 808 is in the direction toward the vessel 804, so as to diminish diffusion of solutes in the liquid 805 toward the channel 808.

In carrying out operations in the liquid 805, one can have very small reaction volumes, which are maintained during the course of the reaction, regardless of whether the vessel 804 is covered or uncovered. Furthermore, during additions of solutes, where the vessel is open to the atmosphere, the inevitable evaporation of a volatile solvent is compensated by liquid from the channel, so as to maintain the volume of liquid 805 substantially constant.

Figure 9:
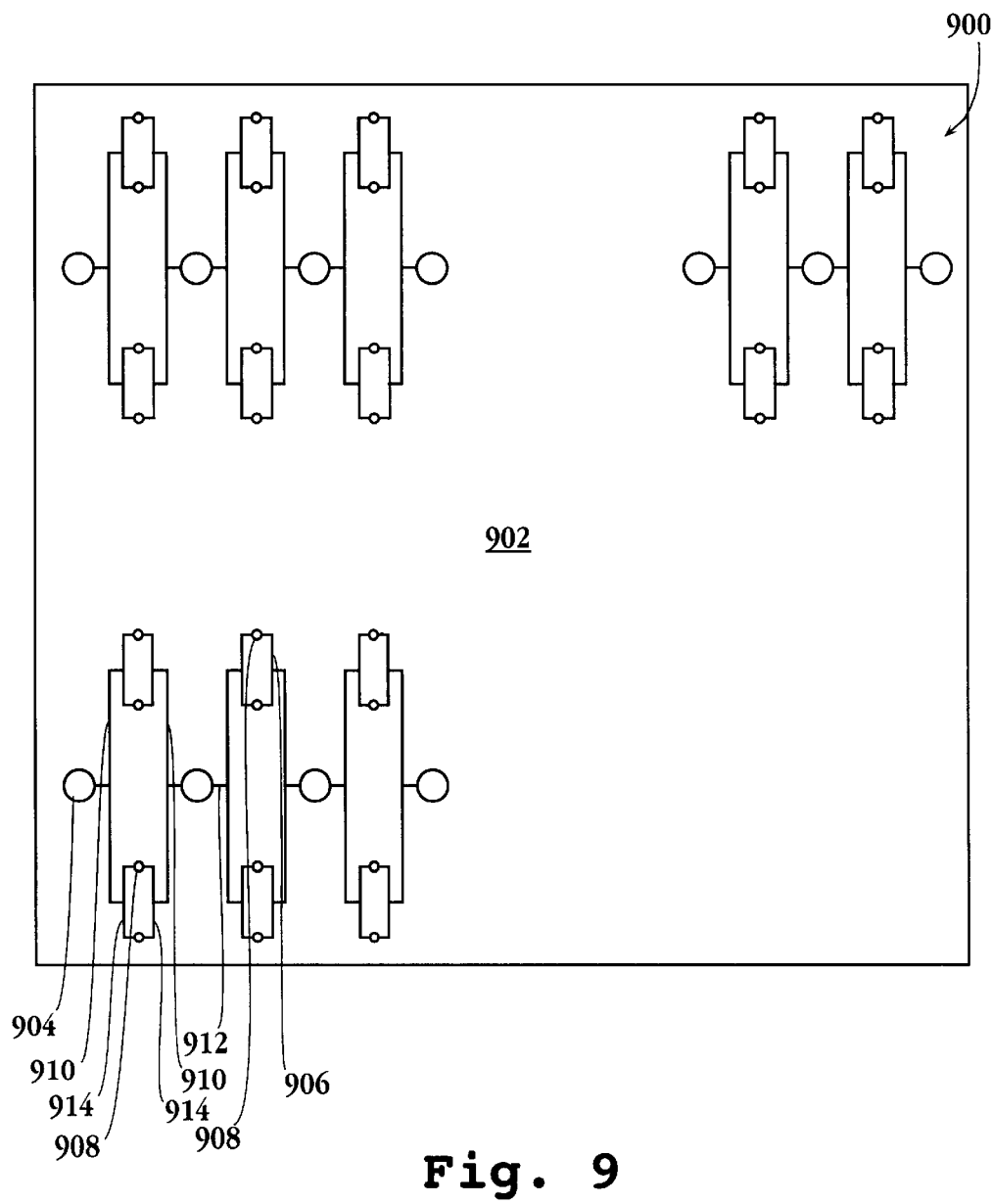
FIG. 9 is a diagrammatic plan view of an assembly of device units according to this invention having common channels along a row of device units.

In FIG. 9 is shown a diagrammatic array of a plurality of units having common channels and reservoirs in a row. The device 900 is designed to have the same distribution of zones as for a 96-well microtiter plate. The plate 902 has reservoirs 904 positioned between units 906. Each unit 906 comprises zone chambers 908 and parallel distribution channels 910, which channels are fed by reservoir connecting channels 912. Feeding channels 914 connect the distribution channels to the zone chambers 908. One would carry out determinations by filling all of the channels with the appropriate liquid buffer, where meniscuses would form in the zone chambers 908. One could fit the device to be under a microtiter well plate, where the wells had fritted disk bottoms, so that the wells are in register with the zone chambers 908. By pressurizing the wells, liquid in the wells would be driven into the zone chambers 908 and mix with the liquid in the meniscus in each of the zone chambers 908. The reaction mixtures may then be incubated and the results determined by interrogating each of the zone chambers 908.

Figure 10:
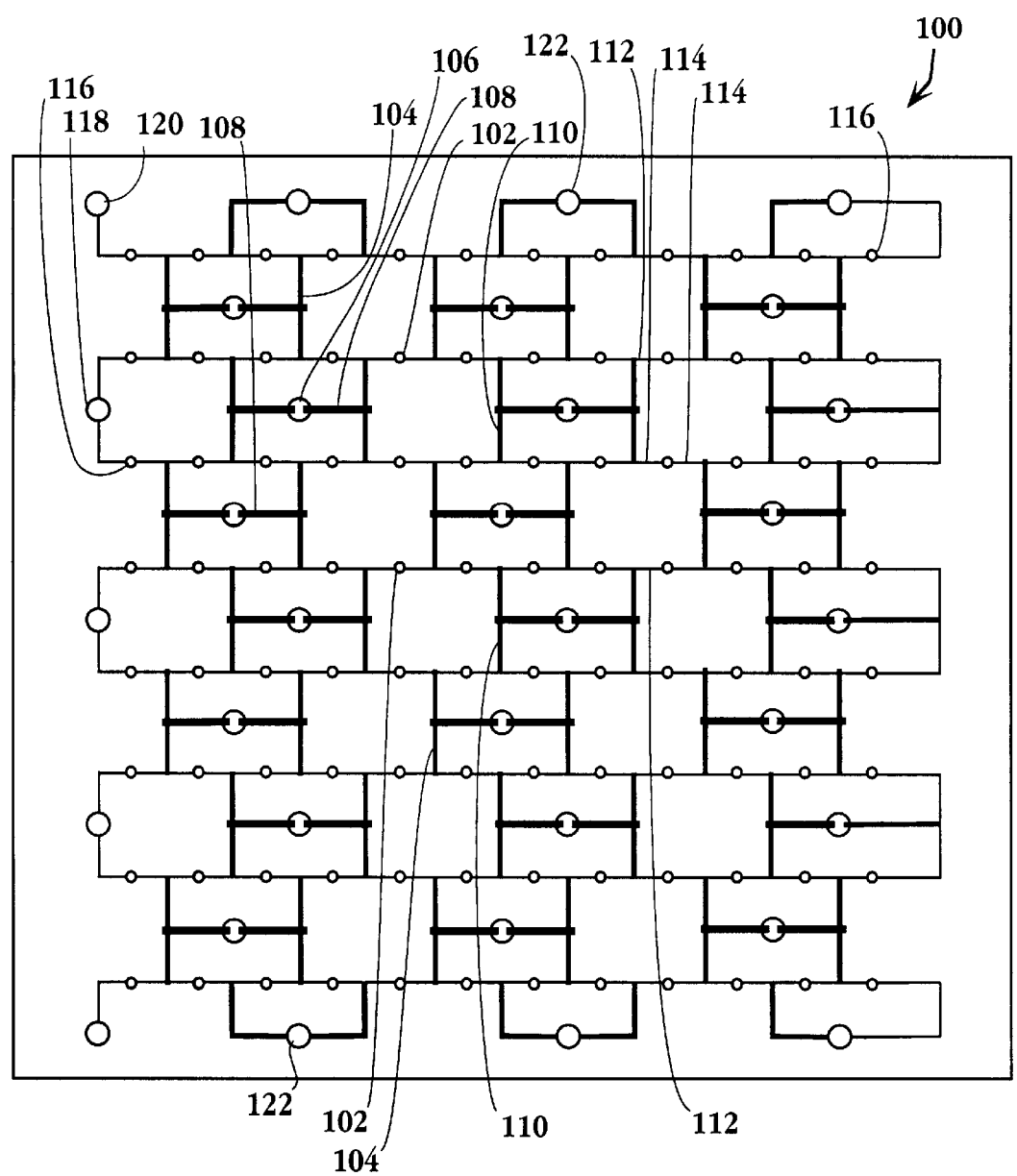
FIG. 10 is a diagrammatic plan view of an assembly of device units with a common assay well channel and shared reservoirs.

In FIG. 10, a diagrammatic array of an alternative embodiment of a plurality of units in a microfluidic device having common channels and reservoirs is depicted. The device a100 is designed to have the same distribution of zones a102 as for a 96 well plate. Internal reservoir units a104 are symmetrical about the reservoir a106, which is connected by parallel channels a108 to orthogonal channels a110. The zones a102, which are internal to the device (not on the periphery or along the outer channels) are organized so as to be equally spaced apart along the distribution channels a112. The distribution channels a112 maybe the same as or smaller in cross-sectional area than the parallel channel a108 and/or the orthogonal channels a110. Each zone a102 is connected on both sides of the zone a102 through a segment a114 to an orthogonal channel a110. In this way, each of the zones is symmetrically situated and is fed by two different reservoirs a106. The outer zones a116 are positioned somewhat differently, since the terminal reservoirs a118 connect two of the distribution channels a112, except for the corner reservoirs a120, which are connected to only one distribution channel a112. In addition, the top and bottom reservoirs a122, instead of feeding two distribution channels a112, feed into only one. The organization of the device a100 provides many economies, while at the same time providing greater flexibilities. By having each zone receiving fluid from two different reservoirs and each reservoir feeding four different zones, one can provide for different components in the reservoirs between alternating distribution channels a112, so as to provide greater diversity of reaction components. The organization further provides for substantially equal movement of fluid to each of the zones and allows for hydraulic equalization, so that all of the reservoirs may be equilibrated to the same height before initiating any reaction. The reservoirs and channels may be filled using pressure or allowed to fill by capillary action. If different components are to be introduced into reservoirs in different rows, one could initially fill the device with a common buffer and then add the different components to the different reservoirs, where diffusion and liquid flow would carry the components to the zones.

Figure 11:
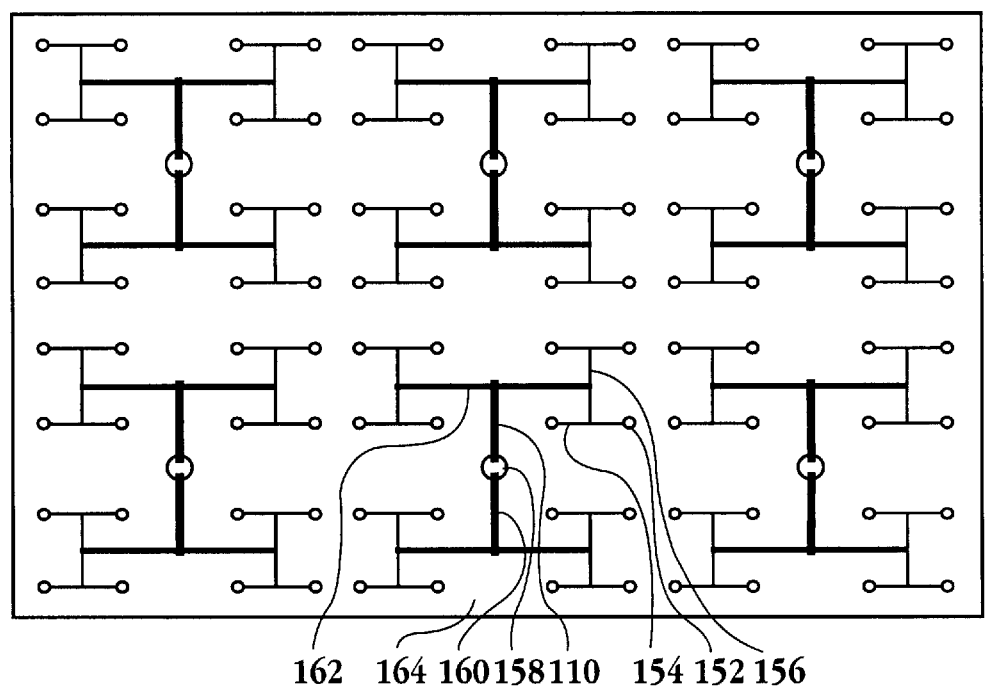
FIG. 11 is a diagrammatic plan view of an assembly of devices with a plurality of units, each unit having a plurality of assay wells sharing a common reservoir, with the assay wells on a 96-well microliter plate footprint.

In FIG. 11 the diagrammatic array of a plurality of units employs a different organization. In this array, device a150 has as in previous organizations the footprint of a 96 microtiter well plate. The device has 6 units a164. There are a few significant differences from the other devices in that zones a152 do not have two channels feeding the zone a152, but rather a single feeding channel a154. A distribution channel a156 is connected to two feeding channels a154, where each feeding channel a154 provides liquid to two zones a152, so that a single distribution channel a156 serves four zones a152. The distribution channels a156 are symmetrically situated about reservoir a158, where 16 zones a152 are fed from the reservoir a158 through main conduits a160 and cross conduits a162.

In each unit a164, the zones a152 are, symmetrically situated, so that the channel distance from the reservoir a158 through the main conduits a160, the cross conduits a162, the distribution channels a156 and the feeding channels a154 are substantially the same distance from the reservoir a158. The fluid head in the reservoir a158 and the resistance to flow through the flowpath of the liquid through the channels to the zones a152 will be substantially the same for each zone a152. In this way, the only difference between the state of the zones will be based on any difference in components added to an individual zone. In addition, one could use one zone as a control, so that for each unit a164, the other zones would have substantially the same conditions as the control, providing for a more accurate comparison of the results of the controls and samples.

Figure 12:
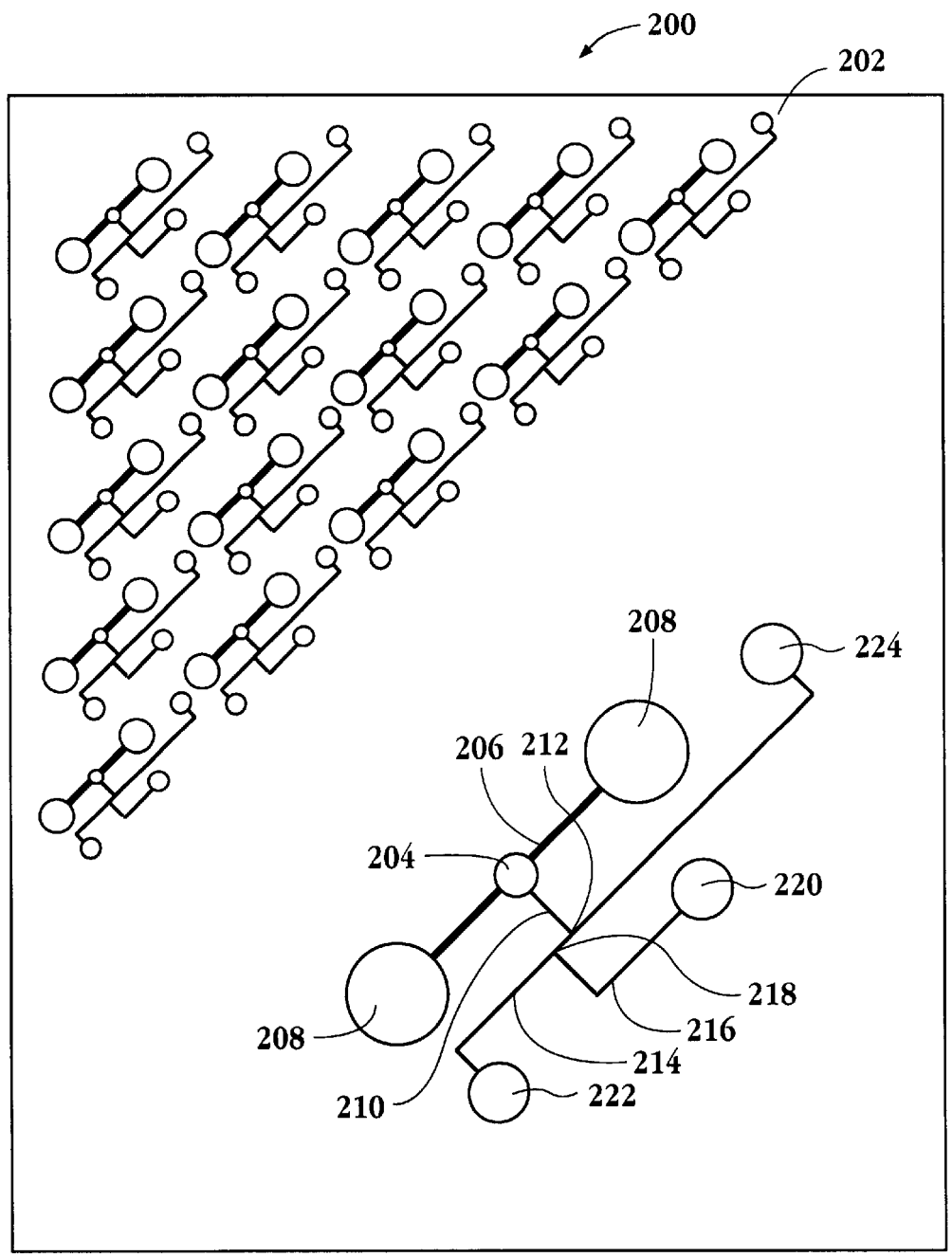
FIG. 12 is a diagrammatic plan view of individual units comprising a combination of an assay system joined to an electrokinesis system, with an exploded view of one of the units.

In FIG. 12, the diagrammatic plan view is of a device a200, which combines the advantages of evaporative control with electrokinesis. The units a202 have zones with the same footprint as a 96 microtiter well plate. Each unit a202 has a zone a204, which is connected by connecting channels a206 to reservoirs a208. This portion of the unit a202 has substantially the same purpose and manner of use as the other evaporative control units that have been previously described. In this embodiment the connecting channels a206, that connect under and to the zone a204 are connected at a tee to a side channel a210. The side channel a210 serves to connect the zone a204 with an electrokinesis network at the intersection a212 with analysis channel a214. While the configuration shown is a double-tee configuration, where waste channel a216 connects to analysis channel a214 at intersection a218, one could have a cross-intersection, where the two channels a210 and a216 meet at the same site of analysis channel a214. Waste channel a216 terminates in waste reservoir a220. Analysis channel a214 terminates at one end in buffer reservoir a222 and at the other end in waste reservoir a224. In operation, there would be electrodes in the two waste reservoirs a220 and a224, the buffer reservoir a222 and in at least one of the zone a204 or the reservoir a208.

In operation, one would first carry out a reaction in the zone. All of the channels could be filled with the same buffer or one could initially fill only the reservoirs a208 and channels a206, blocking any significant liquid from entering analysis channel a214. The entry of liquid could be prevented by first filling analysis channel a214 and the waste reservoirs a220 and a224 and the buffer reservoir a222 using an appropriate pressure differential between the electrokinesis network and the reaction zone system. Alternatively, one could use a vacuum in one of the reservoirs a208 to pull liquid from the other reservoir a208 through the channels a206, while covering the reservoirs of the electrokinesis network. The particular manner in which one distinguishes the liquid in the reaction zone system and the electrokinesis network is not critical and any convenient method may be employed.

After appropriate addition of the reservoir liquid, where a meniscus will be formed in the zone a204, one or more components may be added to the zone to form a reaction. For example, one could have a library of candidate substrates, where the zone a204 initially contains an enzyme. The candidate substrates would be added to the zone and the reaction mixture incubated, where all or some of the candidate substrates would react to form product. Either or both the reactants and the products would have unique mobilities, preferably both. After completion of the reaction, electrodes could be added to the various reservoirs and the zone, as appropriate. Initially, an electrode would be activated in the reaction zone system, e.g. in the zone a204, and the waste reservoir a220. The charged substrates and products would move from the reaction zone a204 through side channel 210, through the portion of the analysis channel 214 between intersections a212 and a218 and into waste channel a216. The result is to form a slug of material from the zone a204 in the region between the intersections a212 and a218. When this region has a stable composition, the electric field is changed by activating electrodes in the buffer reservoir a222 and the waste reservoir a224. Depending on the nature of the substrates and products one may provide for a sieving medium in the analysis channel. The substrates and products will then move down the analysis channel a214 toward the waste reservoir a224 separating into bands in accordance with their respective mobilities. A detector may be placed along the analysis channel a214 for detecting the passage of the bands past the detector. By providing for fluorescently labeled or electrochemical molecule labeled substrate and/or product, one can readily detect a reduction or increase in the amount of substrate or product, respectively to determine the effect of a candidate compound on the reaction, the activity of an enzyme, or the like.

Figure 13:
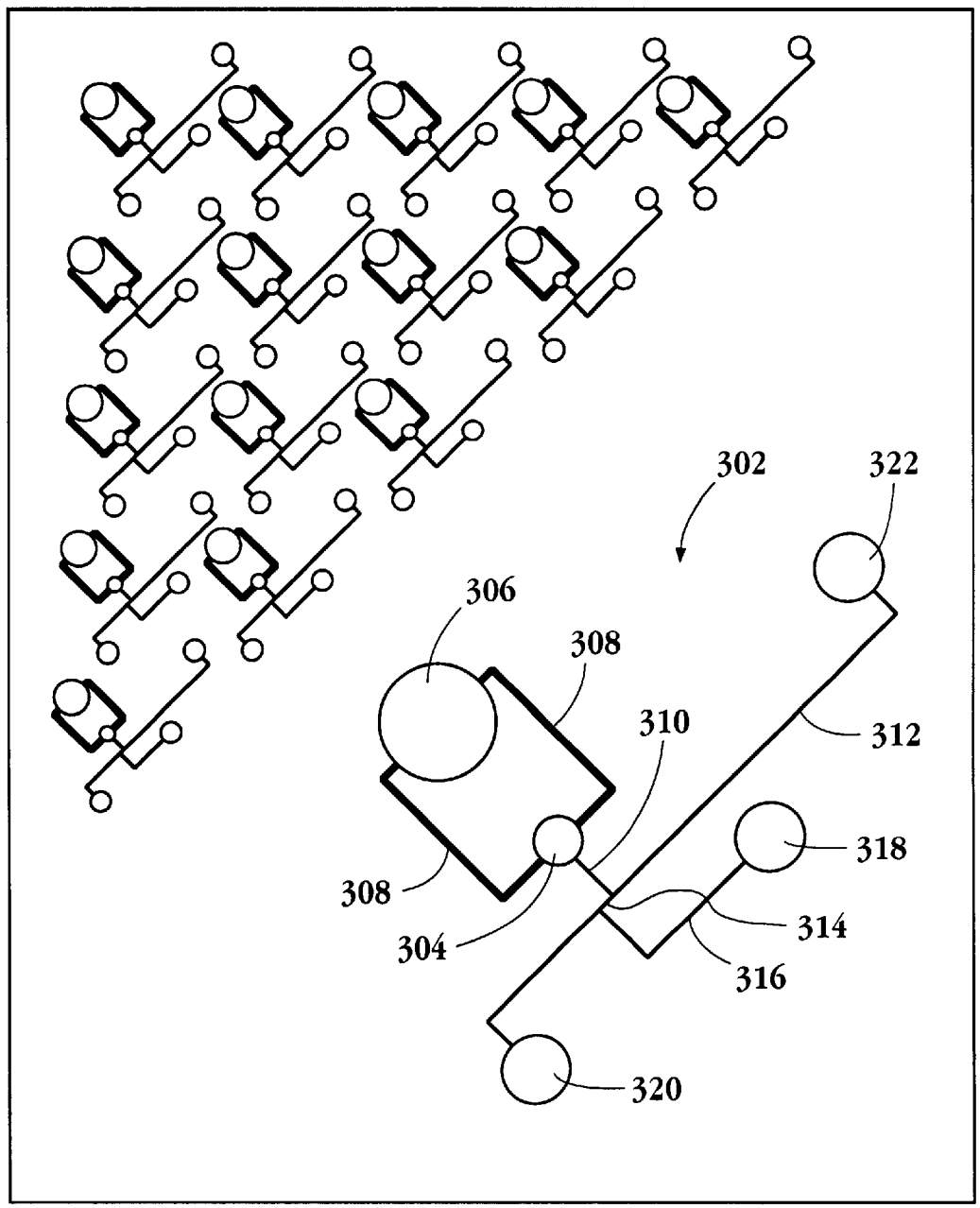
FIG. 13 is a diagrammatic plan view of an alternative embodiment of a combination of an assay system and an electrokinesis system, with an exploded view of one of the units.

FIG. 13 also exemplifies a combination of a reaction zone system and an electrokinesis system in a 96 well format. The device a300 has a plurality of units a302, with a reaction zone unit comprising the reaction zone a304, a reservoir a306 and connecting channels a308 connecting the reservoir a306 to the reaction zone a304 on both sides of the reaction zone a304. In this embodiment, there is a single reservoir a306 providing replenishment liquid to the reaction zone a304 on both sides of the reaction zone a304. Side channel a310 connects the reaction zone and, thus, the reaction zone system to the electrokinesis system. The side channel a310 is connected to the connecting channels a308 juncture at the reaction zone a304. The side channel a310 connects to the analysis channel. a312 at the intersection a314 with the waste channel a316. As distinct from the double-tee configuration, this configuration has the side channel a310 directly across from the waste channel a316, so as to connect the reaction zone a304 through the side channel a310 and the intersection a314 and the waste channel a316 to the waste reservoir a318. By having electrodes in the reservoir a306 and the waste reservoir a318, the components in the reaction zone a304 will be directed through the flowpath, as described above, to the waste reservoir a318. Once the composition from the reaction zone a304 has become substantially constant, electrodes placed in buffer reservoir a320 and analysis channel waste reservoir a322 may be activated to direct the composition at the intersection a314 into the analysis channel a312 for separation of the components as described previously.

The combination of the reaction zone system and the electrokinesis system is very powerful for performing a large number of different operations.

The following examples are offered by way of illustration and not by way of limitation.

EXPERIMENTAL

The following experiments were performed using a device substantially as depicted in FIG. 6. While the format of the device was kept constant, in different experiments the dimensions of the elements of the device were modified.

The device is comprised of a lower and upper plate. In the upper plate is a main channel, which forms a T at one end with an ancillary channel, which terminates in a reservoir at each end. The other end of the main channel terminates in a reservoir. Along the main channel are five evenly spaced ports formed in the upper plate. The upper plate also has openings for each of the reservoirs. The channels and reservoirs are enclosed by a base or lower plate.

The upper plate is about 1 mm in height and the lower plate is also about 1 mm in height. The port for introducing solutions is 1 mm in diameter and about 900 to 950 $\mu$m in height, while the channel substantially extends the remaining length of the upper sheet. The channel was varied from about 0.2 mm to 3.0 mm in width, where the interface between the port or well and the channel varied, with either the port or the channel determining the area of interface. The reservoirs have a diameter of about 2 mm. The channels were treated with 2N sodium hydroxide for 5 mins. using a vacuum pump to ensure that the basic solution extends through the channels and reservoirs. The ports or wells appear to be unaffected by this treatment, so that the channels and reservoirs have a hydrophilic surface, while the ports have a hydrophobic surface. One or more of the ports are used in each of the studies. Common to each of the experiments is to fill the device with 10 $\mu$l of 25 $\mu$M fluorescein diphosphate in 50 mM Tris buffer (pH 10.0) added to each of the inlet reservoirs, after prewetting the device.

In the first study, the channel is 1–2 mm wide and 10–30 nl of enzyme (alkaline phosphatase) is added to one of the ports and the fluorescence in the port is monitored for 60 mins. using a CCD camera. The fluorescence observed in the port increases with time, with the fluorescence primarily confined to the port area; a round fluorescent spot develops, which can be easily imaged with a CCD camera.

In the next study, the width of the channel is about 300 $\mu$m and 30 nl of 1 nM or 0.1 nM enzyme is added to a total of four ports and the fluorescence monitored with a CCD camera for 30 mins. The fluorescence is primarily confined to the ports and round fluorescent spots develop. The fluorescent signal can be easily related to the concentration of the enzyme introduced into the ports. Fluorescence is observed in the channel, which is substantially dimmer than the spots.

In the next study, a 2 mm wide channel is employed and 30 nl of 0.1 nM of enzyme was added to the ports and the increase in fluorescence at 5 min. intervals was monitored. A progressive increase in fluorescent signal is observed with the signal substantially confined to the ports. The amount of fluorescence in the channel is substantially less than in the previous experiment. This study was repeated with enzyme being added to two ports with a 1 mm wide channel and again the signal is substantially confined to the ports, with only dim fluorescence in the channel.

In the next study, the effect of enzyme inhibitor was investigated. The channel was 1 mm in width. Approximately 30 nl of pyridoxal phosphate (250 $\mu$M or 25 $\mu$M) is added to the ports followed by the addition of 30 nl of 0.1 nM of enzyme and all of the ports closed to diminish evaporation. The fluorescence development is monitored with a CCD camera. Fluorescence is substantially confined to the ports and the fluorescent signal is related to the concentration of inhibitor introduced into the port. The port in which 250 $\mu$M inhibitor was added is still very faint at 30 mins., while the port with only 25 $\mu$M appears to be only moderately inhibited.

In the next series of studies, a polyacrylic substrate was fabricated with side reservoirs of 2 mm diameter and wettable, a middle chamber of 1 mm diameter and non-wettable, with the connecting channel 100 $\mu$m deep and 300–500 $\mu$m wide. The hydrophilic surface treatment was performed as follows. The middle chamber was sealed with Scotch® tape. The channel was filled with 4N NaOH through either of the two reservoirs, and flushed through the channel with vacuum aspiration. The treatment was repeated a number of times, allowing the basic solution to stand in the device for up to 0.5 h each time. The device was then rinsed with deionized water several times. Upon adding buffer to the reservoirs, the buffer would move through the channel by capillary action. The capacity of the device was 10 $\mu$l.

In carrying out the determinations, one protocol was to seal the middle chamber and fill the channel by adding buffer to one or both of the reservoirs. The level of the reservoirs was then allowed to equilibrate. The middle chamber was unsealed, while holding the device steady. A Nanoplotter® (GeSim Corp., Germany) was used to dispense the reactants into the middle chamber, dispensing from 40 to 100 nl in volume. Depending on the nature and complexity of the dispensing, the time for dispensing varied from under a minute to 10 mins.

The signal detection system employed an Argon ion laser source, Nikon microscopic system with 4× objective, CCD camera and image frame capture software Rainbow PVCR. Fluorescence was excited at its optimal absorbent wavelength and its emission was collected through the CCD camera and captured by software Rainbow PVCR. The images were then analyzed using ImagePro Plus software. The fluorescent intensity was then quantified.

The rate of diffusion from the middle chamber was studied as follows 100 nl of 50 $\mu$M of 5-carboxyfluorescein in 30% DMSO was dispensed into the sample port (middle chamber). The reservoirs and channel were filled with 10 $\mu$l of 50 mM Tris buffer, pH 9.0. Fluorescence was excited at 480±nm and emission was at 530±20 nm, using the signal detection system described above. The fluorescent signals were recorded as a function of time. 80–90% of the original fluorescence intensity was maintained in the sample port region over 1 h. The fluorescent signal in the channel away from the sample port was found to be close to background. The loss of the fluorescein through the channel by diffusion is insignificant, as demonstrated in the following table.

|  | Time, Min | | | | |
| --- | --- | --- | --- | --- | --- |
| Distance from port | 0 | 5 | 15 | 30 | 60 |
| A__340 $\mu$M | 1 | 1.0399 | 1.03 | 1.04 | 0.86 |
| B__450 $\mu$M | 1 | 0.94 | 1.92 | 1.07 | 0.97 |
| D__1600 $\mu$M | 1 | 0.966 | 0.98 | 0.93 | 0.83 |

In the next study, enzyme kinetics were performed using alkaline phosphatase and substrate providing a fluorescent product. The channel was rinsed with AutoPhos buffer (JBL Scientific, Inc., San Luis Obispo, Calif.) and then filled with 10 µl of 1 mM AutoPhos substrate. 50 nl of alkaline phosphatase, at different concentrations was then dispensed into the sample port. The concentrations varied from 31.25 attomoles to 62.5 femtomoles with 2-fold dilutions. The fluorescent signals were recorded at different time points as described above. The following table indicates the results.

| ENZYME KINETIC ASSAY RESULTS | | | | | |
|---|---|---|---|---|---|
| | Conc., nM | | | | |
| Time | 1000 | 250 | 125 | 31.25 | 0 |
| 12 min. | 13390.8 | 2913.84 | 1497.68 | 821.08 | 0 |
| 20 min. | 20692.4 | 4698.56 | 2323.8 | 1055.88 | 0 |
| 30 min. | 28981.6 | 7579 | 2892.68 | 1798.84 | 0 |

As evidenced by the above results, the rate of the reaction is linear with the enzyme concentration in accordance with a 1st order reaction.

The next study evaluated the system using a competitive inhibition assay, 4-Nitrophenyl phosphate (PNPP). (Sigma Chemical Co., St. Louis, Mo.) was used as a non-fluorescent substrate for alkaline phosphatase (20 femtomoles) competing with the AutoPhos substrate. The channel was rinsed with AutoPhos buffer and filled with 1 mM AutoPhos substrate. Into the sample port was introduced 100 nl of PNPP at concentrations varying from 0 to 10 mM and the fluorescent signal was determined at different reaction time points. The fluorescent signal was found to diminish with increasing inhibitor concentration, the following table providing the results.

| ENZYME INHIBITION ASSAY | | | | | | | | | | |
|---|---|---|---|---|---|---|---|---|---|---|
| Inhibitor conc., mM | 0.001 | 0.0025 | 0.005 | 0.01 | 0.02 | 0.3125 | 0.625 | 1.25 | 5 | 10 |
| Fluorescent Signal × 103 | 4.5 | 4.0 | 4.0 | 3.5 | 2.6 | 2.0 | 1.6 | 1.6 | 1.6 | 1.5 |

In another series of studies binding assays were performed using fluorescence resonance energy transfer. The procedure employed is as follows. The channel was rinsed and filled with 25 µl of rhodamine labeled streptavidin and 100 nl of fluorescein labeled biotin dispensed in the sample port. The concentration of the antigen varied from 0 to 100 µM by 2-fold dilutions. The signal detection system was as described, except that emission was detected at 600±20 nm. The energy transfer increased corresponding to the increase in antigen. The study was repeated varying the amount of labeled streptavidin while keeping the biotin-fluorescein at 25 µM. The background FRET signal contributed by rhodamine-streptavidin alone was substantially negligible, when the concentration of rhodamine-streptavidin was greater than about 2 µM. The following tables provide the results for the two studies.

| BINDING ANTIGEN-RECEPTOR ASSAYS | | | | | | |
|---|---|---|---|---|---|---|
| Conc. Of Fluorescein Labeled antigen, mM | 100 | 50 | 25 | 10 | 5 | 0 |
| FRET Signal | 2956 | 2327 | 1639 | 869 | 370 | 0 |

In the next study the channel was rinsed and filled with 25 mM fluorescein-labeled antigen, 100 nl of rhodamine-labeled receptor dispensed into the sample port. Various concentrations of the rhodamirne-labeled receptor were employed, with excitation and emission as described above. The following table indicates the change in FRET signal with concentration of the rhodamine-labeled receptor. The background signal contributed by rhodamine-receptor alone is also indicated.

| Conc. Of Rhodamine Labeled receptor, mM | 0 | 0.25 | 0.5 | 1.5 | 3.5 | 5 | 6 | 8 | 12 |
|---|---|---|---|---|---|---|---|---|---|
| FRET Signal | 2192 | 3663 | 2264 | 3254 | 7619 | 10604 | 10882 | 11952 | 11552 |
| Background Signal | 1923 | 1430 | 2336 | 1312 | 556 | 211 | 516 | 759 | 1005 |

In the next study, the effect of inhibitor on the observed signal was investigated. Fluorescein-biotin was maintained at 50 µM and rhodamine-streptavidin at 25 µM the signal was read at 600±20 nm at varying concentrations of biotin as a binding inhibitor, with 100 nl of the binding inhibitor being added to the sample port. The energy transfer decreased with increase of binding inhibitor.

In the next study, the channel was filled with varying concentrations of biotin in the range of 0 to 5 µM and 100 nl of rhodamine-labeled streptavidin (625 nM) followed by 100 nl of 1.0 µM fluorescein-biotin added to the sample port. After incubating for 60 min., the signal was detected at 520±20 nm. The results are reported as fraction inhibition. The following tables provide the results.

| INHIBITION OF BINDING OF ANTIGEN-RECEPTOR ASSAYS | | | | | | | | | |
|---|---|---|---|---|---|---|---|---|---|
| Conc. Of Inhibitor, nM | 0 | 0 | 30 | 60 | 180 | 240 | 500 | 600 | 1000 5000 |
| Fraction of Inhibition | 0 | 0.0177 | 0.0385 | 0.0310 | 0.050 | 0.0514 | 0.224 | 0.3664 | 0.950 1.0 |

In the next series of studies, a number of different assays were performed in the subject devices, including a protease assay, alkaline phosphotase assay, ligand-receptor binding assay, homogenous time resolved fluorescence assay and fluorescence polarization assay. Initially, the device was evaluated as to the stability of a fluorescence signal over time, in the presence and absence of a loose cover. The device employed has substantially the same parameters as previously described. The reagents and protocol are as follows:

Reagents:
  5'-carboxyl-fluorescein (Molecular Probe, Eugene, Oreg.)
  50 mM Tris buffer (pH=9.0)

Protocol:
  700 nl buffer is dispensed into assay well followed by dispensing 3.2 µl buffer into each side well and 100 nl 50·M fluorescein into the assay well by Nanoplotter (GeSim Corp., Germany).

Fluorescein readings were taken at 0.30 min and 60 min using Fmax® microplate reader (Molecular Device). The same experiment was repeated except for putting a loose lid on the device.

The results are set forth in the following table.

TABLE

| Fluorescence Signal as a Function of Time | | | | |
|---|---|---|---|---|
| RFU | 0 min | 30 min | 60 min | 60 min with Lid |
| Mean | 65.14 | 60.82 | 54.57 | 51.096 |
| C.V. | 6.89% | 8.79% | 10.72% | 10.42% |
| Number of Wells | 27 | 27 | 27 | 27 |

In the next study a series of different enzyme assays were performed. The first assay was a protease assay using Cathepsin L protease as an exemplary protease and was chosen to demonstrate the correlation between a conventional 100 µl reaction in 96 well microtiter plates and a 200 nl reaction in a 33-hole subject device. This protease assay is a FRET based assay. The assay uses an internal quenched fluorogenic oligopeptide substrate, which incorporates the cleavage site for Cathepsin L protease. Incubation of human liver Cathepsin L with the fluorogenic substrate resulted in specific cleavage at the Arg-Val bond and a time-dependent increase in fluorescence intensity. The increase in fluorescence intensity is linearly related to the extent of substrate hydrolysis. FRET based protease assay facilitates the identification of novel inhibitors of various proteases such as HIV protease or renin protease, etc.

Reagents:
  Human liver Cathepsin L (Cat #219402, Calbiochem-Novabiochem Corp., La Jolla, Calif. 92039).
  Enzyme buffer: 100 mM NaOAc, 1.5 mM DTT (pH 5.5).
  Cathepsin L substrate: FITC-LC-Glu-Lys-Ala-Arg-Val-Leu-Ala-Glu-Ala-Ala-Lys(ε-DABCYL)—OH (Cat #ABSS-2, AnaSpec Inc., San Jose, Calif. 95131). The substrate was dissolved in anhydrous DMSO at concentration of 800 µM and further diluted in the same buffer mentioned above. Seven different Cathepsin L inhibitors (Calbiochem corp.) were dissolved in anhydrous DMSO at a concentration of 1 mM and further diluted in the buffer solution mentioned above.

The Cathepsin L protease assays used 33-zone cards. These cards have 3 rows of 11 wells on each. The diameter of the sample well is 1 mm and 1.5 mm for the reservoirs. The channel connecting the sample well and reservoirs is 450 µ in width, 100µ in depth and 3.5 mm in length (total 7 mm in length). The depth of the evaporation control well is 1 mm. The device was laminated with Rohm film, which was plasma treated. The plastic for the substrate is V825. All the protease assays were conducted on plasma treated film laminated cards unless specified otherwise. These cards were placed in cardholders. The design of the holder was customized so as to accommodate the optimized optical reading for a 96 well microtiter format under a fluorescence plate reader (Fmax, Molecular Devices).

The protocol is as follows:

After placing the card in its holder, 700 nl of Cathepsin L substrate is added to the sample well by contacting the bottom of the sample well with the pipette tip, with flow of the liquid toward the reservoirs, avoiding the formation of bubbles. 3.2 µl of the substrate is then added to the reservoirs. The fluorescence intensities are recorded using an Fmax plate reader at 485 nm excitation/535 nm emission to determine the assay background fluorescent signals. The gain of the signal collection was set to 2.65, the integration time for each sample well was 20 msec and the plate scanning speed was set at the highest mode which was 10 in the scale of 1 to 10. The reactants were dispensed using aNanoplotter (GeSim Corp., Germany) through the sample port at 50 or 100 nl in volume.

The coefficient of variation was determined with two of the cards, using the above protocol, except that the Cathepsin L substrate was 40 µM and 50 nl of 46.8 mg/ml Cathepsin L was dispensed into each sample well and the mixture incubated at room temperature for 1 h.

The signal for card 1 and card 2 were 24.5±2.3 (n=31) and 26.4±4.2 (n=31), respectively. Therefore, the c.v. for card 1 and card 2 were 9.2% and 15.9%, respectively. One-way analysis of variance was performed and it was found that there was no significant difference (p=0.038, α=0.05) between assay signals obtained from cards 1 and 2. The overall assay signals for both LabCards were 25.5±3.5 (n=62) with C.V. of 13.7%.

In the next study, a comparison was made of the results for the same assay between the subject card and a 96 well microtiter plate. The channel was filled with 40 µM substrate by adding 700 nl into the sample well and 3.2 µl into both reservoirs. The assay background signals were measured. Then, 50 nl of Cathepsin L at 4 different concentrations were dispensed into different sample wells using a Nanoplotter. There were six replicates for each of the four different concentrations and one negative control where no protease was added. The following table shows the mean and standard deviation of fluorescent signals corresponding to five different amounts of protease. The relationship of the fluorescent signal with the increasing protease concentration in the reaction was RFU=4.522×[protease]+1.4 with $R^2$ equal to 0.99.

TABLE

Flourescent Signals at Different Amounts of Cathepsin L in Cards

| Cathepsin L, ng | Mean of RFU (n = 6) | S.D. of RFU |
|---|---|---|
| 0 | 2.246611 | 0.533557 |
| 0.47 | 3.477907 | 0.746098 |
| 1.17 | 6.03478 | 0.882803 |
| 4.68 | 27.39389 | 1.707562 |
| 11.70 | 52.56761 | 6.542091 |
| Card Background | 0.760415 | 0.442258 |

The Protocol for the microtiter well plate comparison was as follows. A black polystyrene U-bottom 96-well microtiter plate (Dynex) was used. 78 $\mu$l of Cathepsin L buffer was added into the wells followed by 10 $\mu$l of Cathepsin L at different concentrations, and finally 200 $\mu$M of substrate. Three replicates were performed for each protease concentration including the negative control. The reactions were incubated for 1 h before measuring the fluoresent signals. The following table shows the mean and standard deviation of the fluoresence signals at different protease concentrations.

TABLE

Fluorescent Signals at Different Amount of Cathepsin L in 96-Well Plates

| Cathepsin L, ng | Mean of RFU (n = 3) | S.D. of RFU |
|---|---|---|
| 0 | 1.6234 | 0.1047 |
| 40 | 2.6897 | 0.1563 |
| 342 | 38.8344 | 2.1132 |
| 585 | 54.7233 | 3.8047 |

The relationship of fluorescent signal with increasing protease concentration in the reaction was RFU=0.0951×[protease]+1.6 with $R^2$ equal to 0.98. The results from the card and 96-well plate were comparable.

To estimate the reduction in reagents, the required quantity of the reagent for each assay can be derived from the above signal as a function of enzyme concentration plot. To set the ratio of assay signal to assay background the same for both 96-well plate and card, the ratio of the required enzyme for the 96-well plate and the card is as following:

$$\frac{M_{96well}}{M_{OASIS}} = \frac{Slope_{OASIS}}{Slope_{96well}} * \frac{Int_{96well}}{Int_{OASIS}} = 106$$

(OASIS intends the device according to this invention.) In other words, when the assay reaction volume reduces to 250 nl in cards from 100 $\mu$l in a 96-well plate, the key reagent protese is used in 106 times less amount.

The next study was a determination of the effect of inhibitors on the protease assay. For each inhibitor, five different concentrations of inhibitor were used (0.1 $\mu$l–1000 $\mu$l with one log increment), there were six replicates for each concentration of inhibitor and three replicates for one negative control, where no inhibitor was added. One card was required to run one set of experiments for each inhibitor assay. For each experiment, the card was placed in the cardholder and the channel filled with 700 nl of 20 $\mu$M substrate through the sample well followed by 3.2 $\mu$l of substrate at each reservoir. The assay background signals were measured. 50 nl of inhibitor was dispensed into the sample well followed by dispensing 50 nl of 23.4 ng of Cathepsin L. The card was incubated for half an hour at room temperature covered by a dark loose lid to avoid direct light. The fluorescent signals were measured. In the data analysis, the assay background signals were subtracted from the reaction signal at each different concentration of the inhibitor. The fraction of the control signal is the ratio of reaction signal over control signal. The decreasing of the signal, or the smaller the fraction of the control signal, indicated the inhibition of the Cathelpsin L protease. The following table indicates the results.

TABLE

Fraction of the Control Signal vs. Inhibition Concentration in Card

| [Inhibitor], · M | Fraction of Original Intensity ||||||| 
|---|---|---|---|---|---|---|---|
| | Inh_1 | Inh_2 | Inh_3 | Inh_4 | Inh_5 | Inh_6 | Inh_7 |
| 0.001 | 1.0 | 1.0 | 1.0 | 1.0 | 1.0 | 1.0 | 1.0 |
| 0.01 | 0.92 | 0.98 | 0.89 | 0.89 | 0.57 | 0.64 | 0.56 |
| 0.1 | 0.77 | 0.79 | 0.47 | 0.46 | 0.55 | 0.32 | 0.35 |
| 1 | 0.56 | 0.33 | 0.13 | 0.056 | 0.30 | −0.002 | 0.097 |
| 10 | 0 | 0.14 | 0 | 0 | 0 | 0 | 0 |

For comparison, inhibition assays were carried out under comparable conditions in a 96-well microtiter plate. For each inhibitor, five different concentrations of inhibitor were used (0.1 $\mu$M–1000 $\mu$M with one log increment), there were three replicates for each concentration of inhibitor and one negative control where no inhibitor was added. In each well, 75 $\mu$l of Cathepsin L buffer was added followed by 10 $\mu$l of protease (40 mg) and 5 $\mu$l of inhibitor. 10 $\mu$l of 200 $\mu$M substrate was added last. The reaction was also incubated for half an hour. The data analysis was the same as above. The following table indicates the results.

TABLE

Fraction of the Original Reaction Signal vs. Inhibition Concentration in 96-well Microtiter Plate Reaction

| [Inhibitor], · M | Fraction of Original Intensity | | | | | | |
|---|---|---|---|---|---|---|---|
| | Inh_1 | Inh_2 | Inh_3 | Inh_4 | Inh_5 | Inh_6 | Inh_7 |
| 0.0005 | 1.0 | 1.0 | 1.0 | 1.0 | 1.0 | 1.0 | 1.0 |
| 0.005 | 0.96 | 0.90 | 1.01 | 0.94 | 0.58 | 0.021 | 0.49 |
| 0.05 | 0.92 | 0.76 | 0.92 | 0.88 | 0.13 | 0.036 | 0.32 |
| 0.5 | 0.17 | 0.29 | 0.093 | 0.10 | 0.049 | 0.0076 | 0.038 |
| 5 | 0.033 | 0.32 | 0.052 | 0.062 | 0.031 | 0.0030 | 0.036 |

The results showed the reaction performance between the 96-well plate and card were comparable, despite the large disparity in the amount of the protease used in the card assay.

Figure 21:
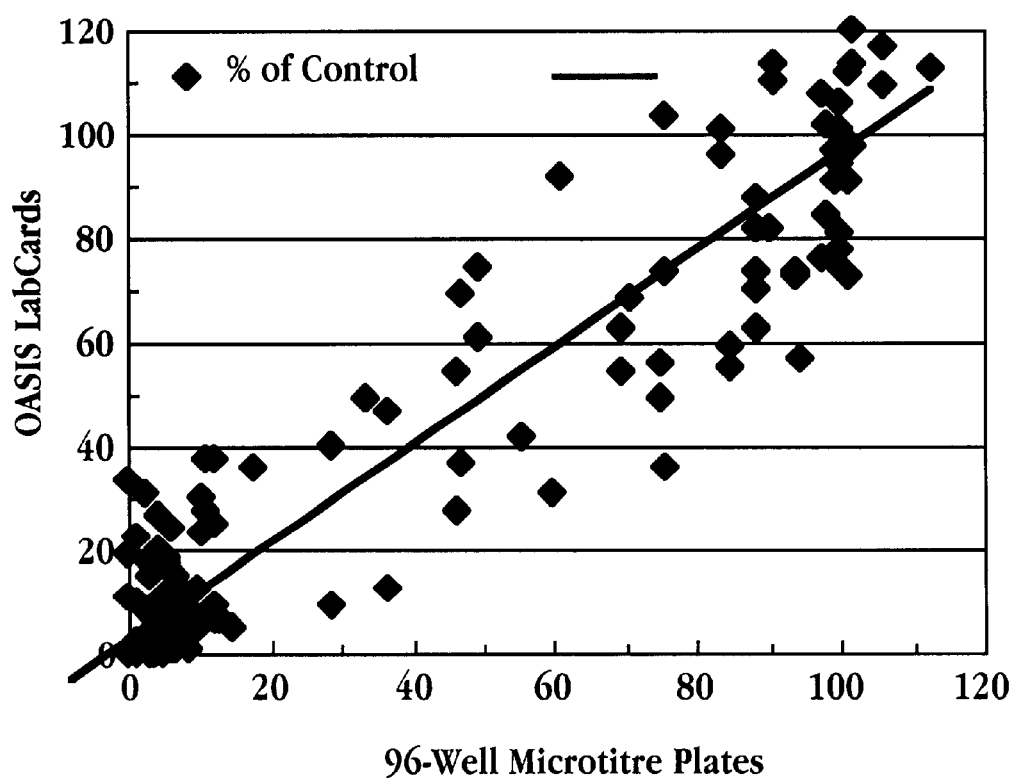
FIG. 21 is a plot of the correlation of the performance between OASIS lab cards and 96-well plates.

The correlation of the performance between cards and 96-well plates is shown in FIG. 21. Inhibition of the cleavage of the substrate by the protease was reflected by the decrease in the fluorescent signal. The correlation between 96-well plate and card systems was satisfactory with an r value of 0.96. From this preliminary result, taking results from the 96-well plate as the reference, if the cut off value for the first phase screening was 80% of the control signal, there would be 3 false negatives and fewer than 10 false positives.

The next assay was another hydrolase assay, using alkaline phosphatase as the enzyme. The reagents and protocol are as follows.

Reagents:
  Alkaline phosphatase (Sigma, St. Louis, Mich.)
  AutoPhos buffer (JBL Scientific, Inc., San Louis Obispo, Calif.)
  1 mM MgCl$_2$
  4-Nitrophenyl Phosphate (PNPP) (Sigma Chemical, St. Louis, Mich.)

Protocols:

The channel was rinsed with AutoPhos buffer and then filled with about 10 µl of 1 mM AutoPhos substrate. 50 nl of alkaline phosphatase was then dispensed into the sample port. The amount of enzyme dispensed into the sample port increased from 31.25 attomole to 62.5 femtomoles by a factor of 2. Enzyme solutions of different concentrations were prepared in individual wells of a 96-well microtitre plate. Fluorescence was excited at 480 nm±20 nm and emission collected at 520±20 nm. The signals were recorded at different time points, 0, 5, 10, 15, up to 35 minutes.

The results are shown in the following table. The fluorescent signal as a function of enzyme concentration at reaction times of 12, 20, and 30 minutes respectively was shown to be linear with the enzyme concentration in accordance with the $1^{st}$ order reaction.

TABLE

Fluorescence Signal as a Function of Enzyme Concentration and Reaction Time

| Time, min | [Enzyme], nM | | | |
|---|---|---|---|---|
| | 1000 | 250 | 125 | 31.25 |
| 12 | 13390.8 | 2913.8 | 1497.7 | 821.1 |
| 20 | 20692.4 | 4698.6 | 2323.8 | 0 |

TABLE-continued

Fluorescence Signal as a Function of Enzyme Concentration and Reaction Time

| Time, min | [Enzyme], nM | | | |
|---|---|---|---|---|
| | 1000 | 250 | 125 | 31.25 |
| 30 | 28981.6 | 7579.0 | 2892.7 | 1798.8 |

In addition, as to each enzyme concentration, in the presence of sufficient enzyme substrate, the rate is linear with time.

Time Course of the Alkaline Phosphatase Reaction—Determination of the Diffusion during Incubation of Large Molecules such as Enzymes Procedure:

After taking, the image of the empty card with the lamp on, 5·1 of 1 mM AutoPhos was added to each reservoir followed by adding 400 nl of 1 mM AutoPhos to the assay well. A card image was taken with the lamp off followed by taking an image with the lamp on. 200 nl of 2 µ/ml of enzyme was added to the assay well and images taken every minute with the lamp on.

Figure 22:
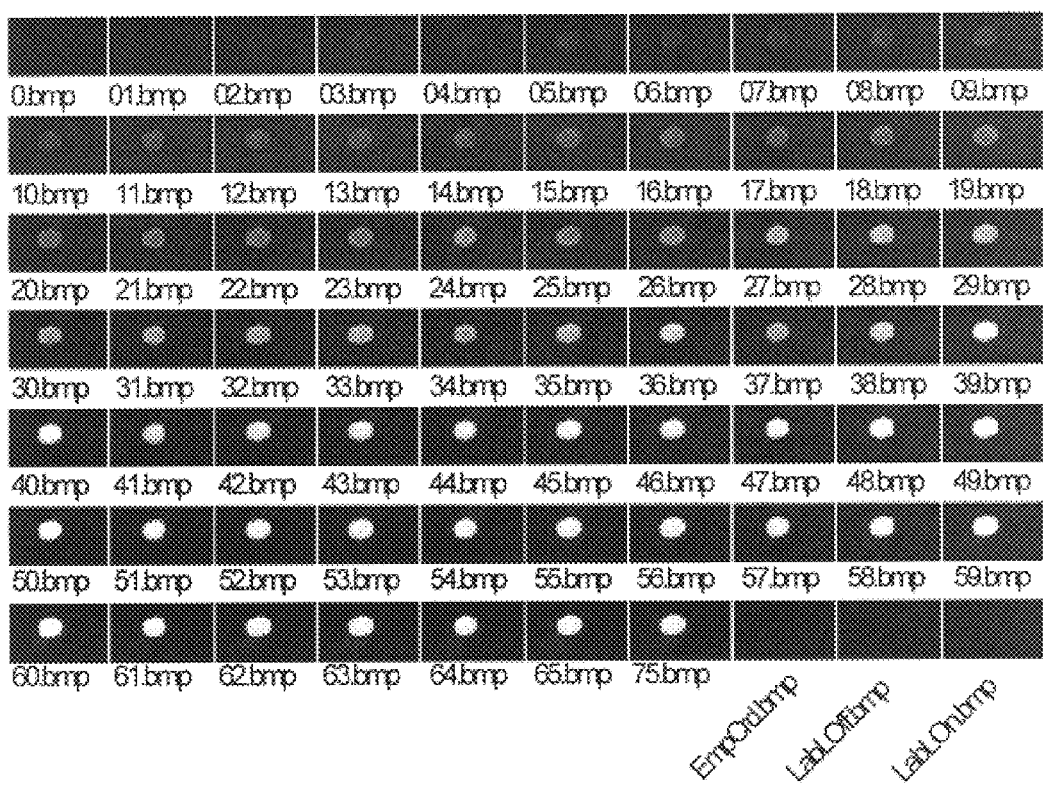
FIG. 22 shows images of the fluorescence from an alkaline phosphatase reaction in a 1 mm assay well.

Results:

As seen in FIG. 22, images show the fluorescence from an alkaline phosphatase reaction in a 1 mm assay well. The fluorescent signal increased as the reaction proceeded. In addition, as seen, most of the fluorescence is concentrated in the assay well, without significant diffusion of the fluorescer.

The next assay was a competitive inhibition assay using the following protocol: 4-Nitrophenyl phosphate (PNPP) was used as a non-fluorescent substrate for competing for alkaline phosphatase with AutoPhos substrate. After rinsing the channels with AutoPhos buffer, the channel was filled with 1 mM AutoPhos substrate. 100 nl of PNPP was dispensed at different concentrations ranging form 0 to 60 mM. The fluorescent signal was measured at different reaction time points. The fluorescent signal as a function of different inhibitor concentrations is tabulated as following.

TABLE

Fluorescence Signal as a Function of Inhibitor Concentration

| [Inhibitor], mM | 0.001 | 0.0025 | 0.005 | 0.01 | 0.02 | 0.3125 | 0.625 | 1.25 | 5 | 10 | 60 |
|---|---|---|---|---|---|---|---|---|---|---|---|
| RFU | 4527 | 4000 | 4000 | 3500 | 2600 | 2000 | 1600 | 1600 | 1600 | 1500 | 750 |

The following study used the Receptor-Ligand Binding Assay via Fluorescent Resonance Energy Transfer (FRET). The reagents and protocol are as follows.
Reagents:
  Fluorescein labeled biotin (Molecular Probe, Eugene, Oreg.)
  Rhodamine labeled streptavidin (Molecular Probe, Eugene, Oreg.)
  D(+)-Biotin (Molecular Probe, Eugene, Oreg.)
  50 mM Tris buffer (pH=9.0)

The channel is rinsed and filled with 25 $\mu$M of rhodamine labeled receptor, and 100 nl of fluorescein labeled antigen is dispensed into the assay well. The concentrations of fluorescein labeled antigen were 0, 5, 10, 25, 50 to 100 $\mu$M, respectively. The fluorescence was excited at 480+20 nm and the emission was collected at 600 nm±20 nm. Shown in the following table is the fluorescence resonance energy transfer (FRET) signal vs. concentration of fluorescein labeled antigen. The energy transfer increased in relation to the increasing antigen-receptor binding.

TABLE

FRET Signal as a Function of Fluorescein Labeled Antigen

| [F1-Antigen], · M | 0 | 5 | 10 | 25 | 50 | 100 |
|---|---|---|---|---|---|---|
| FRET Signal | 0 | 370 | 869 | 1639 | 2327 | 2956 |

In the next study the channel was rinsed and filled with 25 $\mu$M of fluorescein labeled antigen, followed by dispensing 100 nl of rhodamine labeled receptor into the sample port.

The concentration of rhodamine labeled receptor was 0, 0.25, 0.5, 1.0, 1.5, 2, 2.5, 3, 3.5, 4, 5, 6, 8, 10, and 12 $\mu$M respectively. The fluorescence was excited at 480±20 nm and the emission was collected at 600 nm±20 nm. Shown in the following table is fluorescence resonance energy transfer (FRET) signal vs. concentration of rhodamine labeled receptor. The energy transfer increased corresponding to the increasing in antigen-receptor binding. The background FRET signal contributed by rhodamine-receptor alone was negligible.

fluorescence was recorded by exciting at 480±20 nm and reading the emission at 520 nm±20 nm As the inhibitor concentration increased, the fluorescence intensity increased, indicating an increased inhibition. The increase in the fluorescent signal as a function of inhibitor concentration was converted to the percentage of inhibition. The results are displayed in the following table.

TABLE

Inhibition vs. Inhibitor Concentration

| [Inhibitor], nM | 0 | 30 | 60 | 180 | 240 | 500 | 600 | 1000 | 5000 |
|---|---|---|---|---|---|---|---|---|---|
| % of Inhibition | 0 | 3.85 | 3.10 | 5.00 | 5.14 | 22.4 | 36.64 | 95.0 | 100.0 |

The following assay is a HTRF-FRET assay. In TRF, the species are excited through a pulse of laser light, and the emission is then collected in a delayed time protocol (typically 50 $\mu$s). Therefore, the initial burst of the fluorescence mostly from background (lifetime of the order of 10 ns) is eliminated. The homogenous assay of TRF was based on fluorescence resonance energy transfer (FRET). The donor fluorophore is europium cryptate (europium ion caged in a tris-bipyridine structure) with a long-lived emission (~milliseconds) at 620 nm upon excitation at 380 nm. The acceptor fluorophore is a stabilized allophycocyanin XL665 When XL665 is in proximity to europium cryptate as a result of a biomolecular interaction, the energy is transferred to the XL665 and is emitted as a long-lived 665 nm signal. The emission of free acceptor XL665 is short-lived. This FRET pair has a high yield energy transfer of 50% at 9.5 nm, and is the longest energy transfer distance reported for a FRET pair.

The card employed was a white acrylic card laminated with plasma treated Rohm film. The following are the reagents and protocol.
Reagents:
  Biotin-K, Labeled with europium cryptate ("Biot-K", CIS bio international)
  Containing buffer: phosphate 0.1 M, pH 7.

TABLE

FRET Signal vs. Rhodamine Labeled Receptor

| [Rh-Receptor], $\mu$M | 0 | 0.25 | 0.5 | 1.5 | 3.5 | 5 | 6 | 8 | 12 |
|---|---|---|---|---|---|---|---|---|---|
| FRET Signal | 2192 | 3663 | 2264 | 3254 | 7619 | 10604 | 10882 | 11952 | 11552 |
| Bkgd Signal | 1923 | 1430 | 2336 | 1312 | 556 | 211 | 516 | 759 | 1005 |

Using the above reagents and protocol, an inhibition assay was performed. The protocol was to fill the channel with 0, 30, 60, 180, 240, 500, 600, 1000, 5000 $\mu$M of biotin, respectively, followed by dispensing 100 nl of rhodamine labeled receptor into the sample port. After dispensing 100 nl of 1.0 $\mu$M fluorescein labeled antigen into the sample port, the reaction mixture was incubated for 60 minutes. The SA-XL, streptavidin labeled with XL665 (Allophycocyanin, CIS bio international)
  Conditioning buffer: phosphate 0.1 M, pH 7
  TR-FRET buffer: 50 mM TRIS, 100 nM KF, 0.1% BSA, pH 8.

A euroypium cryptate concentration standard curve was prepared. Biotin labeled europium cryptate (Biotin-K) was diluted in various concentrations shown in the table below. 500 nl of different concentrations of Biotin-K was then added to the assay well. There were three replicates for each concentration. The instrumental setting was the same as the one for the previous-FRET assay. The range of europium cryptate concentration was tested to determine the desirable Biotin-K concentration for the FRET assay. The average and standard deviation of the doner signals are shown in the table. The acceptor signals were negligible compaired to the background. The donor signals are linear corresponding to the europium cryptate concentration. Biotin-K concentration of 400 pg/well was selected for the further TR-FRET assay.

TABLE

Biotin-K Concentration vs. Donor Emission Signal

| Biotin K, pg | Mean | STD |
| --- | --- | --- |
| 0 | 70584.5 | 20952.3 |
| 25 | 84582.67 | 26065.5 |
| 50 | 72946.33 | 2105.7 |
| 100 | 125456 | 13859.1 |
| 150 | 252819.3 | 18653.7 |
| 200 | 243819.3 | 17990.6 |
| 300 | 614849.3 | 102782.6 |
| 400 | 662512.7 | 160733.5 |
| 500 | 889204.5 | 308942.7 |
| 1000 | 1666774 | 336795 |
| 2000 | 2716030 | 354542.6 |

TR-FRET signals:

In the next assay, the channel was filled with 5 µl of TR-FRET buffer Then 500 nl of Biotin-K was added to the assay well followed by a 500 nl addition of different concentrations of SA-XL to the assay well. Six replicates for each concentration point were performed The signals were detected using an HTS Analyst manufactured by LJL Bio-Systems. It was observed that as As SA-XL665 concentration increased, more binding of biotin-K occurred, resulting in increased energy transfer. Therefore, the donor emission decreased with the increasing acceptor concentration indicating energy transfer was occurring, while the acceptor emission increased as energy was retained. As limited by the available biotin-K, the energy transfer leveled off at higher concentrations.

to the fluorescence lifetime, the observed fluorescence will remain significantly polarized. In general, a molecule's rate of tumbling is directly proportional to its molecular volume at constant temperature and viscosity. Small molecules tumble rapidly while large molecules tumble slowly. When a small fluorescent molecule is bound to a large molecule, it will tumble slowly. Therefore, by measuring the extent of fluorescence polarization, the binding equilibrium and the competition for binding at a site can be determined. The following are the reagents and protocols employed.

Reagents:
  PTK detection mix (anti-phosphotyrosine antibody, fluorescent phosphopeptide tracer, NP40, sodium azide, in phosphate buffer saline, pH 7.4)
  PTK competitor (100 µM phosphopeptide in DEPC-treated water)
  PTK standard curve dilution buffer (phosphate buffer saline pH 7.4)

Protocols:
  The competitor was diluted to the following concentrations in the same buffer: 100 µM, 10 µM, 1 µM, 0.1 µM, and 0.05 µM 1 µl of detection mix was added to the assay wells, followed by the addition of 3.2 µl of detection mix to the reservoirs. 500 µl of competitor solution was added to the assay wells. Six replications for each concentration point were performed. The assay mixtures were incubated at room temp. for 5 min. and the polarization measured using an LJL BioSystems' HTS Analyst microplate reader. The results are as follows. The extent of fluorescence polarization can be indicated as:

$$mP = \frac{s-p}{s+p} * 1000,$$

where s is the signal from the same plane of the excitation, while p is the signal from the perpendicular plane to the plane of excitation. The extent of the fluorescence polarization will vary in the range of 0 to 1000 with a higher value indicating a higher degree of polarization. Shown in the table, when a small phosphopeptide labeled with a fluorescence tracer (Fl-

TABLE

Acceptor Concentration vs. FRET Signal

| | SA-XL1665, ng | 0 | 0.1 | 1 | 5 | 10 | 50 |
| --- | --- | --- | --- | --- | --- | --- | --- |
| Donor | Mean | 243819.3 | 186521 | 156683.8 | 132737.6 | 131324.8 | 122187.7 |
| | SD | 17990.59 | 55422.59 | 61107.69 | 45203.64 | 43235.92 | 26462.03 |
| Acceptor | Mean | 21721.89 | 34277 | 74506.4 | 99773 | 91039.4 | 84773 |
| | SD | 3916.839 | 7590.534 | 28612.11 | 46441.94 | 18667.63 | 23051.49 |

The next assay was a fluorescence polarization assay.

Fluorescence polarization (FP) is a technique that is used to monitor molecular interactions in a homogenous environment at equilibrium. FP is based upon the theory that when a molecule is excited with plane-polarized light of the correct wavelength, it will fluoresce in the same plane after its characteristic emission lifetime, which is typically a few nanoseconds. During this time, the molecule will have tumbled randomly with respect to the original plane of excitation. If the molecule tumbles quickly with respect to the fluorescence lifetime, the fluorescence will be depolarized. However, if the molecule tumbles slowly with respect phosphopeptide tracer) was bound to the bigger phosphotyrosine antibody, the polarization signal was high. As concentrations of unlabeled phosphopeptides increased competing for the same binding sites of the phophostyrosine antibody, more and more Fl-phosphopeptide tracers remained unbound and free in solution and the signals were depolarized. The $IC_{50}$ for the competition was determined as ~0.5 µM in accordance with the 0.4–0.6 µM value reported in the literature.

TABLE

Competitor Concentration vs. Polarization Signal

| Competitor, $\mu M$ | 100 | 10 | 1 | 0.1 | 0.05 |
|---|---|---|---|---|---|
| mP | 112.1649 | 136.3539 | 243.4099 | 276.376 | 333.9214 |

Figure 14:
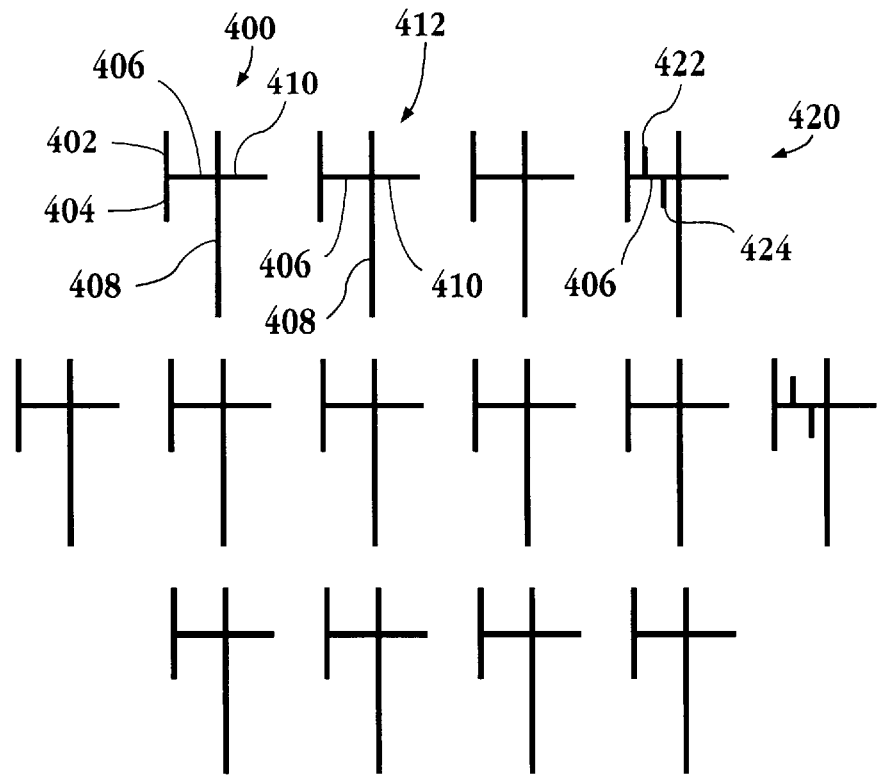
FIG. 14 is a diagrammatic plan view of a card with three different organizations of channels for the combination of an assay system and an electrokinesis system.

In the next study assays were performed in assay wells, where the solution in the assay well could be transferred to a capillary electrokinesis system for further processing. FIG. 14 shows the layout of the capillary electrophoresis card, the CE card. As can be seen in this Figure, the CE^2 card has three different patterns. Each pattern consists of two parts; evaporation control assay system and injection/separation capillary electrokinesis system.

Figure 15:
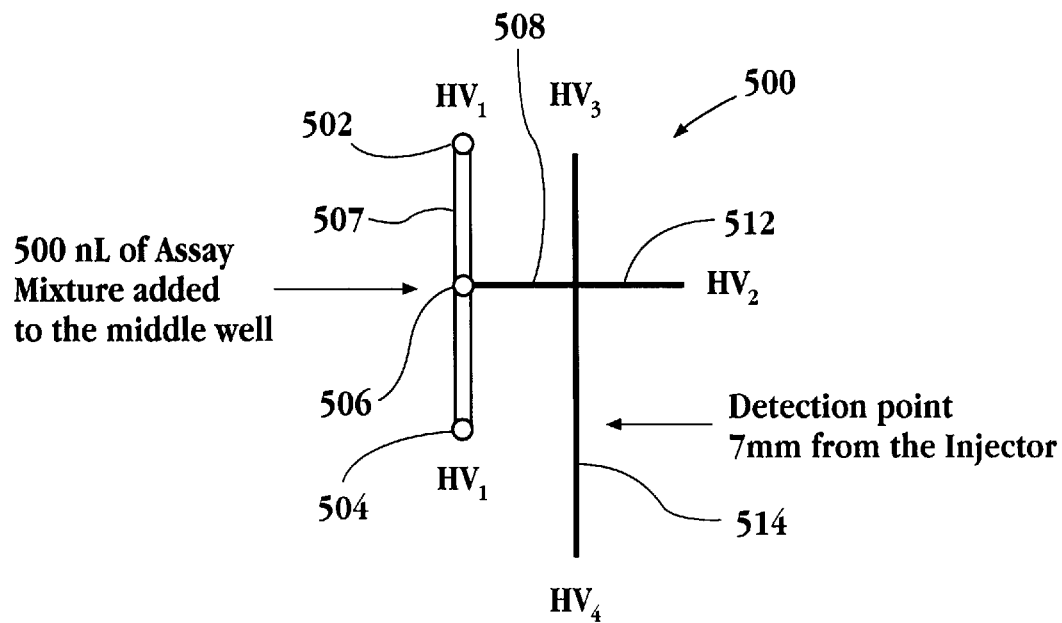
FIG. 15 is a diagrammatic plan view of a single unit indicating the sites of the electrodes and the detection site.

The devices are shown as stick diagrams, where the reservoirs at the ends of the lines, which depict the channel pattern, are not shown. See, for example, FIG. 7A for an indication of the channels and reservoirs. Device a400 has capillary channel a402, with reservoirs at its termini, a502 and a504 as depicted in FIG. 15, with an assay well at the intersection a404, as shown in FIG. 15 at a506. The side channel connects capillary a402 with the capillary electrokinesis system comprising analytical channel a408 and waste channel a410. The device a412 differs from the device a400 in having the side channel a406 offset from the waste channel, so that there is a region between the side channel a406 and the waste channel a410 along the analytical channel a408, which serves to define the size of the slug of the assay composition that will be detected in the analytical channel a408. Device a420 differs from the device a400 in having hydrostatic head control channels a422 and a424 along side channel a406, to provide better control of the hydrostatic head during long incubations in the assay system. In FIG. 15, device a500, is analogous to device a400 with assay system capillary channel a508 being. connected to side channel a406. The intersection a512 serves as the injector or injection site for injection of the assay composition into the analytical channel. $HV_{1-4}$ intends the voltages of the electrodes-during the transfer of the composition from the assay well a506 into the capillary electrokinesis system for transport to the intersection a512 and injection into the analytical channel a514.

The assay well system incorporates a wide channel (450 $\mu m$ wide and 50 $\mu m$ deep) with two buffer reservoirs (2 mm in diameter) and the evaporation control well (1 mm diameter) in the middle of the channel. The second part of the CE^2 device which is the injection/separation part consists of injection and separation channels with dimensions of 120 $\mu m$ wide and 50 $\mu m$ deep. The injection channel is connected directly to the evaporation control well. As shown in the FIG. 15, some of the patterns have no offset (simple cross) and the others have a 250 $\mu m$ offset (double-T injector). The third pattern has two more side channels for the purpose of controlling the hydrostatic flow within the channel manifold if a long incubation time is needed. The channels are closed by laminating a film (plasma treated Rohm or MT40) on the card.

The experimental procedure was as follows: the assay well is covered by tape. 5 $\mu l$ of buffer was added to the reservoirs. 500 nl of the fluorescein or assay mixture was pipetted into the assay well. For the alkaline phosphatase assay, enzyme and substrate with or without inhibitor was mixed in a tube and then 500 nl of the assay mixture was pipetted into the assay well. The detection was performed at 7 mm distance from the injector. The particular conditions for each determination are set forth with the figure.

The following table shows the voltage configuration for these assays

| | Electrode 1 | Electrode 2 | Electrode 3 | Electrode 4 |
|---|---|---|---|---|
| Injection | 220 | 500 | 155 | 0 |
| Separation | 0 | 280 | 1000 | 280 |

Figure 16:
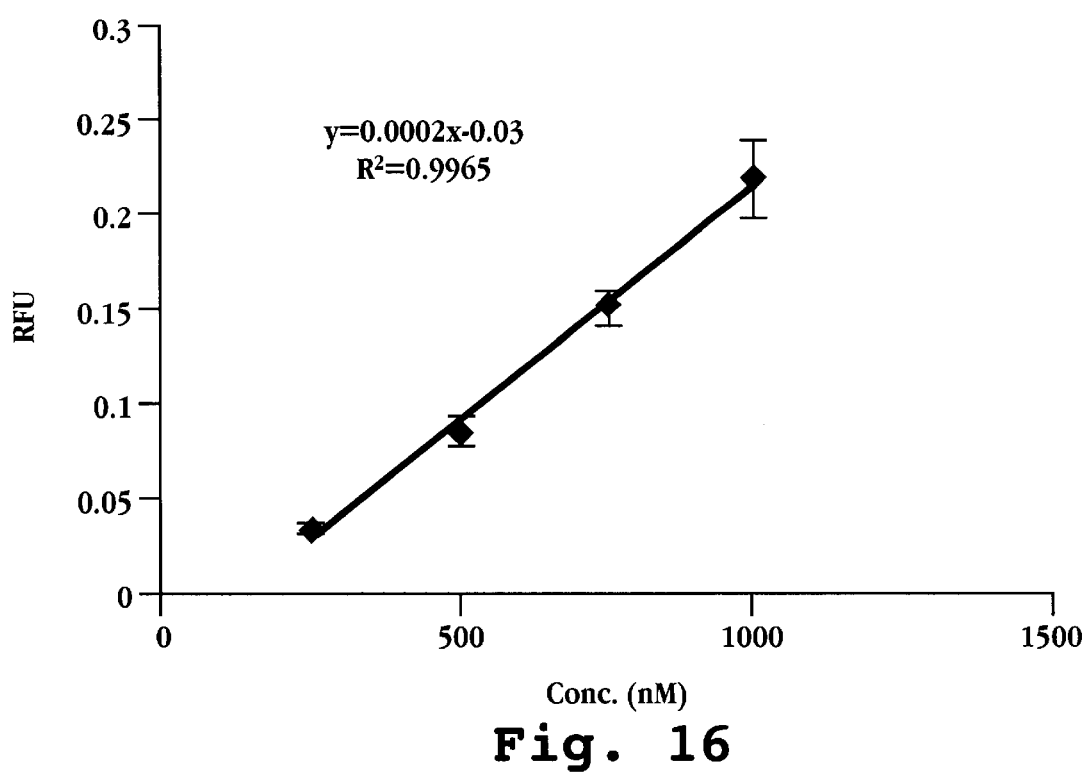
FIG. 16 is a calibration curve for fluorescein in a subject device.

To perform the analysis of-the maintenance of signal in the assay well, 500 nl of fluorescein was added to the assay well and the whole card covered by a 96 well plate for 75 min. Then the fluorescein was moved to the intersection, consecutively injected and separated for another 15 min. A CV of 7–13% was achieved for these repetitive injections. FIG. 16 shows the calibration curve for fluorescein using the card. As can be seen a linear calibration curve was achieved in the concentration range of 250–100 nM.

Figure 17:
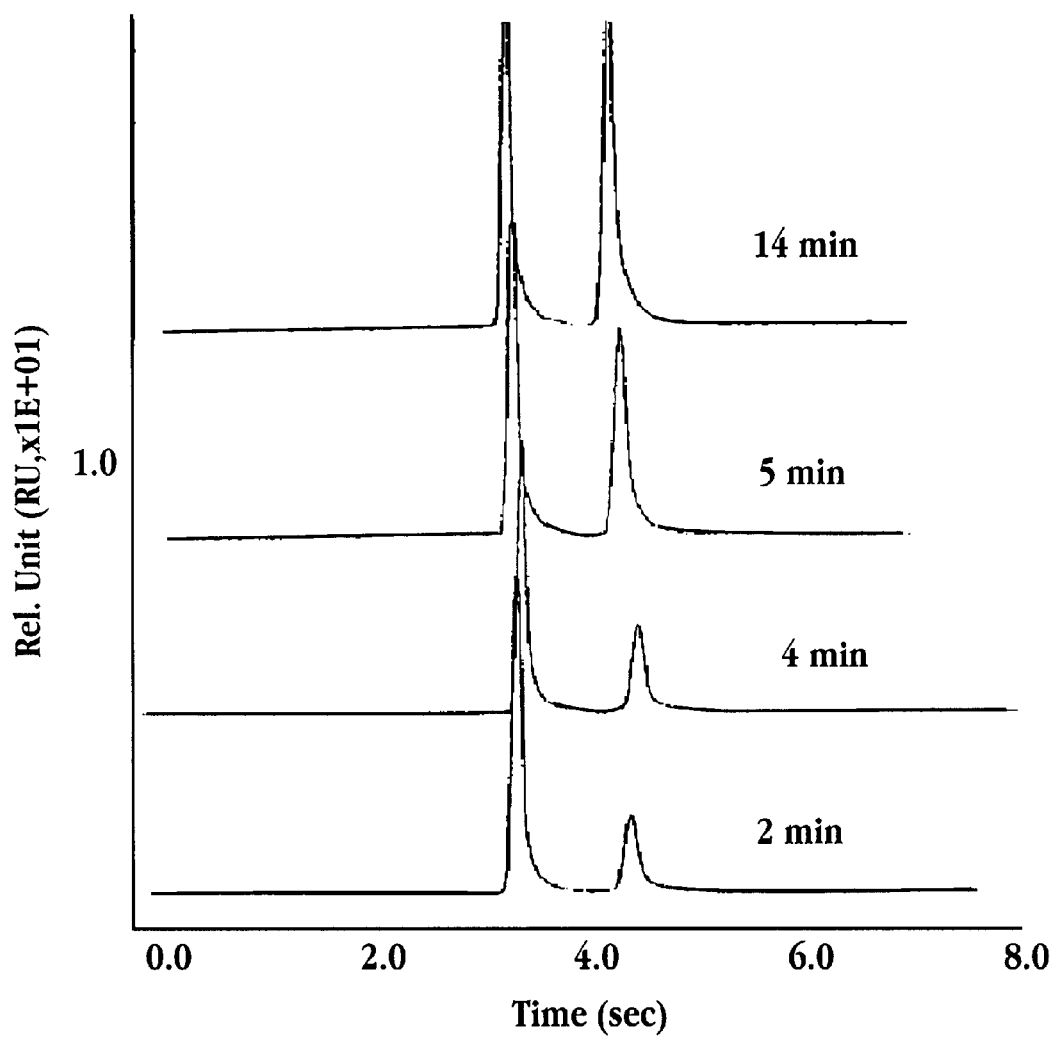
FIG. 17 is a series of electropherograms of an alkaline phosphatase assay taken at different times.

FIG. 17 illustrates the alkaline phosphatase activity for the different incubation times. As shown in the electropherograms, two product peaks (the first peak is fluorescein mono phosphate and the 2nd peak is fluorescein) are well separated from each other.

Figure 18:
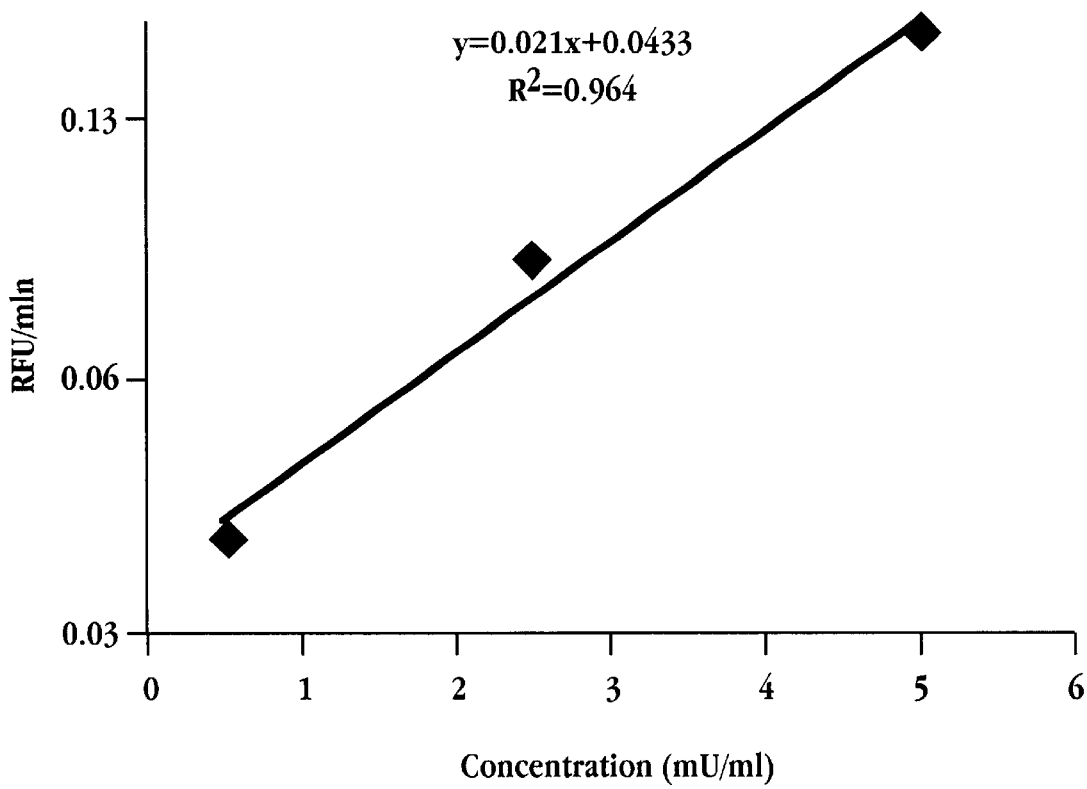
FIG. 18 is a calibration curve of the effect of varying alkaline phosphatase concentration.
Figure 19:
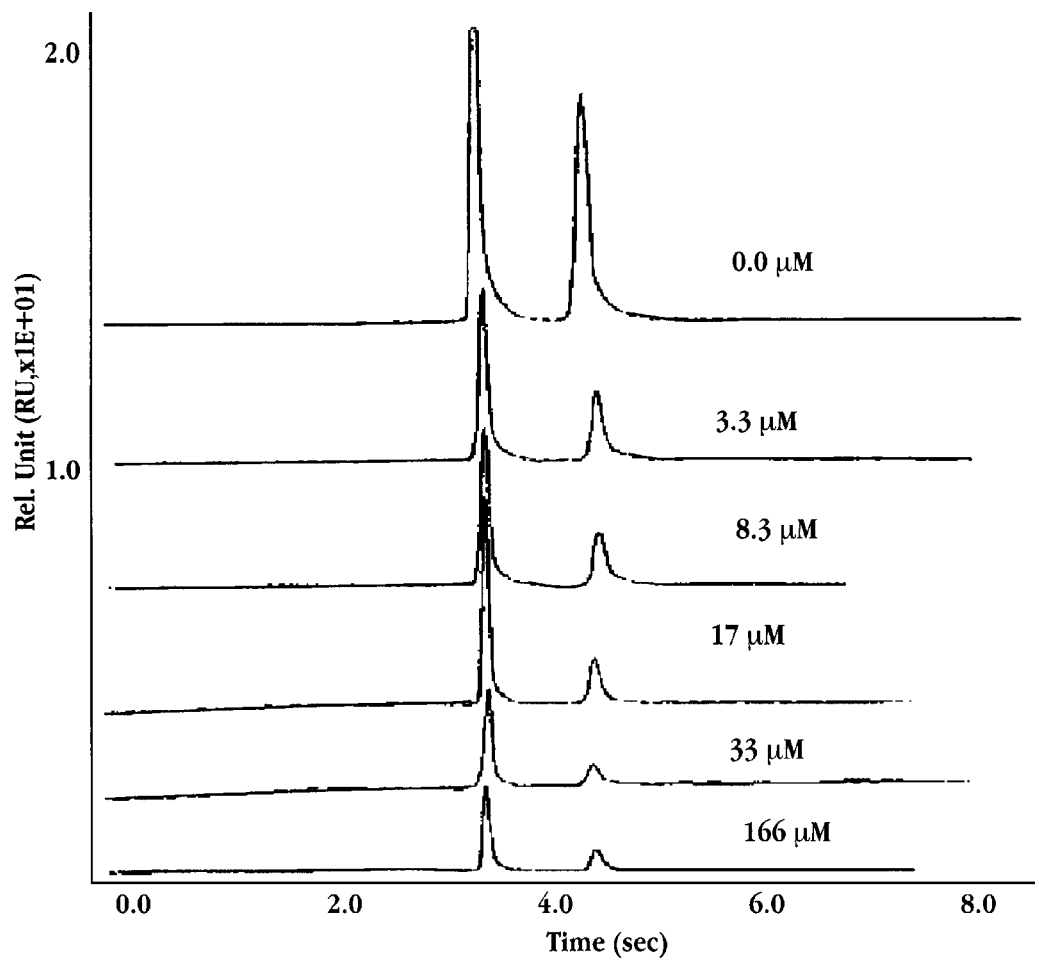
FIG. 19 is a series of electropherograms of an alkaline phosphatase assay using different concentrations of an inhibitor.
Figure 20:
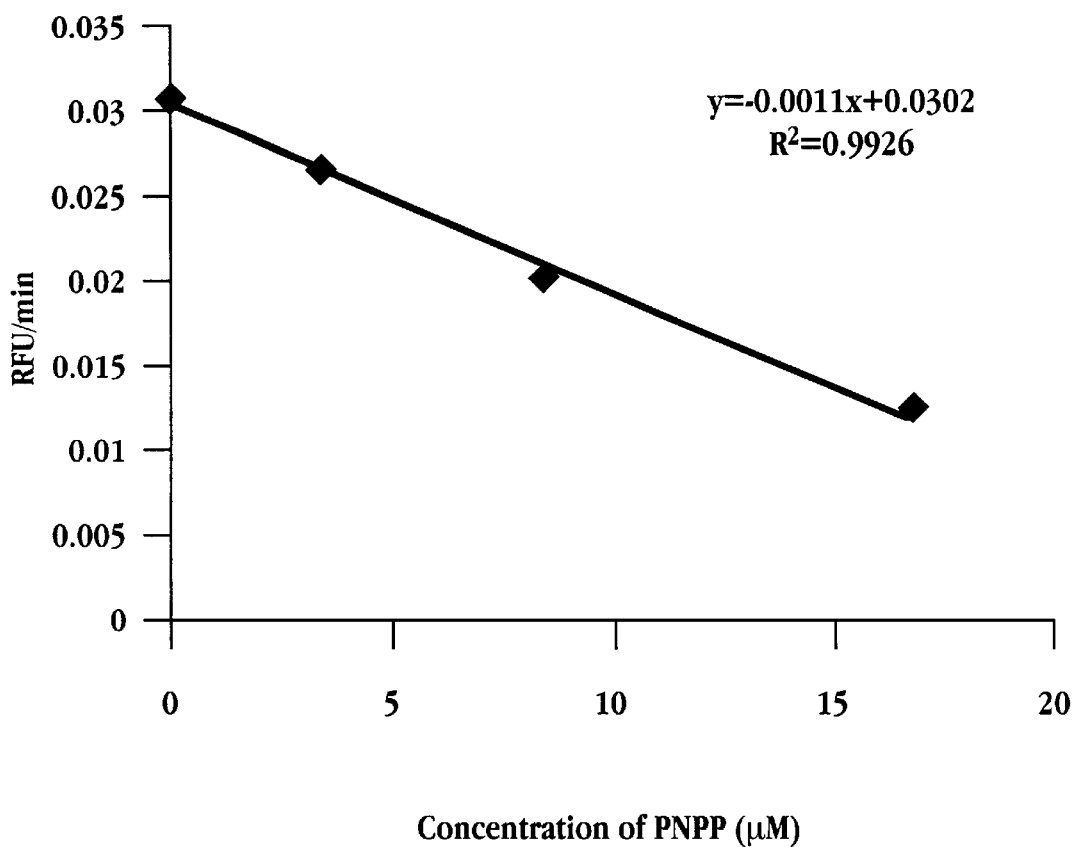
FIG. 20 is a calibration curve of the alkaline phosphatase assay using the data set forth in FIG. 19.

Additionally, the use of longer incubation time results in more conversion of FDP (fluorescein di-phosphate as a substrate) to the FMP (fluorescein mono-phosphate) and finally to fluorescein. FIG. 18 depicts a linear calibration curve for the alkaline phosphatase using the card. For the inhibition study, PNPP which is a non-fluorescent substrate for the alkaline phosphatase and competes with FDP which is a fluorescent substrate for the enzyme, is added to the assay mixture at a number of different concentrations. FIG. 19 shows different electropherograms from different assay mixtures containing 1.3 mU/ml alkaline phosphatase, 3.33 $\mu M$ of FDP, and different concentrations of PNPP as depicted in the figure. As can be seen, an increase of the concentration of PNPP results in a reduction of FDP alkaline phosphates activity. FIG. 20 shows a linear calibration curve for PNPP concentration.

The following example illustrates the subject device and method for a cytochrome P450 enzyme Reaction:

Reagents:
RECO System CYP3A4 Purified, Recombinant Human (Panvera Cat No. P2305).
RECO System CYP1A2 Purified, Recombinant Human (Panvera Cat No. P2304).
RECO System CYP2C9 Purified,. Recombinant Human (Panvera Cat No. P2362).
7-Benzyloxyquinoline (BQ) (Gentest Cat No. B720).
3-Cyano-7ethoxycoumarin (CEC) (Gentest Cat No. UC-455). Substrate for 1A2.
7-Methoxy-4-(trifluoromethyl)-coumarin (MFC) (Gentest Cat No. B740).
Acetonitrile.
B-Nicotinamide Adenine Dinucleotide Phosphate, Reduced Form (NADPH) (Sigma Cat No. 201-3).
Pluronic F68 (Sigma Cat No. P1300)

Cards:
Cards (Each unit comprised two reservoirs, a central well and a channel connecting the reservoirs and well. See FIG. 1 as to the configuration of the microstructures.) molded of black polystyrene and ultra sonically welded with plasma-treated LCF 3001 film were employed. A single pattern which has two evaporation control wells on a common channel, with an assay well centered on the channel between the evaporation control wells was used. This pattern has a 1 mm diameter assay well, tapering to 0.9 mm at the bottom. The reservoirs have a 2mm diameter, tapering to 1.9 mm.

Protocols:

The reagent solutions were prepared as follows.

Dissolve 7-Ethoxy-3-cyanocoumarin (CEC) 20 mM

Add 8.61 mg 7-ethoxy-3-cyanocoumarin to 2.0 mL acetonitrile. Invert to dissolve. Store at −20° C.

Dissolve 7-Methoxy-4-trifluoromethylcoumarin (MFC) 25 mM

Add 12.21 mg 7-methoxy-4-trifluoromethylcoumarin to 2.0 mL acetonitrile. Invert to dissolve. Store at −20° C.

Dissolve Benzyloxyquinoline (BQ) 20 mM

Add 4.706 mg benzyloxyquinoline to 1.0 mL acetonitrile. Invert to mix. Store at −20° C.

Dissolve NADPH 10 mM

B-Nicotinamide Adenine Dinucleotide Phosphate. Add 2.87 mg NADPH to 344 ul of deionized water. Invert to dissolve. Store at −20° C.

Furafylline 2.5 mM

Add 1.3 mg furafylline to 2.0 mL acetonitrile. Invert to dissolve.Note: Solution may precipitate upon storage at −20° C. but will redissolve when sonicated in warm water 5% Pluronic F68

Add 5.0 gm Pluronic F68 and bring to 100 mL with deionized water. Stir to dissolve.

EXAMPLE

Cytochrome P450 IA2 Enzymatic Assay

A. Cyp450 1A2 Enzymatic Activity:

Procedures:

1. Make 20 mM CEC substrate for Cyp450 1A2 enzyme.
2. Make fresh 10 mM NADPH solution with water.
3. Make Buffer Mix to be used to fill channels:

| 20 μl | Water |
| 20 μl | 5% Pluronic F68 |
| 20 μl | 5X CYP3A4 buffer |
| 20 μl | 20 mM CEC |
| 20 μl | 10 mM NADPH |
| 100 μl | Total vol. (enough for 10 reactions) |

4. Place card in holders.
5. Add 5 μl of the buffer mix to both of the side wells of the channels. Because the solution contains Pluronic F68, the middle assay mixture rises to the top of the well.
6. Add 300 nl of various concentrations of CYP450 1A2 enzyme to assay (middle) well.
7. Cover with 96 well plate cover. Incubate at 37° C. for 35 minutes.
8. Take RFU readings using Molecular Devices Fmax plated reader f-max settings: Filter pair 390/460; Int.20 ms; speed 10.

Results:

TABLE

CYP450 1A2 Enzyme Concentration vs. Reaction Signal

| [1A2], nM | 0 | 8 | 16 | 32 | 64 | 100 | 133 |
|---|---|---|---|---|---|---|---|
| RFU (mean) | 7.0 | 10.7 | 13.2 | 13.9 | 16.5 | 21.7 | 24.5 |
| RFU (std) | 1.5 | 1.8 | 1.3 | 1.0 | 0.6 | 3.1 | 4.2 |

The fluorescence signal increased linearly with the increase of the CYP450 1A2 enzyme concentration.

B: Inhibition in CYP450 1A2 Assay:

Protocols:

1. Make500·M CEC substrate for 1A2.
2. Make fresh 10 mM NADPH solution with water.
3. Make serial dilutions of furafylline at 2500, 1250, 250, 125, 25, 12.5, 2.5, 0·M concentrations
4. For each of the dilutions of furafylline make Buffer Mix:
   Water 14.85 μl
   5% Pluronic F68 9 μl
   500 μM CEC 0.9 μl
   CYP1A2 buffer (5×) 9 μl
   10 mM NADPH 11.25 μl
   Furafylline (from 0 to 2.5 mM) 1.8 μl
   Total Volume 45 μl (enough for 4 reactions)
5. Place card in holders.
6. Add 5 μl of the buffer mix to both of the side wells of the channels. Because the solution contains Pluronic F68, the solution in the middle assay well rises to the top. Dilute CYP1A2 enzyme 2:1 with water.
7. Add 300 nl of diluted enzyme to assay (middle) well.
8. Cover with 96 well plate cover.
9. Incubate at 37° C. for 35 minutes.
10. Take RFU readings using Molecular Devices F-max plate reader. F-max settings: Filter pair 390/460; Int.20 ms; speed 10.

Results:

TABLE

Percentage of Inhibition vs. Inhibitor Concentration

| [Inhibitor], μM | 133 | 66.5 | 13.3 | 6.65 | 1.33 | 0.665 | 0.133 |
|---|---|---|---|---|---|---|---|
| % of Inhibition | 78.0 | 77.0 | 75.0 | 72.0 | 64.0 | 31.0 | 2.0 |

It is evident from the above results that the subject devices and methods provide for efficient manipulations of small volumes and determinations of a wide variety of events, such as chemical reactions, binding events, enzyme reactions, and the like. The subject invention has great flexibility in the variety of protocols, which may be employed, with a single device allowing for different protocols. In addition, the subject devices may be combined with other devices, such as microtiter well plates, where the subject device may be in registry with the wells, so that samples may be readily followed and results recorded with confidence as to the compound involved.

Each document, reference or patent application, cited herein is incorporated by reference as if the reference was set forth verbatim in the text of this specification.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for performing operations in small volumes with a volatile solvent, said method comprising:

adding a component for said operation to a liquid zone having (i) an exposed opening to the atmosphere, (ii) an interior border whereby a meniscus is created at said border which is disposed within the zone that is spaced from the exposed opening, and (iii) containing said volatile solvent subject to evaporation;

wherein said liquid zone is in contact with a replenishing medium inma capillary channel; and maintaining a sample volume in said zone during said operation as said solvent undergoes evaporation by replenishing said sample volume with said replenishing medium from said capillary channel.

2. A method according to claim 1, wherein said capillary is connected to a reservoir of said replenishing medium.

3. A method according to claim 1, during said adding step, said liquid zone is in a well through a wall of said capillary channel, optionally at least a portion of the wall of said well is non-wettable, and said capillary channel is connected to two reservoirs.

4. A method according to claim 1, wherein said liquid zone is expressed from the end of said capillary channel.

5. A method according to claim 1, wherein said capillary channel is at least partially hydrophilic.

6. A method according to claim 1, wherein the total volume of liquid in said liquid zone is not more than about 5 $\mu$l.

7. A method according to claim 1, wherein after said operation, at least one component in said liquid zone is transferred through a capillary channel to an electrokinesis system.

8. A method according to claim 1, wherein said operation is an enzyme assay.

9. A method according to claim 1, wherein said operation is a ligand-receptor binding assay.

10. A method according to claim 1, wherein said operation is a reporter gene assay.

11. A method according to claim 1, during said adding step said interior border is formed as a result of border of a wettable and a non-wettable surface in said zone.

12. A method according to claim 1, during said adding step said interior border is formed as a result of a sharp change of direction of the wall of the zone.

13. A method according to claim 1, during said adding step said interior border is formed as a result of a hydraulic head.

* * * * *